(12) United States Patent
Lee et al.

(10) Patent No.: US 12,121,252 B2
(45) Date of Patent: *Oct. 22, 2024

(54) LOCKING APPARATUS

(71) Applicant: LIVSMED INC., Seongnam-si (KR)

(72) Inventors: Jung Joo Lee, Yongin-si (KR); Dong Wook Lee, Yongin-si (KR); Hee Jin Kim, Seongnam-si (KR)

(73) Assignee: LIVSMED INC., Seongnam-si (KR)

( * ) Notice: Subject to any disclaimer, the term of this patent is extended or adjusted under 35 U.S.C. 154(b) by 19 days.

This patent is subject to a terminal disclaimer.

(21) Appl. No.: 17/897,603

(22) Filed: Aug. 29, 2022

(65) Prior Publication Data

US 2023/0057173 A1 Feb. 23, 2023

Related U.S. Application Data

(63) Continuation of application No. 17/420,083, filed as application No. PCT/KR2019/014117 on Oct. 25, 2019, now Pat. No. 11,478,263.

(30) Foreign Application Priority Data

Dec. 31, 2018 (KR) ........................ 10-2018-0174237

(51) Int. Cl.
*A61B 17/28* (2006.01)
*A61B 17/29* (2006.01)
*A61B 17/00* (2006.01)

(52) U.S. Cl.
CPC ...... *A61B 17/2833* (2013.01); *A61B 17/2909* (2013.01); *A61B 2017/00367* (2013.01); *A61B 2017/0042* (2013.01); *A61B 2017/2925* (2013.01); *A61B 2017/2929* (2013.01); *A61B 2017/2946* (2013.01)

(58) Field of Classification Search
CPC ............ A61B 17/2833; A61B 17/2909; A61B 2017/00367; A61B 2017/0042; A61B 2017/2925; A61B 2017/2929; A61B 2017/2946
See application file for complete search history.

(56) References Cited

U.S. PATENT DOCUMENTS

| | | | |
|---|---|---|---|
| 7,476,244 B2 | 1/2009 | Buzzard et al. | |
| 8,186,242 B2 | 5/2012 | Uesaka | |
| 2009/0198272 A1 | 8/2009 | Kerver et al. | |
| 2010/0041945 A1 | 2/2010 | Isbell, Jr. | |

(Continued)

FOREIGN PATENT DOCUMENTS

| | | |
|---|---|---|
| CN | 207261506 U | 4/2018 |
| JP | 55-76205 A | 6/1980 |

(Continued)

OTHER PUBLICATIONS

Extended European Search Report for EP Application No. 19907666 issued on Aug. 12, 2022.

(Continued)

*Primary Examiner* — Brooke Labranche
(74) *Attorney, Agent, or Firm* — Bridgeway IP Law Group, PLLC; Sang Ho Lee; Hyun Woo Shin

(57) ABSTRACT

Provided is a locking apparatus, and more particularly, to a locking apparatus with improved locking performance as a locking unit is stuck between different members capable of moving relative to each other and in which locking is released as an unlocking unit pushes the locking unit.

37 Claims, 31 Drawing Sheets

(56) References Cited

U.S. PATENT DOCUMENTS

| | | |
|---|---|---|
| 2016/0302840 A1 | 10/2016 | Scheib et al. |
| 2017/0000481 A1 | 1/2017 | Cauldwell et al. |
| 2017/0172595 A1 | 6/2017 | Lathrop |
| 2018/0049739 A1 | 2/2018 | Kasvikis |
| 2018/0228506 A1 | 8/2018 | Lee et al. |
| 2018/0303567 A1 | 10/2018 | Simi et al. |
| 2018/0360550 A1 | 12/2018 | Nakanishi |

FOREIGN PATENT DOCUMENTS

| | | | |
|---|---|---|---|
| JP | 55-165385 | A | 12/1980 |
| JP | 2002-106523 | A | 4/2002 |
| JP | 2002-141102 | A | 5/2002 |
| JP | 2004-130074 | A | 4/2004 |
| JP | 2008-075867 | A | 4/2008 |
| JP | 2011-067325 | A | 4/2011 |
| JP | 5328325 | B2 | 10/2013 |
| JP | 2014-529429 | A | 11/2014 |
| JP | 2015-128616 | A | 7/2015 |
| JP | 2017-018576 | A | 1/2017 |
| JP | 2017-532127 | A | 11/2017 |
| KR | 10-2010-0076759 | A | 7/2010 |
| KR | 10-2012-0114984 | A | 10/2012 |
| KR | 10-1223469 | B1 | 1/2013 |
| KR | 10-2018-0073608 | A | 7/2018 |
| KR | 10-2018-0090350 | A | 8/2018 |

OTHER PUBLICATIONS

Notice of Reason for Refusal for Japanese application No. 2021-536003 issued on Jul. 7, 2022.

Korean Intellectual Property Office, "Request for Submission of an Opinion" for counterpart Korean patent application No. 10-2023-0021697, issued on Oct. 19, 2023.

Japanese Patent Office, "Notice of Reasons for Refusal" for counterpart Japanese patent application No. 2023-017959, issued on Apr. 2, 2024.

LOCKING APPARATUS

CROSS-REFERENCE TO RELATED APPLICATION(S)

The present application is a continuation of U.S. application Ser. No. 17/420,083 filed on Jun. 30, 2021, which a national-stage under 35 USC 371 of international application No. PCT/KR2019/014117 filed on Oct. 25, 2019, and claims priority to Korean patent application No. 10-2018-0174237 filed on Dec. 31, 2018, the entire disclosures of which are hereby incorporated by reference.

TECHNICAL FIELD

The disclosure relates to a locking apparatus, and more particularly, to a locking apparatus having improved locking performance between members that are different from each other and capable of relative movement.

BACKGROUND ART

In general, in equipment in which a relative movement between members different from each other is possible, for example, a linear motion or a rotational motion, a situation occurs when a user is forced to restrict a movement of the equipment as necessary.

In order to prevent a relative movement between members different from each other according to the related art, a connection member for connecting the different members may be coupled to each member to fix the location of the member, or a magnet installed in each member is used to prevent a relative movement between the members via a magnetic force. However, such a configuration separately needs locking parts and a coupling structure between respective members, which complicates the structure.

Korean Patent No. 10-1223469 (registered on Jan. 11, 2013, and entitled "Locking Apparatus") discloses the background technology of the disclosure.

DESCRIPTION OF EMBODIMENTS

Technical Problem

To address the above problems, the objective of the disclosure is to facilitate switching to a locking state to prevent a movement at any position in a certain section, not at a certain fixed position, and to reduce free play in the locking state.

In detail, the objective is to improve the locking performance by preventing a relative movement of a first body part and a second body part by a frictional force generated by a locking unit stuck therebetween, and to release the locking state via an unlocking unit that pushes the locking unit.

Solution to Problem

According to embodiments of the disclosure, a locking apparatus includes a first body part, a second body part capable of a relative movement with respect to the first body part, a locking unit capable of moving within an interval between the first body part and the second body part and simultaneously contacting the first body part and the second body part, and an unlocking unit disposed on a movement path of the locking unit and capable of pushing the locking unit in a direction away from the first body part or the second body part, wherein, when the locking unit simultaneously contacts the first body part and the second body part, a movement of the second body part with respect to the first body part in at least one direction is prevented.

In the disclosure, the interval between the first body part and the second body part may decrease in any one direction in a certain section where the first body part and the second body part face each other, and when the locking unit simultaneously contacts the first body part and the second body part in the section, the second body part may be prevented from moving in a direction in which the interval with the first body part decreases.

In the disclosure, the unlocking unit may push the locking unit in a direction in which an interval between one side of the first body part and one side of the second body part, which face each other, in a certain section increases, so as to enable a relative movement between the first body part and the second body part, which is prevented by the locking unit.

In the disclosure, the locking unit may include a locking main body part, and the locking main body part may include a contact part disposed between the first body part and the second body part, and an elastic member connected to the first body part, having elastic resilience, and pushing the contact part in a direction in which the interval between the first body part and the second body part decreases.

In the disclosure, as the contact part is pushed by the elastic member in a direction in which the interval between the first body part and the second body part decreases, a state in which a movement of the second body part with respect to the first body part in one or more directions is prevented may be maintained.

In the disclosure, the contact part may have a ball shape or a cylindrical shape.

In the disclosure, the second body part may be disposed inside the first body part, and one side of the second body part which faces the first body part may form an interval with the first body part which decreases in one direction, and the other side facing the one side may contact the first body part.

In the disclosure, the second body part may be flat and movable inside the first body part.

In the disclosure, the first body part may extend to be symmetric toward both sides with respect to a center portion thereof, the locking unit may include a plurality of locking units and may be disposed at both sides of the center portion of the first body part, the unlocking unit may include a plurality of unlocking units corresponding to the plurality of locking units and is capable of pushing the locking unit, and when the locking unit simultaneously contacts the first body part and the second body part, the first body part and the second body part may be prevented from moving in both directions.

In the disclosure, the second body part may be disposed inside the first body part, and an interval between inner circumferential surfaces of the first body part, which faces the second body part, may decrease in one direction.

In the disclosure, the second body part may be flat, and the first body part may be symmetrically formed with respect to a movement axis of the second body part as an axis of symmetry.

In the disclosure, the locking unit and the unlocking unit may respectively include a plurality of locking units and a plurality of unlocking units, which are disposed at both sides with respect to a movement axis of the second body part as an axis of symmetry.

In the disclosure, the first body part may extend to be symmetric toward both sides with respect to a center portion thereof, the locking unit may include a plurality of locking units and be disposed at both sides of the center portion of the first body part, the unlocking unit may include a plurality of unlocking units corresponding to the plurality of locking units and be capable of pushing the locking unit, and when the locking unit simultaneously contacts the first body part and the second body part, the first body part and the second body part may be prevented from moving in both directions.

In the disclosure, the second body part may be coaxial with the first body part and rotatably disposed outside the first body part.

In the disclosure, the second body part may have a hollow, and the first body part may be disposed inside the second body part.

In the disclosure, the second body part may be rotatable clockwise or counterclockwise.

In the disclosure, the interval between the first body part and the second body part, which face each other, may decrease in a clockwise or counterclockwise direction.

In the disclosure, the locking unit may include a plurality of locking units in a movement direction of the second body part, and the unlocking unit may include a plurality of unlocking units corresponding to the plurality of locking units.

In the disclosure, the interval between the first body part and the second body part may decrease in a clockwise or counterclockwise direction in at least one section where the first body part and the second body part face each other, and decrease in a direction different from the clockwise or counterclockwise direction in at least other section where the first body part and the second body part face each other.

In the disclosure, the one section and the other section each may include a plurality of sections between the first body part and the second body part, the locking unit may include a plurality of locking units corresponding to a plurality of the one sections and the other sections, and the unlocking unit may include a plurality of unlocking units corresponding to the plurality of locking units.

In the disclosure, the unlocking unit may be coaxial with the first body part and the second body part and capable of rotating clockwise or counterclockwise around a co-axis as a rotation axis.

In the disclosure, the unlocking unit may include an unlocking main body that is disposed on a movement path of the locking unit and pushes the locking unit in a direction in which the interval between the first body part and the second body part, which face each other, increases.

In the disclosure, the locking unit may include a plurality of locking units in a movement direction of the second body part, and the unlocking main body may include a plurality of unlocking main bodies corresponding to the plurality of locking units.

In the disclosure, the locking apparatus may further include a pushing plate part that transmits power to the unlocking unit and pushes the unlocking unit.

In the disclosure, the pushing plate part may linearly reciprocate and may push the unlocking unit.

In the disclosure, when one side of the pushing plate part pushes the unlocking unit, the unlocking unit may move in a direction in which the interval between the first body part and the second body part, which face each other, increases.

In the disclosure, one surface of the pushing plate part that may contact the unlocking unit may be an inclined surface forming a certain angle with a movement axis of the pushing plate part.

In the disclosure, the locking unit may include a first locking unit that may move in the at least one section, and a second locking unit that may move in the at least other section, and, when the first locking unit and second locking unit simultaneously contact the first body part and the second body part, the second body part may be prevented from rotating in both clockwise and counterclockwise directions.

In the disclosure, each of the first locking unit and the second locking unit may be provided in one pair to be origin-symmetric with respect to a rotation center of the second body part as the origin.

In the disclosure, the unlocking unit may be coaxial with the first body part and the second body part and may rotate around a co-axis as a rotation axis clockwise or counterclockwise.

In the disclosure, the unlocking unit may include a first unlocking unit that may push the first locking unit, and a second unlocking unit rotating in a direction opposite to a rotational direction of the first unlocking unit and pushing the second locking unit.

In the disclosure, each of the first and second unlocking unit may include an unlocking main body that is disposed on a movement path of the first and second locking unit and may push each of the first and second locking unit in a direction in which the interval between the first body part and the second body part, which face each other, increases.

In the disclosure, the unlocking main body may include a plurality of unlocking main bodies that may push first and second locking units that are origin-symmetric with respect to a rotation center of the second body part as an origin and provided in one pair.

In the disclosure, the locking apparatus may further include a pushing plate part that transmits power to the first and second unlocking units and may push the first and second unlocking units.

In the disclosure, the pushing plate part may linearly reciprocate and may simultaneously push the first and second unlocking units.

In the disclosure, when the pushing plate part pushes the first and second unlocking units, the first and second unlocking units may be moved in a direction in which the interval between the first body part and the second body part, which face each other, increases.

In the disclosure, each surface of the pushing plate part that contacts the first and second unlocking units at both sides with respect to a movement axis of the pushing plate part may be an inclined surface forming a certain angle with a movement axis of the pushing plate part.

In the disclosure, the inclined surface may include a plurality of inclined surfaces for pushing first and second locking units that are origin-symmetric with respect to a rotation center of the second body part as an origin and provided in one pair.

Other aspects, features, and advantages other than those described above will become apparent from the following drawings, claims and detailed description of the invention.

Advantageous Effects of Disclosure

According to the locking apparatus according to the disclosure, a relative movement between members different from each other may be prevented due to friction generated as the locking unit is stuck between members different from each other.

Furthermore, the locking apparatus, particularly the unlocking unit, transmits power to the locking unit to selectively release the locking state of the locking apparatus, thereby improving locking performance.

Furthermore, regardless of the positions of the members different from each other, when the locking unit is stuck between the members different from each other by the locking apparatus, a relative movement between the members different from each other may be prevented by a frictional force generated by the locking unit stuck therebetween.

Furthermore, when an external force applied to the locking unit that is in a locking state by being stuck between the members different from each other increases, the frictional force generated as the locking unit is stuck therebetween increases, thereby improving locking performance.

BEST MODE

Figure 1A:
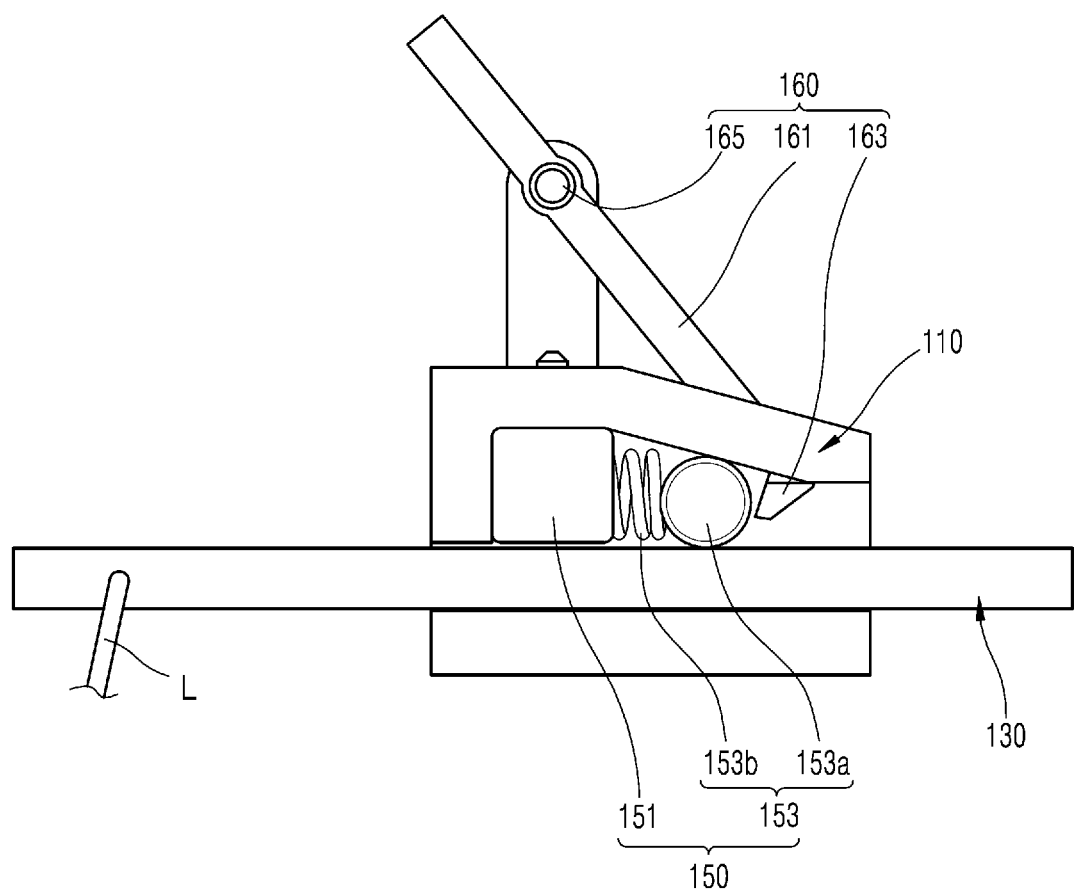
FIG. 1A is a perspective view of a locking apparatus according to an embodiment.

As the disclosure allows for various changes and numerous embodiments, particular embodiments will be illustrated in the drawings and described in detail, in the written description. However, this is not intended to limit the disclosure to particular modes of practice, and it is to be appreciated that all changes, equivalents, and substitutes that do not depart from the spirit and technical scope of the disclosure are encompassed in the disclosure. In the description of the disclosure, certain detailed explanations of related art are omitted when it is deemed that they may unnecessarily obscure the essence of the disclosure.

While such terms as "first," "second," etc., may be used to describe various components, such components must not be limited to the above terms. The above terms are used only to distinguish one component from another.

The terms used in the specification, are merely used to describe embodiments, and are not intended to limit the disclosure. An expression used in the singular encompasses the expression of the plural, unless it has a clearly different meaning in the context. In the specification, it is to be understood that the terms such as "including," "having," and "comprising" are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

The disclosure will now be described more fully with reference to the accompanying drawings, in which embodiments of the disclosure are shown. Throughout the drawings, like reference numerals denote like elements. In the following description, when detailed descriptions about related well-known functions or structures are determined to make the gist of the disclosure unclear, the detailed descriptions will be omitted herein.

Furthermore, in the description of various embodiments of the disclosure, it is not necessary to independently interpreted or worked each embodiment, and technical concepts described in the respective embodiments should be understood to be interpreted or worked by being combined to another embodiment that is individually described <Locking Apparatus According to an Embodiment>

Figure 1B:
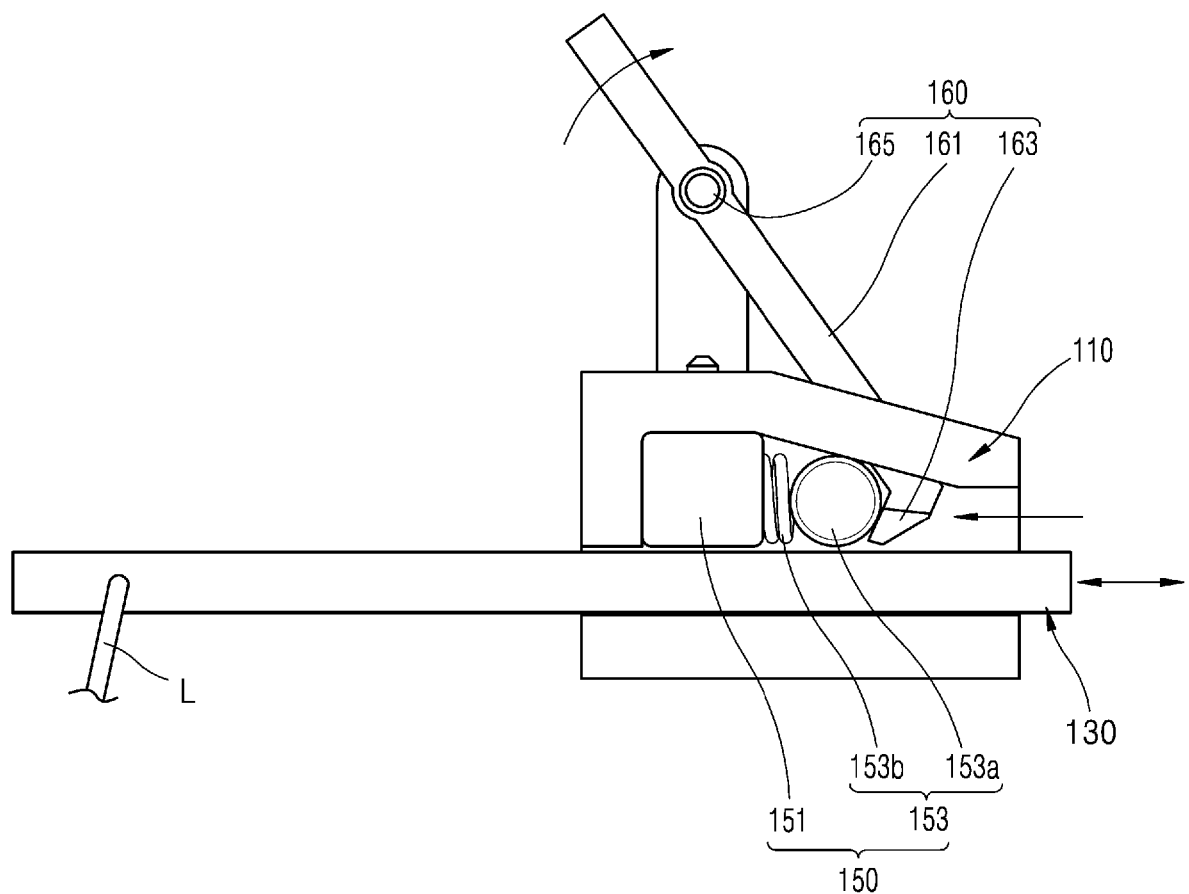
FIG. 1B illustrates an unlocking state of the locking apparatus of FIG. 1A.
Figure 2:
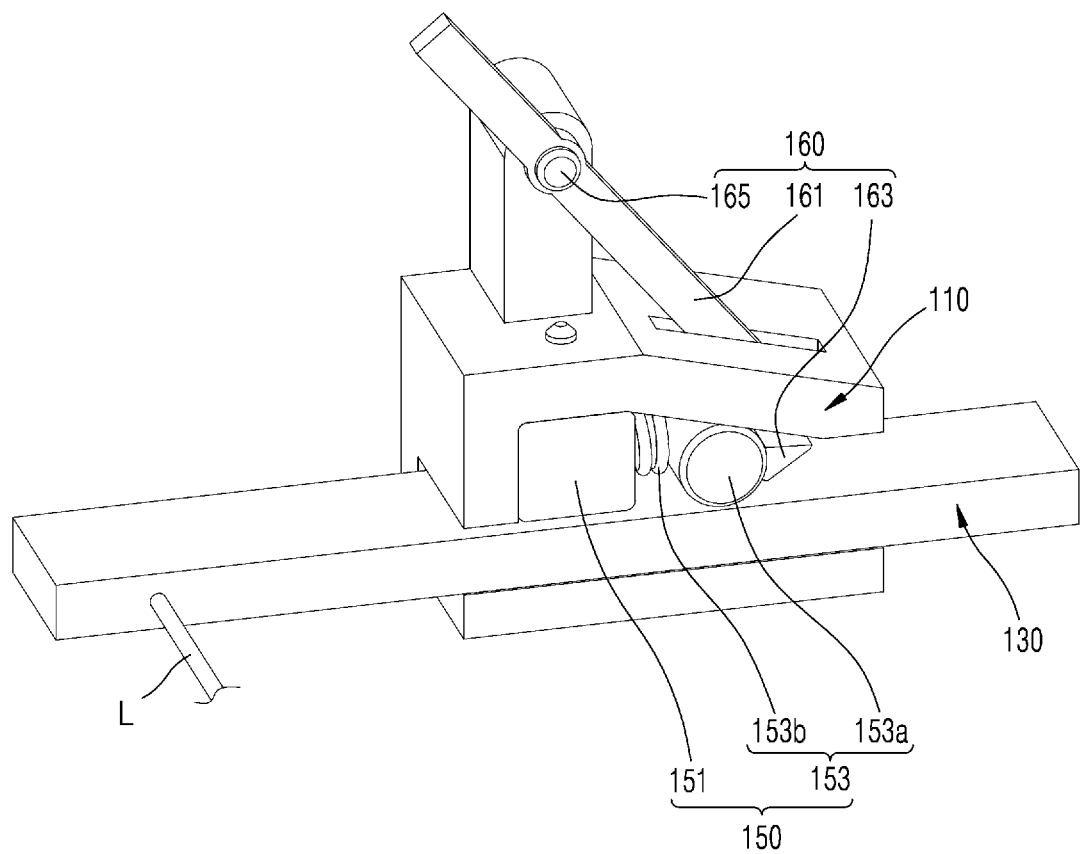
FIG. 2 is a perspective view of the locking apparatus in a locking state according to an embodiment.
Figure 3:
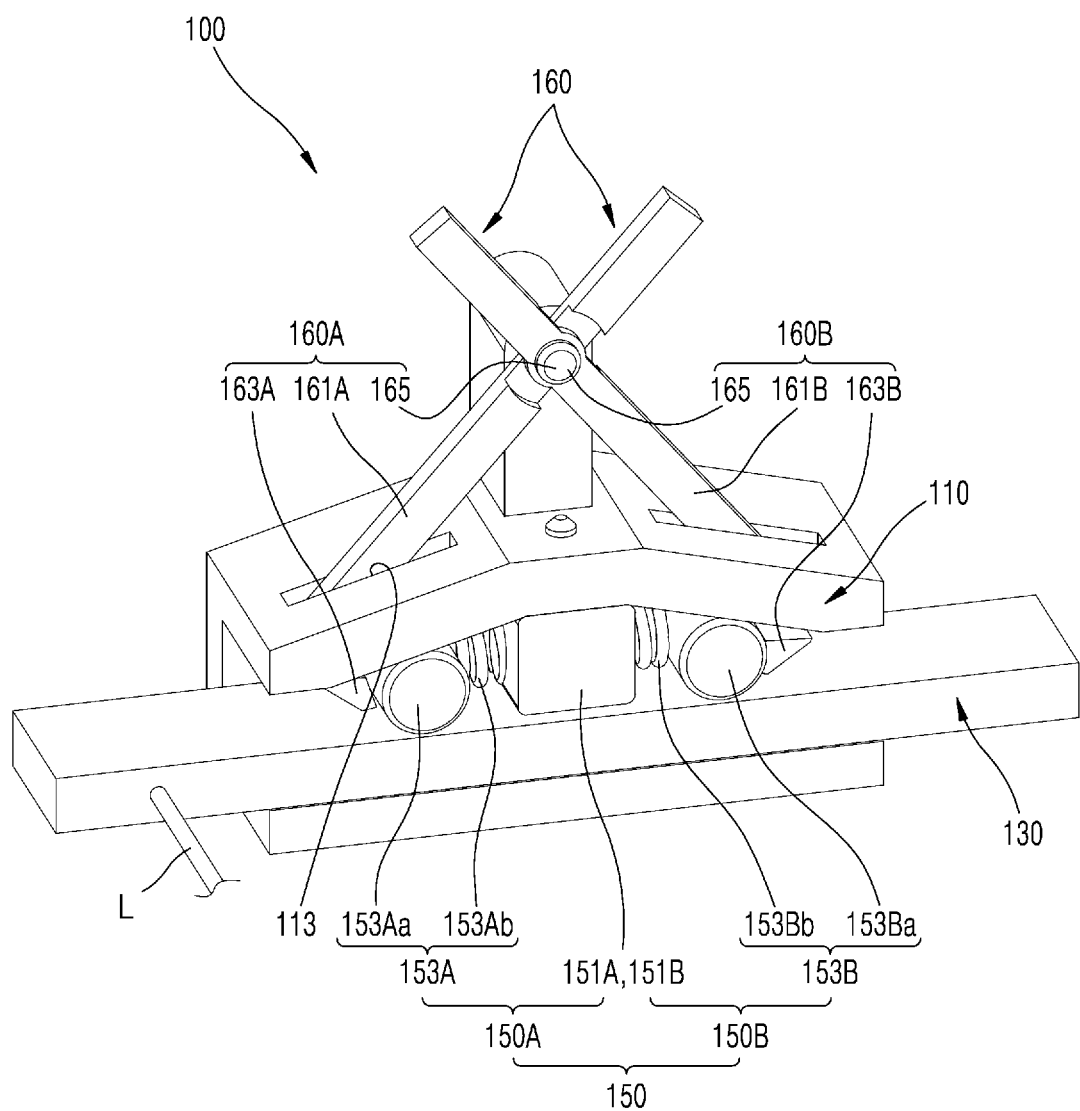
FIG. 3 is a perspective view of a locking apparatus according to a modification of the embodiment.
Figure 4:
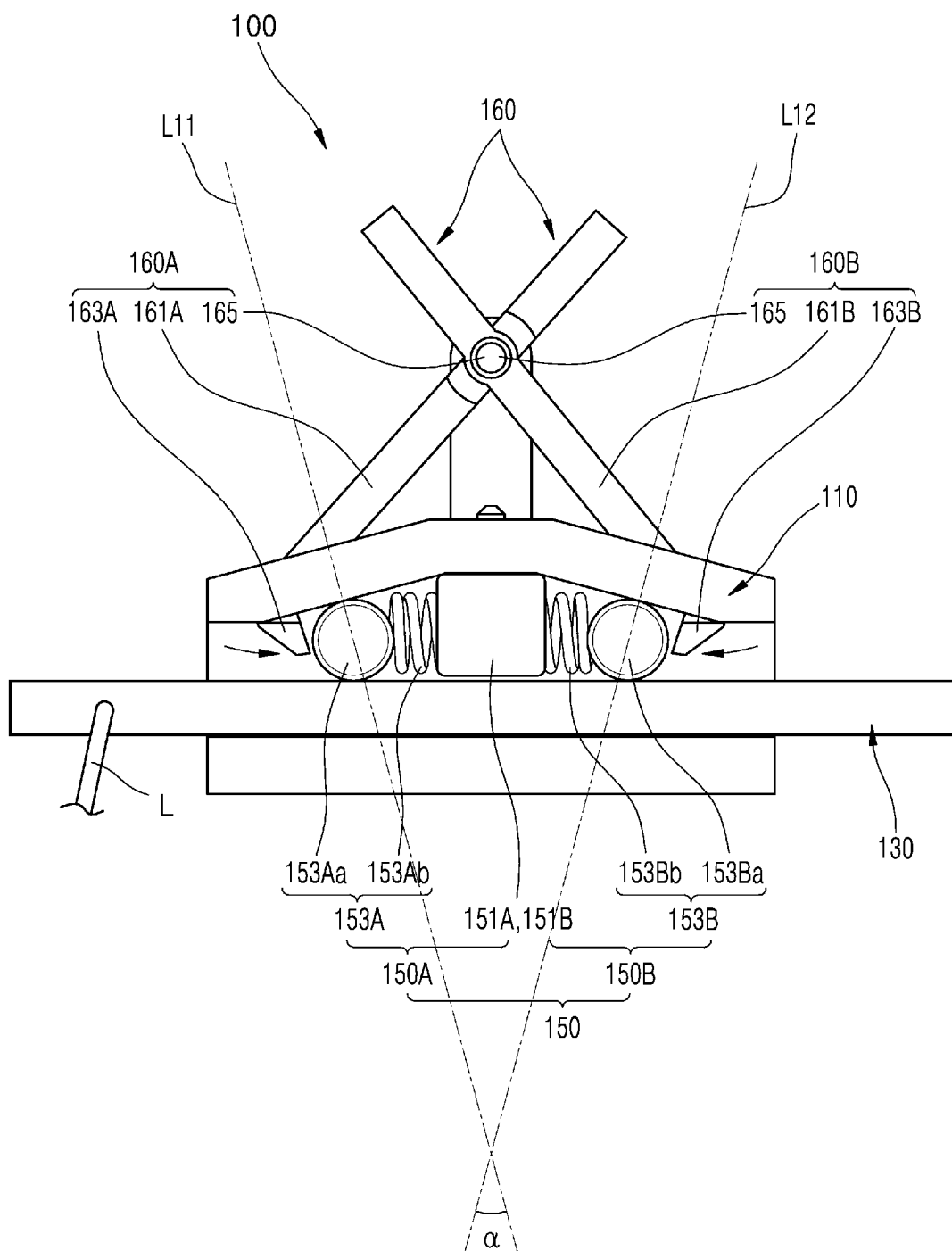
FIG. 4 illustrates a locking state of the locking apparatus of FIG. 3.
Figure 5:
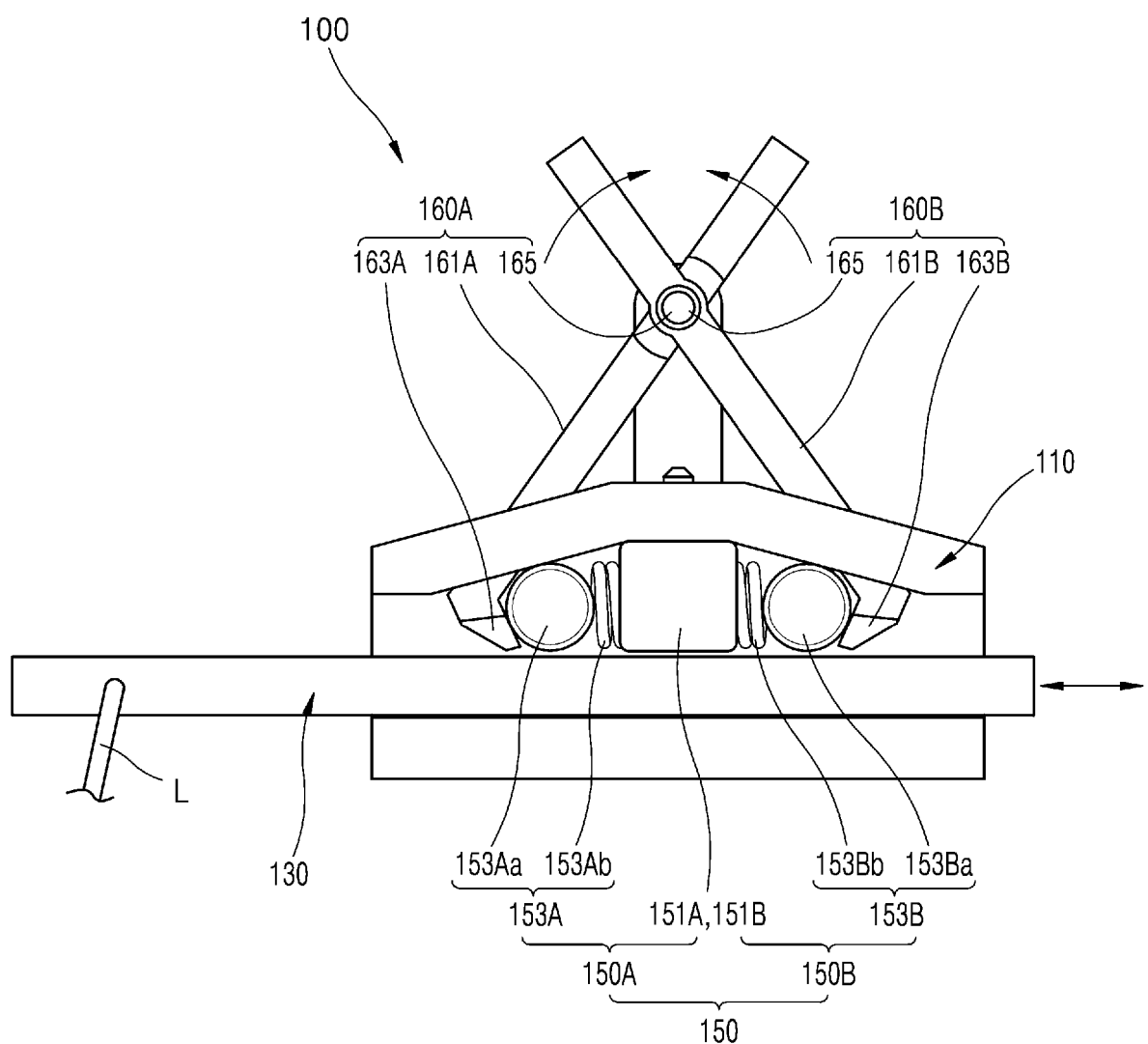
FIG. 5 illustrates an unlocking state of the locking apparatus of FIG. 3.

A locking apparatus according to an embodiment is described below with reference to the accompanying drawings. FIG. 1A is a perspective view of a locking apparatus according to an embodiment. FIG. 1B illustrates an unlocking state of the locking apparatus of FIG. 1A. FIG. 2 is a perspective view of the locking apparatus in a locking state according to an embodiment. FIG. 3 is a perspective view of a locking apparatus according to a modification of the embodiment. FIG. 4 illustrates a locking state of the locking apparatus of FIG. 3. FIG. 5 illustrates an unlocking state of the locking apparatus of FIG. 3.

Referring to FIGS. 1A to 5, a locking apparatus 100 according to an embodiment according to an embodiment may include a first body part 110, a second body part 130, a locking unit 150, and an unlocking unit 160.

Referring to FIGS. 1A, 1B, and 2, a movement path, along which the second body part 130 that is described below is movable, may be formed in the first body part 110. The movement path may be formed in the form of a groove in the first body part 110, particularly between inner surfaces of the first body part 110 which face each other.

The second body part 130 may be move in the movement path formed in the first body part 110. In detail, the second body part 130 is moved in the horizontal direction (based on FIG. 2) between the inner surfaces of the first body part 110 and is capable of moving relative to the first body part 110.

A connection member L such as a wire may be connected to the second body part 130, and the connection member L may be connected to a part that is capable of linear motion and rotational motion in equipment such as surgical instruments 1 and 2 that are described later.

Referring to FIGS. 1A, 1B, and 2, the second body part 130 according to an embodiment may be capable of moving relative to the first body part 110, and is capable of moving on the movement path formed in the first body part 110.

The second body part 130 may be moveable on the movement path in the horizontal direction (based on FIG. 2), may be disposed on the movement path formed in the first body part 110, and may face the inner surfaces of the first body part 110 disposed at upper and lower sides of the second body part 130 (based on FIG. 2).

Referring to FIGS. 1A, 1B, and 2, the second body part 130 may contact one inner surface of the first body part 110 disposed under the second body part 130 (based on FIG. 2), thereby generating a frictional force, and may be separated from the inner surface of the first body part 110 disposed above the second body part 130 (based on FIG. 2).

The locking unit 150 that is described later may be disposed between an upper surface of the second body part 130 (based on FIG. 2) and the inner surface of the first body part 110 which faces the upper surface of the second body part 130, and the second body part 130 may be in an unlocking state in which the second body part 130 is capable of moving relative to each other with respect the first body part 110, or in a locking state in which a relative movement is prevented, according to the location of the locking unit 150.

The locking state and the unlocking state are described later in detail.

Referring to FIGS. 1A, 1B, and 2, the second body part 130 according to an embodiment may have a cuboid shape and may be capable of linear motion in the horizontal direction (based on FIG. 2). However, the disclosure is not limited thereto, and various modifications of the embodiments are available, for example, the second body part 130 has a circular shape having a certain radius of curvature and is capable of moving on the movement path formed in the first body part 110.

When the second body part 130 has a certain radius of curvature, one inner surface of the first body part 110 that is capable of contacting the second body part 130 may have a certain radius of curvature to correspond to the shape of the second body part 130.

Referring to FIGS. 1A, 1B, and 2, according to an embodiment, an interval between one surface of the first body part 110 and one surface of the second body part 130 may decrease in one direction.

In detail, among the inner surfaces of the first body part 110, the inner surface of the first body part 110 that is disposed under the second body part 130 (based on FIG. 2) is in contact with an outer surface of the second body part 130 (based on a lower side in FIG. 2). A lower inner surface of the first body part 110 has a flat shape, and an interval between the first body part 110 and a lower surface of the second body part 130 in a certain section may be maintained constant.

Among the inner surfaces of the first body part 110, the inner surface of the first body part 110 that is disposed above the second body part 130 (based on FIG. 2) is disposed to face the second body part 130, particularly the upper surface of the second body part 130 (based on FIG. 2) with the locking unit 150 therebetween.

An upper inner surface of the first body part 110 is inclined by a certain degree, and thus an interval between the first body part 110 and the upper surface of the second body part 130 may be changed in a certain section.

Accordingly, in the certain section, the locking unit 150 that is disposed between the first body part 110 and the second body part 130 and capable of moving may simultaneously contact the first body part 110 and the second body part 130.

Furthermore, except a section in which the locking unit 150 simultaneously contacts the first body part 110 and the second body part 130, the locking unit 150 may be disposed to contact only one of the first body part 110 and the second body part 130, and unless the locking unit 150 simultaneously contacts the first body part 110 and the second body part 130, the second body part 130 may be capable of moving relative to the first body part 110.

Referring to FIG. 2, in the locking apparatus 100 according to an embodiment, an interval between one surface of the first body part 110 disposed above the upper side of the second body part 130 (based on FIG. 2) and one surface of the second body part 130 (based on an upper surface in FIG. 2) may decrease in the first body part 110 in one direction (based on the direction from left to the right in FIG. 2).

In detail, the interval between one surface of the first body part 110 and one surface of the second body part 130, which face each other, may decrease from a left end portion of the first body part 110 (based on FIG. 2) in an outward direction (based on a direction from the left to the right in FIG. 2). Referring to FIG. 2, an interval between the upper surface of the second body part 130 that is flat (based on FIG. 2) and the inner surface of the first body part 110 facing the same may decrease in a direction from one end portion to the other end portion.

Referring to FIGS. 1A, 1B, and 2, the locking unit 150 according to an embodiment, which is capable of moving between the first body part 110 and the second body part 130, may include a support part 151 and a locking main body part 153.

The support part 151 is coupled to the first body part to be fixedly located, and may be coupled to the first body part 110 by using a fastening member such as a bolt in the disclosure. However, the disclosure is not limited thereto, and the support part 151 may be integrally formed with the first body part 110.

The locking main body part 153 may be coupled to the support part 151 to be capable of moving between the first body part 110 and the second body part 130 and may include a contact part 153a and an elastic member 153b.

Referring to FIGS. 1A, 1B, and 2, the unlocking unit 160 according to an embodiment, which is connected to the first body part 110, may push the locking unit 150, particularly the contact part 153a, in a direction in which the interval between the respective surfaces of the first body part 110 and the second body part 130, which face each other, increases.

In the specification, "pushing" denotes pushing from one side toward the other side.

In this regard, in FIGS. 3 to 5, a plurality of locking units and a plurality of unlocking units are provided as the locking unit 150 and the unlocking unit 160, respectively, at both sides with respect to a center portion of the first body part 110, which is described later in detail.

In brief, referring to FIG. 3, according to a modification of the embodiment, the first body part 110 and the second body part 130 may be symmetrically formed with respect to the center portion.

Referring back to FIGS. 1A, 1B, and 2, in the disclosure, when the locking unit 150 that is described later is moved in the outward direction (based on the direction from the left to the right in FIG. 1A) from one end portion of the first body part 110 between the first body part 110 and the second body part 130, the locking unit 150 may simultaneously contact the first body part 110 and the second body part 130.

In the locking apparatus 100 according to an embodiment, the second body part 130 is form flat, and assuming that the movement direction of the second body part 130 (based on the horizontal direction in FIG. 2) is set to be a horizontal direction, the inner surface of the first body part 110 facing the upper surface of the second body part 130 (based on FIG. 2) may form an acute angle with an axis of the second body part 130 in the horizontal direction.

In detail, referring to FIG. 1A, with respect to the one end portion of the first body part 110 where the support part 151 is disposed (based on the left end portion in FIG. 1A), in the right direction (based on FIG. 1A), the inner surface of the first body part 110 facing the upper surface of the second body part 130 (based on FIG. 2) may be inclined downward toward the right.

Referring to FIG. 2, with respect to one end portion (left end portion), the interval between the first body part 110 and the second body part 130 decreases toward the right, and when the locking unit 150 moving between the first body part 110 and the second body part 130 moves from the left to the right (based on FIG. 2), the locking unit 150 simultaneously contacts the first body part 110 and the second body part 130.

In this state, a frictional force may be generated between the contact part 153a of the locking unit 150 and each of the first body part 110 and the second body part 130. In this state, when the second body part 130 is moved from the left to the right (based on FIG. 3), the contact part 153a is moved together to the right by the frictional force between the contact part 153a and the second body part 130.

As the contact part 153a moves to the right, the inner surface of the first body part 110 that is inclined to the lower right by a certain angle may further increase the frictional force between the contact part 153a and each of the first body part 110 and the second body part 130, and simultaneously the frictional force between the lower surface of the second body part 130 and the inner surface of the first body part 110 facing the same may be increased much.

Accordingly, the second body part 130 may be difficult to move further to the right.

In other words, when the contact part 153a simultaneously contacts the first body part 110 and the second body part 130, as the second body part 130 is moved further to the right, the contact part 153a is stuck between the first body part 110 and the second body part 130, and thus the second body part 130 is prevented from moving to the right.

The frictional force generated from being stuck and preventing the movement of the second body part 130 is increased further because a phenomenon that the contact part 153a is further stuck between the first body part 110 and the second body part 130 occurs as a force to move the second body part 130 to the right increases, and thus the frictional force further prevents the movement of the second body part 130 and establishes a locking state.

However, even when the contact part 153a simultaneously contacts the first body part 110 and the second body part 130, if the second body part 130 is moved toward the left by a certain external force, then the contact part 153a is moved toward the left together by the frictional force between the contact part 153a and the second body part 130.

As the contact part 153a moves toward the left side, the contact part 153a is separated from the inner surface of the first body part 110 that is inclined to the upper left, and thus, unlike the above case, the second body part 130 may freely move.

In other words, in the structure as shown in FIGS. 1A and 2, the movement of the second body part 130 in the right direction in which the interval in which the contact part 153a is accommodated may be restricted, but reversely the movement of the second body part 130 in the opposite direction that is the left direction.

However, as shown in FIG. 1B, when the contact part 153a is separated from the first body part 110 or the second body part 130, even when the second body part 130 moves to the right, the phenomenon that the contact part 153a is stuck between the first body part 110 and the second body part 130 does not occur, and thus the second body part 130 may freely move to the right.

In the structure as shown in FIGS. 1A and 2, as the elastic member 153b pushes the contact part 153a, the contact part 153a may be able to simultaneously contact the first body part 110 and the second body part 130.

In the following description, a modification of the embodiment is described in detail.

Referring to FIG. 3, in the left side (based on FIG. 3) with respect to the center portion of the first body part 110, the inner surface of the first body part 110 facing the upper surface of the second body part 130 (based on FIG. 3) may have an inclined surface that is inclined to the lower left.

In the right (based on FIG. 3) with respect to the center portion of the first body part 110, the inner surface of the first body part 110 facing the upper surface of the second body part 130 (based on FIG. 3) may have an inclined surface that is inclined downward toward the right.

Accordingly, the interval between the first body part 110 and the second body part 130 decreases in the outward direction with respect to the center portion of the first body part 110 (based on FIG. 3).

When the locking unit 150 moving between the first body part 110 and the second body part 130 moves in the outward direction with respect to the center portion of the first body part 110, the locking unit 150 simultaneously contacts the first body part 110 and the second body part 130, and thus in the same principle as the description in FIG. 2, being stuck phenomenon of the contact part 153a is generated in both outward directions so that a relative movement of the second body part 130 with respect to the first body part 110 may be prevented in both horizontal directions, thereby entering the locking state.

In other words, when a locking unit 150A simultaneously contacts the first body part 110 and the second body part 130 in the left side with respect to the center portion, the second body part 130 may be prevented from moving from the right to the left.

When a locking unit 150B0 simultaneously contacts the first body part 110 and the second body part 130 in the right side with respect to the center portion, the second body part 130 may be prevented from relatively moving in both directions from the left to the right.

Accordingly, when the locking units 150A and 150B that is disposed in both sides of the first body part 110 with respect to the center portion simultaneously contacts the first body part 110 and the second body part 130, the movement of the second body part 130 from the right to the left is prevented in the left side with respect to the center portion of the first body part 110, and simultaneously the movement of the second body part 130 from the left to the right is prevented in the right side with respect to the center portion of the first body part 110. As a result, the second body part 130 may be prevented from moving in both directions with respect to the first body part 110 (based on the horizontal direction in FIG. 3).

Referring to FIG. 3, the first body part 110 according to a modification of the embodiment has an inclined surface that is inclined downward and outward with respect to the center portion, but the disclosure is not limited thereto and the inclined surface may be inclined downward toward the inside with respect to the center portion, that is, upward and outward with respect to the center portion.

Although it is not illustrated in the drawings, in this state, an interval between the inner surface of the first body part 110 and the outer surface of the second body part 130, which face each other, decreases from the outside to the inside with respect to the center portion of the first body part 110.

Accordingly, the locking units 150A and 150B moving between the first body part 110 and the second body part 130 may simultaneously contact the first body part 110 and the second body part 130 when moving toward the inside with respect to the center portion of the first body part 110.

Accordingly, the relative movement of the second body part 130 with respect to the first body part 110 may be prevented, thereby entering the locking state. In this state, a direction in which the elastic member 153*b* pushes the contact part 153*a* may be a direction from the outside to the inside.

Referring to FIG. 3, the locking units 150A and 150B according to a modification of the embodiment may move between the first body part 110 and the second body part 130 and include support parts 151A and 151B and locking main body parts 153A and 153B.

The support parts 151A and 151B are fixedly coupled to the first body part 110 by using a fastening member such as a bolt in the disclosure. However, the disclosure is not limited thereto, and the support parts 151A and 151B may be integrally formed with the first body part 110. Referring to FIG. 3, the support parts 151A and 151B are provided at the center portion of the first body part 110, and the locking main body parts 153A and 153B that are described later are respectively coupled to both sides of the support parts 151A and 151B.

Referring to FIG. 3, various modifications of the embodiments are possible such as the support parts 151A and 151B each may be provided as a plurality of support parts to correspond to the locking main body parts 153A and 153B that are plurally provided, or as a single member to be coupled to each of the locking main body parts 153A and 153B at both sides. In this state, the support parts 151A and 151B are coupled to the locking main body parts 153A and 153B arranged at the left and right sides with respect to the center portion of the first body part 110.

Referring to FIG. 3, the locking main body parts 153A and 153B according to a modification of the embodiment are connected to the support parts 151A and 151B to be capable of moving between the first body part 110 and the second body part 130 and may respectively include contact parts 153Aa and 153Ba and elastic members 153Ab and 153Bb.

Referring to FIG. 3, the locking main body parts 153A and 153B according to a modification of the embodiment each may include a plurality of locking main body parts and may be respectively arranged at both sides of the support parts 151A and 151B, and the locking main body parts 153A and 153B that are plural may move in the opposite directions.

Accordingly, in the left side with respect to the center portion of the first body part 110, the locking main body part 153A moves in a direction away from the support part 151A to simultaneously contact the first body part 110 and the second body part 130, which face each other.

In the right side with respect to the center portion of the first body part 110, the locking main body part 153B moves in a direction away from the support part 151B to simultaneously contact the first body part 110 and the second body part 130, which face each other.

Additionally, in the left side with respect to the center portion of the first body part 110 where the support parts 151A and 151B are disposed, a frictional force due to being stuck between the locking unit 150A and each of the first body part 110 and the second body part 130 is generated, and thus the relative movement of the second body part 130 with respect to the first body part 110 may be prevented from the right to the left.

In the right side with respect to the center portion of the first body part 110, in the same principle, the relative movement of the second body part 130 with respect to the first body part 110 may be prevented from the left to the right, and thus the second body part 130 is prevented from moving in both directions with respect to the first body part 110.

Referring to FIG. 3, the contact parts 153Aa and 153Ba are disposed between the first body part 110 and the second body part 130 to be capable of moving between the first body part 110 and the second body part 130. The contact parts 153Aa and 153B a contact the elastic members 153Ab and 153Bb that are described later, and may be moved between the first body part 110 and the second body part 130 due to the elastic resilience of the elastic members 153Ab and 153Bb.

Referring to FIG. 3, the contact parts 153Aa and 153Ba according to a modification of the embodiment may have a ball or cylindrical shape to be capable of point contact or line contact with each of the first body part 110 and the second body part 130.

When the contact parts 153Aa and 153Ba are formed in a cylindrical shape, the locking unit 150, particularly the locking main body parts 153A and 153B, moving between the first body part 110 and the second body part 130, simultaneously contacts the first body part 110 and the second body part 130 which face each other, and thus the contact parts 153Aa and 153Ba has a line contact with each of the first body part 110 and the second body part 130. Accordingly, compared with a case in which the contact parts 153Aa and 153Ba has a point contact with the first body part 110 and the second body part 130, a contact portion increases and the increase of the contact portion means an increase of a friction portion. The increase of the friction portion improves locking performance by preventing the relative movement of the second body part 130 with respect to the first body part 110.

In the disclosure, although the contact parts 153Aa and 153Ba each have a cylindrical shape by extending in a length direction of a center axis, various modifications of the embodiments are possible such that the contact parts 153Aa and 153Ba each have a ball shape to have a point contact with each of the first body part 110 and the second body part 130, which face each other.

Referring to FIG. 4, a first straight line L11 perpendicular to the first body part 110 at the center of the contact parts 153Aa and 153Ba according to a modification of the embodiment and a second straight line L12 perpendicular to the second body part 130 at the center of the contact parts 153Aa and 153Ba form a certain angle α.

In detail, as the first straight line L11 and the second straight line L12 form the angle α, not 180 degrees, one surface of the first body part 110 and one surface of the second body part 130, which face each other, are not parallel to each other, and as shown in FIG. 4, the interval between the first body part 110 and the second body part 130, which face each other, may decrease in the outward direction from the center portion.

Referring to FIG. 3, the elastic members 153Ab and 153Bb according to a modification of the embodiment are disposed between the contact parts 153Aa and 153Ba and the support parts 151A and 151B and respectively connected to the contact parts 153Aa and 153Ba and the support parts 151A and 151B. The elastic members 153Ab and 153Bb each include a spring having a coil shape and exhibit elastic resilience.

Referring to FIG. 3, the elastic members 153Ab and 153Bb may be provided at both sides of the support parts 151A and 151B disposed at the center portion of the first body part 110. Various modified embodiments are possible such that the elastic members 153Ab and 153Bb respectively contact the contact parts 153Aa and 153Ba disposed at both sides with respect to the center portion of the first body part 110, or are integrally formed with the support parts 151A and 151B to respectively penetrate the support parts 151A and 151B and contact the contact parts 153Aa and 153Ba.

Referring to FIG. 3, the elastic members 153Ab and 153Bb each may have elastic resilience in a direction in which the interval between one surface of the first body part 110 and one surface of the second body part 130, which face each other, decreases in a certain section. In detail, an elastic member 153Bb pushes a contact part 153Ba to move from the left to the right in the right side with respect to the center portion of the first body part 110. In this state, the elastic member 153Bb may have elastic resilience in a direction from the left to the right.

Likewise, the elastic member 153Bb pushes a contact part 153Aa to move from the right to the left (based on FIG. 3) in the left side with respect to the center portion of the first body part 110. In this state, an elastic member 153Ab may have elastic resilience in a direction from the right to the left.

In other words, the elastic members 153Ab and 153Bb may be compression springs that resist compression.

The elastic members 153Ab and 153Bb may have elastic resilience in a direction in which the contact parts 153Aa and 153Ba are pushed in a direction away from the support parts 151A and 151B. In other words, when one surface of the first body part 110 facing the second body part 130 is inclined downward and outward with respect to the center portion, the elastic members 153Ab and 153Bb may move in a direction in which the contact parts 153Aa and 153Ba are away from the support parts 151A and 151B to simultaneously contact the first body part 110 and the second body part 130.

Accordingly, when the elastic members 153Ab and 153Bb respectively push the contact parts 153Aa and 153Ba disposed at both sides with respect to the center portion of the first body part 110, each of the contact parts 153Aa and 153Ba simultaneously contacts the first body part 110 and the second body part 130, which face each other, and the friction and the being stuck generated as the second body part 130 and the first body part 110 contact each other may prevent the movement of the second body part 130 relative to the first body part 110.

However, the disclosure is not limited thereto, and various modifications of the embodiments are possible such that, as the interval between the first body part 110 and the second body part 130, which face each other, decreases in a direction from the outside to the inside toward the center portion of the first body part 110, the elastic members 153Ab and 153Bb pulls the contact part 153Aa to move the contact part 153Aa in the direction from the left to the right the contact part 153Aa in the left side with respect to the center portion of the first body part 110, and in this state, the elastic member 153Ab has elastic resilience in a direction from the left to the right.

In this case, when one surface of the first body part 110 facing the second body part 130 is inclined upward and outward with respect to the center portion, the contact parts 153Aa and 153Ba are moved by the elastic members 153Ab and 153Bb in a direction (from the right to the left) approaching the support parts 151A and 151B to directly contact the first body part 110 and the second body part 130, thereby preventing the relative movement of the second body part 130 to the first body part 110.

Furthermore, various modifications of the embodiments are possible such that, when the support parts 151A and 151B are independently disposed to face each other and one surface of the first body part 110 is inclined upward and outward with respect to the center portion, the elastic member 153Aa and 153Bb respectively connected to the support parts 151A and 151B push the contact parts 153Aa and 153Ba, respectively, from the outside to the inside (that is, toward the center portion of the first body part 110).

Referring to FIGS. 3 to 5, unlocking units 160A and 160B according to a modification of the embodiment may push the locking units 150A and 150B. Particularly, unlocking units 160A and 160B may be disposed on a movement path of the contact parts 153Aa and 153Ba to push the contact parts 153Aa and 153Ba in a direction in which the interval between the respective surfaces of the first body part 110 and the second body part 130, which face each other, increases. In this state, the unlocking units 160A and 160B may be connected to the first body part 110 or to an external separate member.

Referring to FIGS. 3 to 5, the unlocking units 160A and 160B push the locking unit 150 in a direction toward the center portion of the first body part 110. The interval between one surface of the first body part 110 and one surface of the second body part 130, which face each other, may decrease in the outward direction with respect to the center portion of the first body part 110.

The locking unit 150, particularly the contact parts 153Aa and 153Ba, move in the outward direction with respect to the center portion of the first body part 110, and when the contact parts 153Aa and 153Ba simultaneously contact the first body part 110 and the second body part 130, a frictional force is generated so that the relative movement of the second body part 130 with respect to the first body part 110 may be prevented.

The unlocking units 160A and 160B according to a modification of the embodiment may push the contact parts 153Aa and 153Ba that simultaneously contact the first body part 110 and the second body part 130, which face each other, due to the elastic resilience of the elastic members 153Ab and 153Bb the direction toward the center portion of the first body part 110, that is, in a direction in which the interval between the first body part 110 and the second body part 130, which face each other, increases.

As the unlocking units 160A and 160B push the contact parts 153Aa and 153Ba toward the center portion of the first body part 110, the locking state in which a relative movement of the second body part 130 with respect to the first body part 110 is prevented is released, and thus the second body part 130 may move relative to the first body part 110.

Although it is not illustrated in the drawings, a modified embodiment is possible such that, when the first body part 110 facing the second body part 130 extending in the horizontal direction has a surface inclined upward and outward with respect to the center portion, and the interval between the first body part 110 and the second body part 130, which face each other, increases outward from the center portion of the first body part 110, the unlocking units 160A and 160B may push the contact parts 153Aa and 153Ba outward from the center portion of the first body part 110.

Referring to FIGS. 3 to 5, the unlocking units 160A and 160B according to an embodiment may be coupled to the first body part 110 to be capable of rotating clockwise or counterclockwise. In this state, the unlocking units 160A and 160B may include unlocking main bodies 161A and 161B and an unlocking pin portion 165.

Referring to FIG. 3, the unlocking main bodies 161A and 161B are rotatably coupled to the first body part 110 and may rotate clockwise or counterclockwise around the unlocking pin portion 165 that is described later, as a rotation center.

Bent portions 163A and 163B may protrude toward the locking unit 150 respectively from one end portions of the unlocking units 160A and 160B, particularly the unlocking main bodies 161A and 161B, facing the locking unit 150, particularly the contact parts 153Aa and 153Ba.

As such, as the bent parts 163A and 163B protrude, when the unlocking units 160A and 160B push the contact parts 153Aa and 153Ba, the bent parts 163A and 163B formed on the unlocking main bodies 161A and 161B and the contact parts 153Aa and 153Ba contact each other at one or more points. Accordingly, when the bent parts 163A and 163B push the contact parts 153Aa and 153Ba in a direction in which the interval between one surface of the first body part 110 and one surface of the second body part 130, which face each other, increases, movement stability of the contact parts 153Aa and 153Ba may be improved.

Referring to FIGS. 3 to 5, the unlocking units 160A and 160B according to a modification of the embodiment may respectively push the locking units 150A and 150B, particularly the contact parts 153Aa and 153Ba, disposed at both sides with respect to the center portion of the first body part 110.

In a modification of the embodiment, the unlocking units 160A and 160B may rotate in different directions around the unlocking pin portion 165 as the same rotation center, but the disclosure is not limited thereto, and various modifications of the embodiments are possible such that the unlocking units 160A and 160B may rotate around different rotation centers or may linearly reciprocate.

Referring to FIG. 5, a first unlocking unit 160A pushes the contact part 153Aa disposed in the left side with respect to the center portion of the first body part 110, and in the locking apparatus 100 according to a modification of the embodiment, to release the locking state, the first unlocking unit 160A may rotate counterclockwise around the unlocking pin portion 165 as the rotation center.

As the first unlocking unit 160A rotates counterclockwise, the contact part 153Aa is pushed toward the center portion of the first body part 110. A second unlocking unit 160B having the same rotation center as same the first unlocking unit 160A and rotating clockwise in the opposite direction to that of the first unlocking unit 160A pushes the contact part 153Ba toward the center portion of the first body part 110.

Then, as the unlocking units 160A and 160B separate the contact parts 153Aa and 153Ba, which are disposed at both sides with respect to the center portion of the first body part 110, from the first body part 110 and the second body part 130, the locking state of the locking apparatus 100 may be released.

Although it is not illustrated in the drawings, the first and second unlocking units 160A and 160B are rotatably coupled to the first body part 110 by means of a separate connection member such as a lever, to simultaneously push the contact parts 153Aa and 153Ba disposed at both sides of the first body part 110 toward the center portion of the first body part 110, particularly in a direction in which the interval between the first body part 110 and the second body part 130, which face each other, increases.

Referring to FIG. 5, when the contact parts 153Aa and 153Ba according to a modification of the embodiment move toward the center portion of the first body part 110, that is, toward the support parts 151A and 151B, the elastic members 153Ab and 153Bb are each compressed, and the elastic members 153Ab and 153Bb may each have elastic resilience to push the contact parts 153Aa and 153Ba in a direction away from the support parts 151A and 151B.

When the unlocking units 160A and 160B are separated from the contact parts 153Aa and 153Ba, the contact parts 153Aa and 153Ba are respectively moved by the elastic members 153Ab and 153Bb outward with respect to the support parts 151A and 151B that are the center portion of the first body part 110. Then, as the interval between one surface of the first body part 110 and one surface of the second body part 130, which face each other, decreases outward, the contact parts 153Aa and 153Ba start to simultaneously contact the first body part 110 and the second body part 130 at a certain position, and Accordingly, the locking state in which the relative movement of the second body part 130 with respect to the first body part 110 is prevented may be established.

Referring to FIGS. 3 to 5, a rotation guide portion 113 through which the unlocking units 160A and 160B penetrates may be formed in an upper surface of the first body part 110 according to a modification of the embodiment. Due to the rotation guide portion 113, when the first and second unlocking units 160A and 160B rotate clockwise or counterclockwise to be away from the contact parts 153Aa and 153Ba, the first and second unlocking units 160A and 160B are prevented from further rotating over a certain angle by being supported on the first body part 110, thereby restricting a turning radius of the unlocking units 160A and 160B.

<Locking Apparatus According to Another Embodiment>

Figure 6:
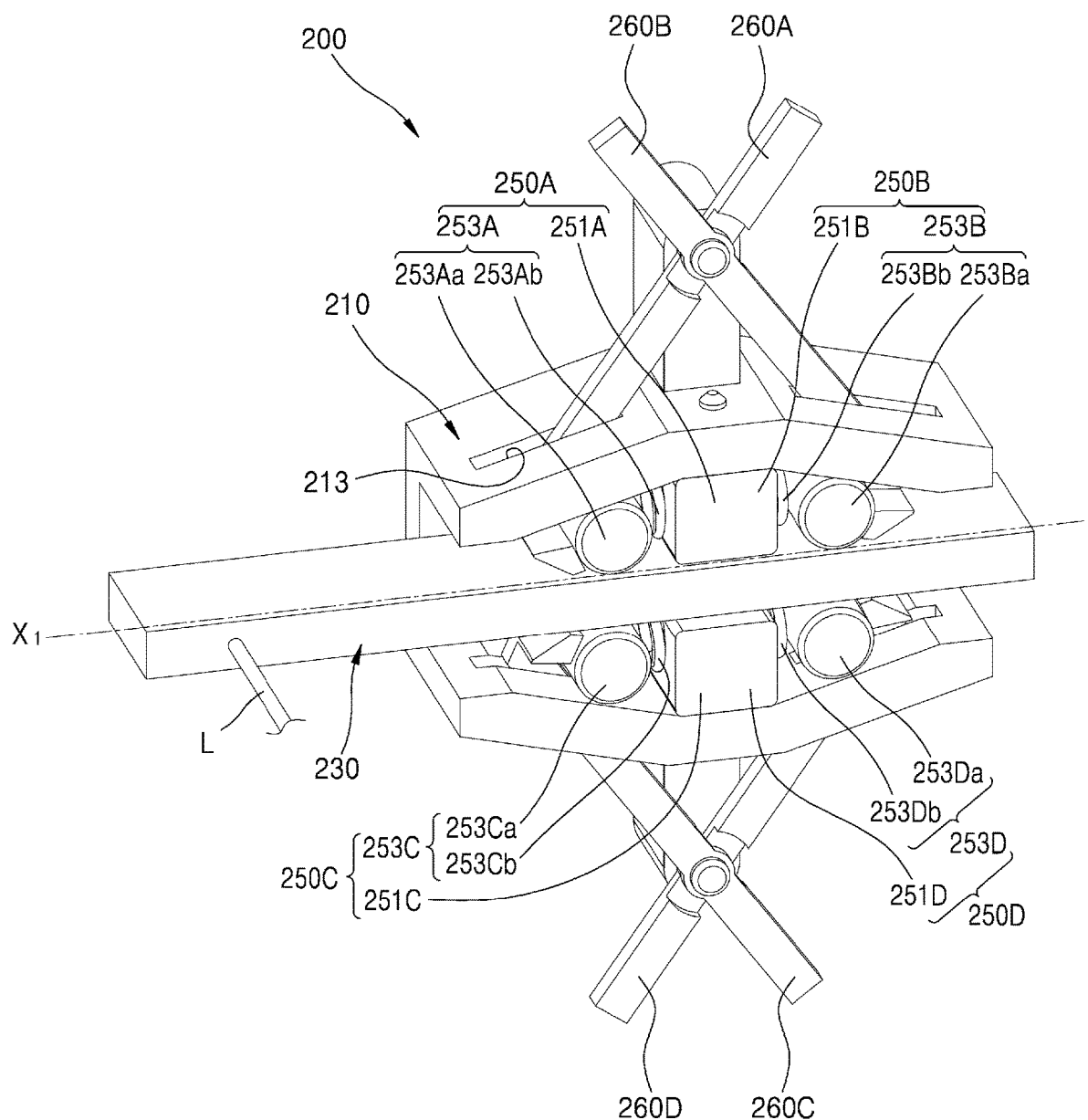
FIG. 6 is a side view of a locking apparatus according to another embodiment.

A locking apparatus according to another embodiment is described below with reference to the accompanying drawings. FIG. 6 is a side view of a locking apparatus according to another embodiment.

Referring to FIG. 6, a locking apparatus 200 according to another embodiment may include a first body part 210, a second body part 230, a locking unit 250, and an unlocking unit 260.

Referring to FIG. 6, in the locking apparatus 200 according to another embodiment, the locking unit 250 may include a first locking unit 250A disposed in the left side (based on FIG. 6) and a second locking unit 250B disposed in the right side (based on FIG. 6) with respect to the center portion of the first body part 210 in an upper side with respect to a movement axis $X_1$ of the second body part 230, and a third locking unit 250C disposed in the left side (based on FIG. 6) and a fourth locking unit 250D in the right side (based on FIG. 6) with respect to the center portion of the first body part 210 in a lower portion with respect to the movement axis $X_1$ of the second body part 230.

Referring to FIG. 6, in the locking apparatus 200 according to another embodiment, the unlocking unit 260 may include a first unlocking unit 260A disposed in the left side (based on FIG. 6) and pushing the first locking unit 250A and an unlocking unit 260B disposed in the right side (based on FIG. 6) and pushing the second locking unit 250B with respect to the center portion of the first body part 210 in an upper side with respect to the movement axis $X_1$ of the second body part 230, and a third unlocking unit 260C disposed in the left side (based on FIG. 6) and pushing the third locking unit 250C and a fourth unlocking unit 260D disposed in the right side (based on FIG. 6) and pushing the fourth locking unit 250D with respect to the center portion of the first body part 210 in a lower side with respect to the movement axis $X_1$ of the second body part 230.

A movement path may be formed in the first body part 210 so that the second body part 230 is movable in the movement path. In this state, the movement path may be formed in the first body part 210 in a groove shape, particularly between inner surfaces of the first body part 210 which face each other.

Referring to FIG. 6, the first body part 210 according to another embodiment forms an axial symmetry with respect to the movement axis $X_1$ of the second body part 230.

The second body part 230 moves in the horizontal direction (based on FIG. 6) between the inner surfaces of the first body part 210, thereby being capable of moving relative to the first body part 210. Although it is not illustrated in the drawings, the connection member L such as a wire may be connected to the second body part 230, and such a connection member may be connected to a part capable of linear motion and rotational motion in equipment such as the surgical instruments 1 and 2 that are described later.

Referring to FIG. 6, the second body part 230 is disposed on the movement path formed in the first body part 210 and moves in the horizontal direction (based on FIG. 6) along the movement axis $X_1$.

Comparing with the locking apparatus 100 according to an embodiment, in the locking apparatus 200 according to another embodiment, the inner surfaces of the first body part 210, which face each other and forming the movement path, are symmetrically arranged with respect to the movement axis $X_1$, and the inner surfaces of the first body part 210, which face each other, do not directly contact the second body part 230 not only in the upper side, but also in the lower side of the second body part 230.

Accordingly, referring to FIG. 6, the first and second locking units 250A and 250B are disposed between an upper surface of the second body part 230 and the inner surface of the first body part 210, and the third and fourth locking units 250C and 250D are disposed between a lower surface of the second body part 230 and the inner surface of the first body part 210.

Referring to FIG. 6, an interval between an upper inner surface of the first body part 210 and the upper surface of the second body part 230, which face each other, and an interval between a lower inner surface of the first body part 210 and the lower surface of the second body part 230, which face each other, may each decrease in one direction with respect to the center portion of the first body part 210.

In other words, according to another embodiment, an interval between the upper surface or the lower surface (based on FIG. 6) of the second body part 230 and the inner surface of the first body part 210, which face each other, may decrease outward with respect to the center portion of the first body part 210.

However, the disclosure is not limited thereto, and in the locking apparatus 100 according to an embodiment, as described above, various modifications of the embodiments are possible such that an interval between the first body part 210 and the second body part 230 increases outward with respect to the center portion of the first body part 210.

Referring to FIG. 6, in the locking apparatus 200 according to another embodiment, the upper and lower sides (based on FIG. 6) may be symmetric with respect to the movement axis X1 of the second body part 230.

The locking units 250A, 250B, 250C, and 250D are provided between the first body part 210 and the second body part 230 in the upper side and between the first body part 210 and the second body part 230 in the lower side with respect to the second body part 230. Accordingly, a phenomenon of being stuck is simultaneously generated in the locking units, and thus a frictional force is increased so that locking performance may be improved.

In the locking apparatus 200 according to another embodiment, except that the locking units 250A, 250B, 250C, and 250D are respectively and symmetrically disposed between the inner surfaces of the first body part 210 that are symmetrically with respect to the movement axis $X_1$ of the second body part 230, and that the locking units 250A, 250B, 250C, and 250D increase frictional forces by simultaneously contacting the first body part 210 and the second body part 230, the locking units 250A, 250B, 250C, and 250D, the detailed structures of the unlocking units 260A, 260D, 260C, and 260D are substantially the same as those of the locking unit 150 and the unlocking unit 160 in the locking apparatus 100 according to an embodiment, and thus redundant descriptions thereof are omitted.

Additionally, in the locking apparatus 200 according to another embodiment, as the locking units 250A, 250B, 250C, and 250D, and the unlocking units 260A, 260D, 260C, and 260D, are plurally disposed in both of the left and right sides (based on FIG. 6) with respect to the center portion of the first body part 210, a locking state in which the second body part 230 is prevented from moving in both directions relative to the first body part 210 may be established.

However, the disclosure is not limited thereto, and a modification of an embodiment is possible such that, as the locking unit and the unlocking unit are disposed only in one side of the left and right sides of the first body part 210, the relative movement of the second body part 230 with respect to the first body part 210 in one direction may be prevented.

<Locking Apparatus According to Another Embodiment>

A locking apparatus according to another embodiment is described below with reference to the accompanying drawings.

Figure 7:
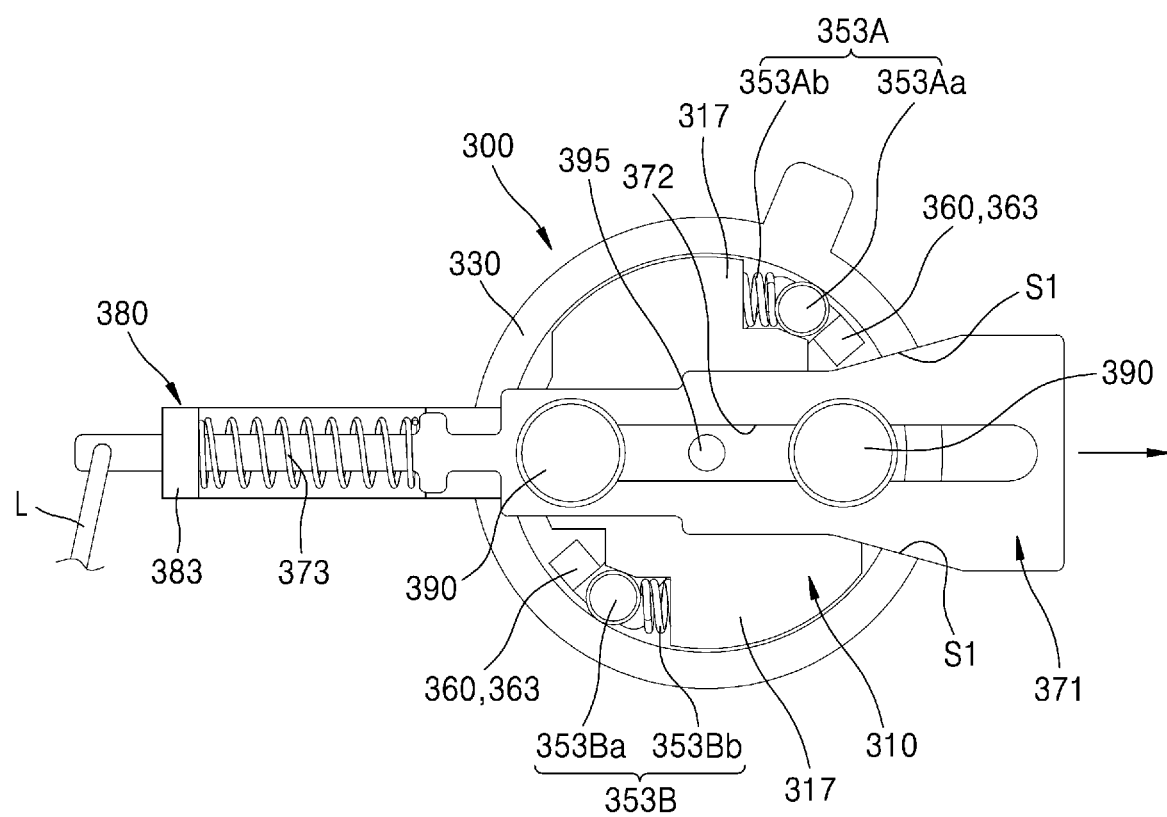
FIGS. 7 and 8 are side views of a locking apparatus according to another embodiment.
Figure 8:
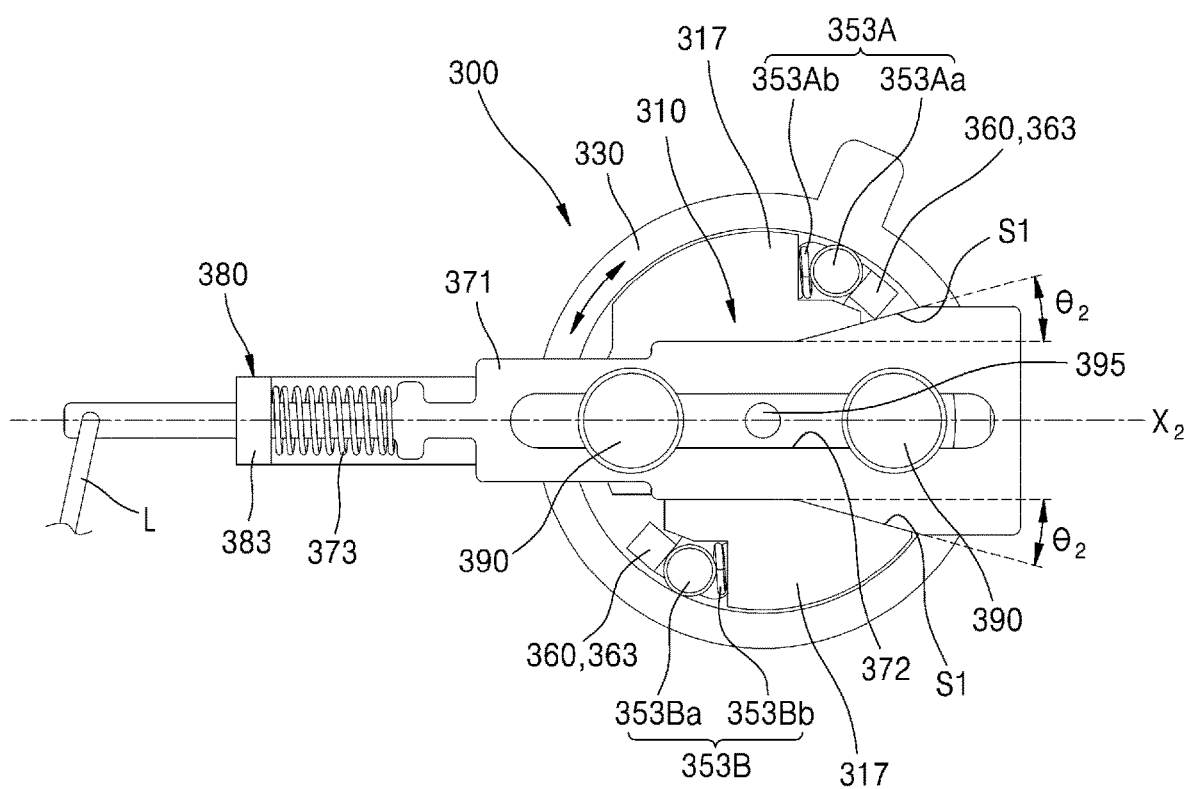
Figure 9A:
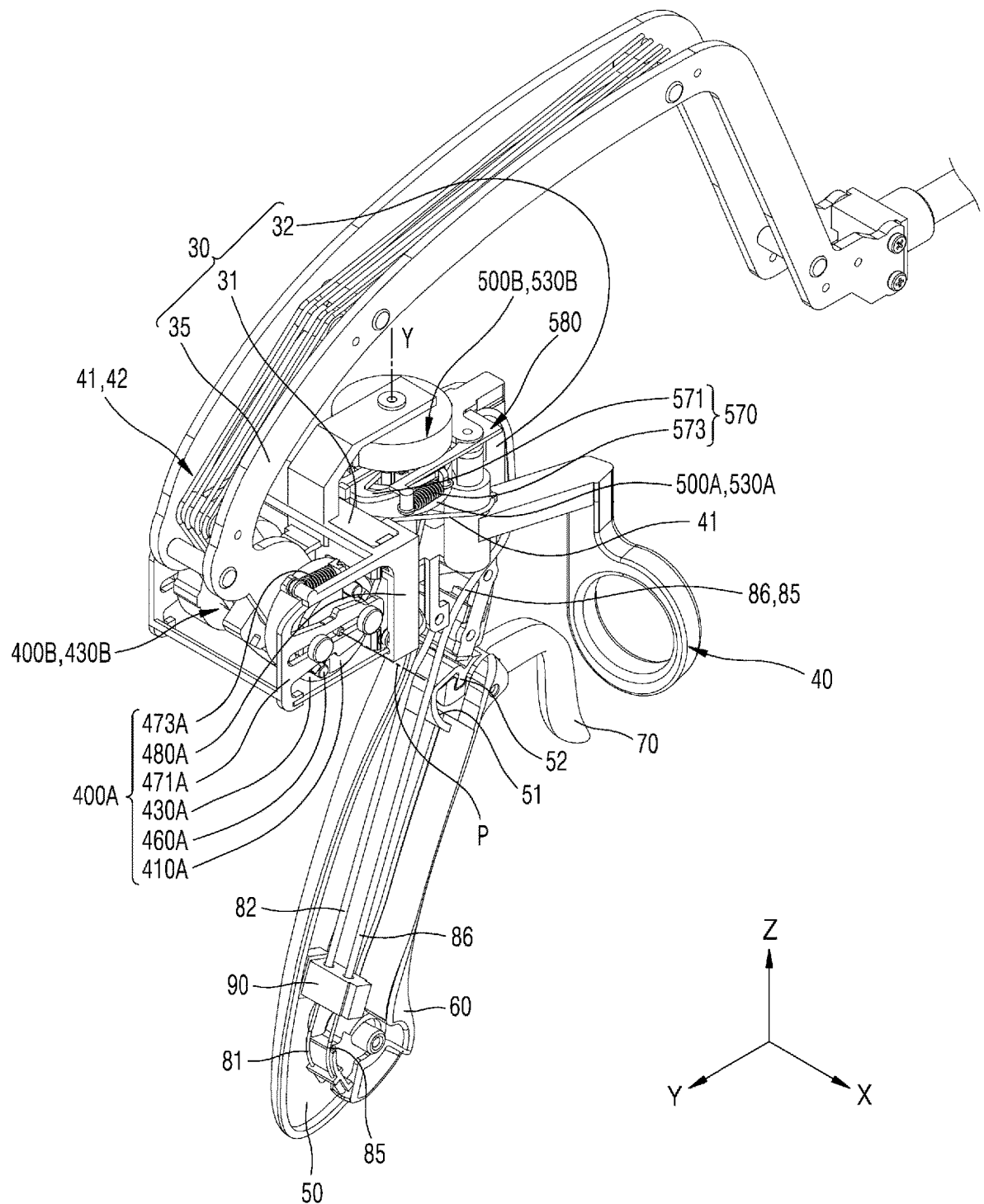
FIGS. 9A and 9B are perspective views of a surgical instrument provided with the locking apparatus according to another embodiment.
Figure 9B:
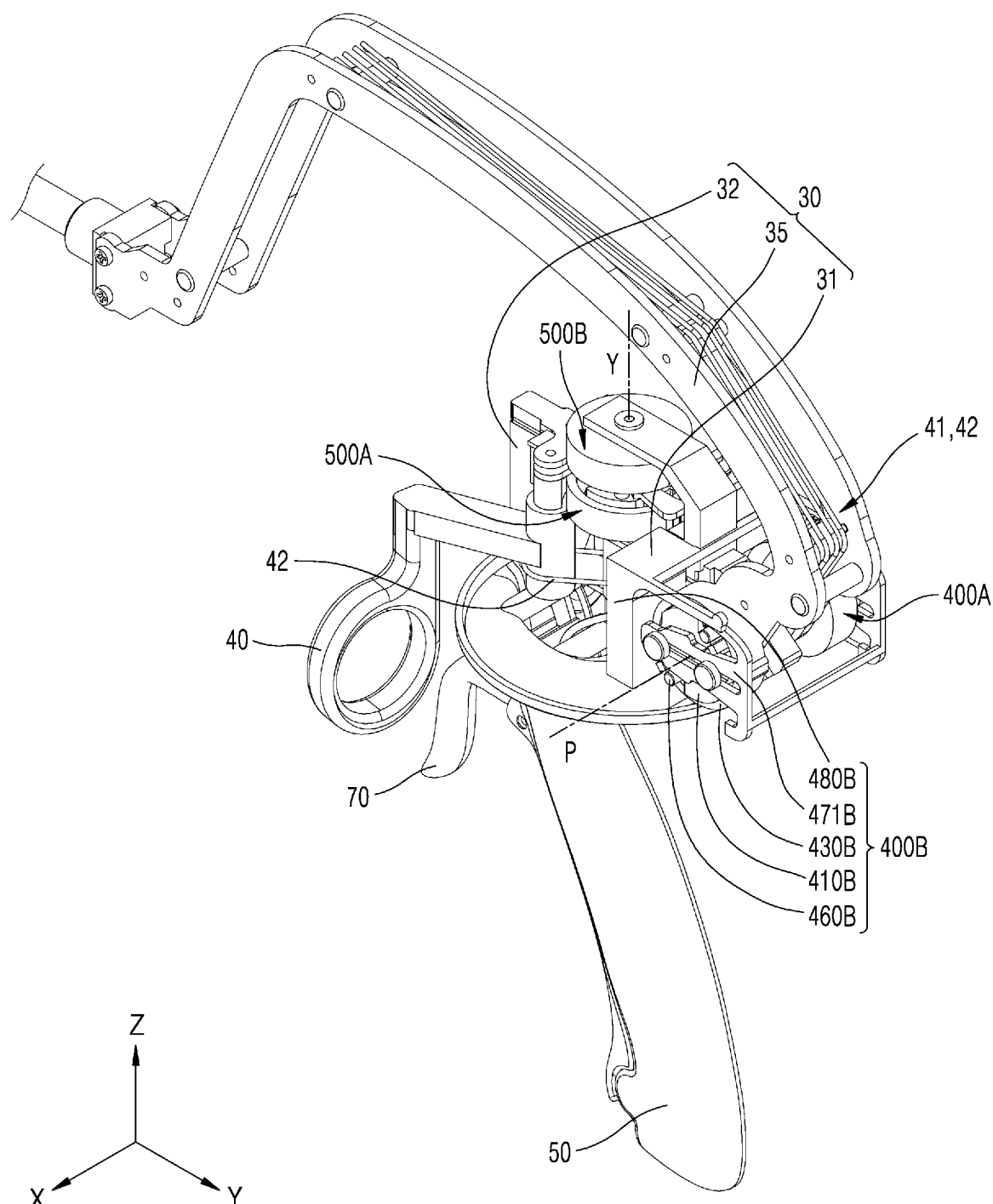

FIGS. 7 and 8 are side views of a locking apparatus according to another embodiment. FIGS. 9A and 9B are perspective views of a surgical instrument provided with the locking apparatus according to another embodiment.

A locking apparatus 300 according to another embodiment may include a first body part 310, a second body part 330, a locking unit 350, an unlocking unit 360, a pushing plate part 370, a base part 380, a guide member 390, and a locking apparatus rotation axis part 395.

In the locking apparatus 300 according to another embodiment, the locking unit 350 denotes locking main body parts 353A and 353B. Referring to FIGS. 7 and 8, in the locking apparatus 300 according to another embodiment, the locking unit 350 may include two locking units.

Figure 17A:
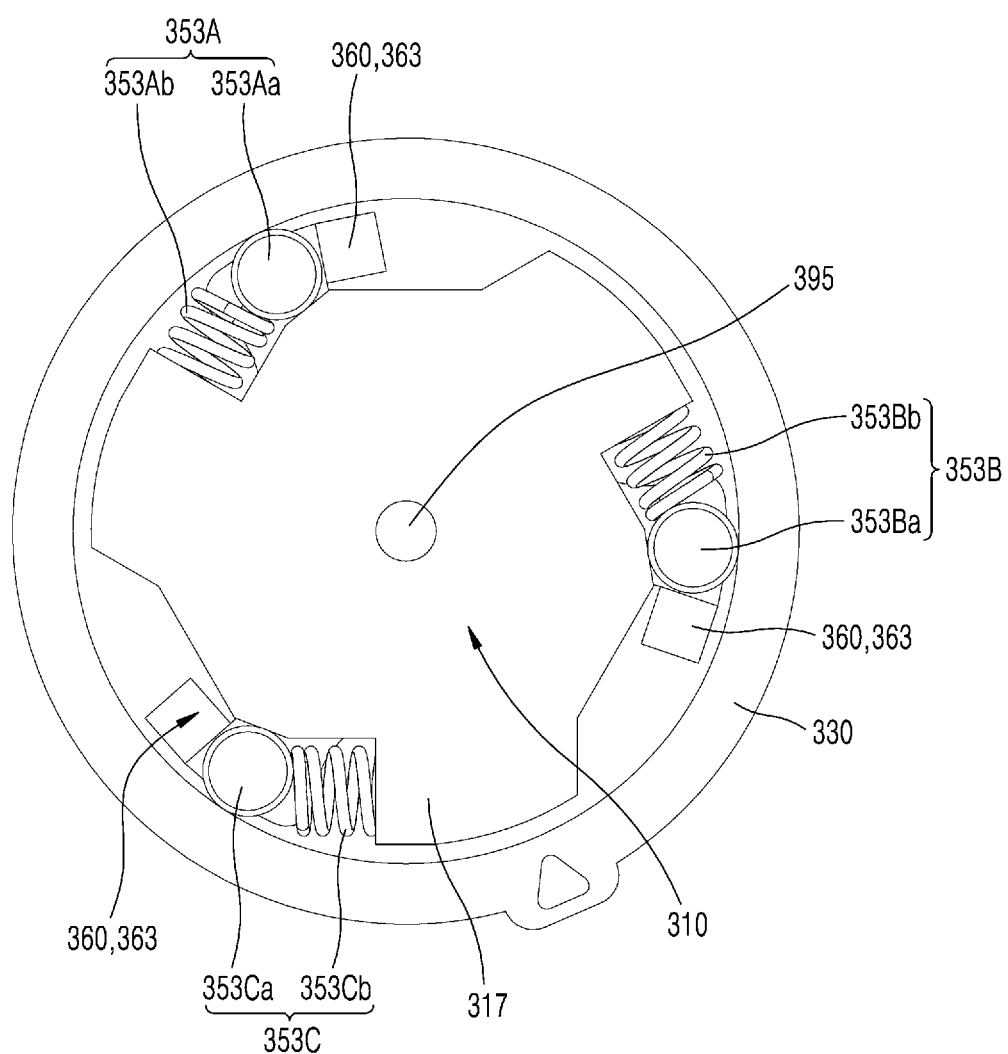
FIGS. 17A and 17B illustrate a locking unit according to another embodiment.

However, the disclosure is not limited thereto, and various modifications of the embodiments are possible such that, as shown in FIG. 17A, three locking units 350A, 350B, and 350C, that is, three locking main body parts 353A, 353B, and 353C, are disposed along a rotational direction of the second body part 330, or n-number of locking units, where n is an integer exceeding 3, may be formed as the locking units 350.

Referring to FIG. 17A, as the number of the locking units 350 increases, the locking main body parts 353A, 353B, and 353C, particularly contact parts 353Aa, 353Ba, and 353Ca, move in a direction in which an interval between the first body part 310 and the second body part 330 decreases, so as to be stuck by respectively contacting the respective surfaces of the first body part 310 and the second body part 330, which face each other. Accordingly, as a frictional force increases, the locking performance may be improved.

Referring back to FIGS. 7 and 8, a movement path, along which the second body part 330 is movable, may be formed in the first body part 310 according to another embodiment. The movement path may be formed outside the first body part 310, and the locking main body parts 353A and 353B is movable along one surface forming the outside of the first body part 310.

Referring to FIGS. 7 and 8, the second body part 330 according to another embodiment has a hollow space therein, and the first body part 310 may be disposed inside the second body part 330.

The second body part 330 is coaxially with the first body part 310, and may be disposed to be rotatable outside the first body part 310. In other words, the second body part 330 may be disposed to be rotatable around the same rotation axis with the first body part 310. In detail, the second body part 330 according to another embodiment has a cylindrical shape having a constant radius, a constant radius of curvature, and a hollow space therein.

Although it is not illustrated in the drawings, the second body part 330 may be connected to a movable portion, for example, the connection member L such as a wire, in a separate apparatus, such as the surgical instruments 1 and 2, where the locking apparatus 300 is installed.

The first body part 310, the unlocking unit 360, and the locking main body parts 353A and 353B may be disposed inside the second body part 330 according to another embodiment. Accordingly, when the second body part 330 rotates outside the first body part 310, a certain apparatus connected to the second body part 330 is capable of rotational motion or linear motion with the second body part 330.

Furthermore, in a locking state in which the second body part 330 is prevented from moving related to the first body part 310 by the locking main body parts 353A and 353B, a linear or rotational motion of the portion connected to the second body part 330 may be prevented.

In a certain section, an interval between one surface of the first body part 310 and one surface of the second body part 330, which face each other, may decrease in a clockwise or counterclockwise direction around the locking apparatus rotation axis part 395 that is the rotation center of the first body part 310, as a rotation center.

As the interval between one surface of the first body part 310 (outer circumferential surface) and one surface of the second body part 330 (inner circumferential surface) decreases, when the locking main body parts 353A and 353B simultaneously contact the first body part 310 and the second body part 330, the second body part 330 may be prevented from moving in any one direction relative to the first body part 310.

Referring to FIGS. 7 and 8, the interval between one surface of the first body part 310 and one surface of the second body part 330 according to another embodiment may decrease in a clockwise with respect to the center of the first body part 310.

Accordingly, as the locking main body parts 353A and 353B move in the clockwise direction to simultaneously contact the first body part 310 and the second body part 330 therebetween, a locking state may be established, in which the clockwise (based on FIG. 7) movement of the second body part 330, that is, the movement of the second body part 330 relative to the first body part 310 in one direction (clockwise) may be prevented.

Referring to FIGS. 7 and 8, although the movement of the second body part 330 relative to the first body part 310 in the clockwise direction (based on FIG. 7) is prevented, the disclosure is not limited thereto, and a modification of an embodiment may be possible such that the interval between one surface of the first body part 310 and one surface of the second body part 330 decreases in the counterclockwise direction with respect to the center of the first body part 310.

As the interval between one surface of the first body part 310 and one surface of the second body part 330 decreases in the counterclockwise direction, the locking main body parts 353A and 353B move in the counterclockwise direction to simultaneously contact the first body part 310 and the second body part 330 therebetween, the movement of the second body part 330 in the counterclockwise direction, that is, a locking state may be established, in which the second body part 330 is prevented from moving in one direction (counterclockwise direction) relative to the first body part 310.

Referring to FIGS. 9A and 9B, as locking apparatuses 400A and 500A in which an interval between one surface of each of the first body parts 410A and 410B and one surface of each of the second body parts 430A and 430B decreases in the clockwise (based on FIG. 9A), and locking apparatuses 400B and 500B disposed to face the locking apparatuses 400A and 500A, are respectively coupled to each other, the surgical instrument 1 in which the locking apparatuses 400A, 400B, 500A, and 500B are installed enters a locking state. In other words, with respect to the centers of first body parts 410A, 410B, 510A, and 510B, relative movements of the second body parts 430A, 430B, 530A, and 530B and a certain member connected to each of the second body parts 430A, 430B, 530A, and 530B to the first body parts 410A, 410B, 510A, and 510B in the clockwise and counterclockwise directions may be prevented.

Referring to FIGS. 9A and 9B, the locking apparatuses 400A and 400B, in which the interval between one surface of each of the first body parts 410A and 410B and one surface of each of the second body parts 430A and 430B decreases in the clockwise direction, are provided on the same pitch axis forming a surface symmetry with respect to a plane (based on a Y-Z plane of FIG. 9A) that is perpendicular to the pitch axis.

Also, the locking apparatuses 500A and 500B, in which an interval between one surface of each of the first body parts 510A and 510B and one surface of each of the second body parts 530A and 530B decrease in the clockwise direction, are provided on the same yaw axis forming a surface symmetry with respect to a plane (based on a X-Y plane of FIG. 9A) that is perpendicular to the yaw axis.

Accordingly, in the locking state of the surgical instrument 1 according to an embodiment of the present disclosure, in which the locking apparatuses 400A, 400B, 500A, and 500B according to the embodiments are installed, a relative movement of a portion (based on a bent part 35 of FIG. 9A) that is simultaneously connected to each of the second body parts 430A and 430B to a portion (based on a pitch manipulation part 31 of FIG. 9A) that is simultaneously connected to each of the first body parts 410A and 410B, in the clockwise and counterclockwise directions, may be prevented.

Also, a relative movement of a portion (based on FIG. 9A, the pitch manipulation part 31) that is simultaneously connected to each of the second body parts 530A and 530B to a portion (based on a yaw manipulation part 32 of FIG. 9A) that is simultaneously connected to each of the first body parts 510A and 510B, in the clockwise and counterclockwise directions, may be prevented.

In this regard, a detailed description will be presented in the description of the surgical instrument 1 where the locking apparatus 300 according to another embodiment is installed.

Referring back to FIGS. 7 and 8, in the locking apparatus 300 of the disclosure, an inclined surface may be formed in a certain section of one surface of the first body part 310 (outer circumferential surface), facing one surface of the second body part 330 (inner circumferential surface).

Accordingly, the locking main body parts 353A and 353B, particularly the contact parts 353Aa and 353Ba, are placed in a portion where the outer surface of the first body part 310 disposed inside the second body part 330 is formed as an inclined surface, and thus the locking main body parts 353A and 353B stably contact the first body part 310 and the second body part 330, thereby generating a frictional force.

Referring to FIGS. 7 and 8, the locking main body parts 353A and 353B according to another embodiment are disposed to be capable of moving between the first body part 310 and the second body part 330, particularly between the outer circumferential surface the first body part 310 and the inner circumferential surface of the second body part 330.

Referring to FIGS. 7 and 8, the locking main body parts 353A and 353B according to another embodiment are connected to the first body part 310 and moving between the first body part 310 and the second body part 330 and may include the contact parts 353Aa and 353Ba and elastic members 353Ab and 353Bb.

The contact parts 353Aa and 353Ba are disposed between the first body part 310 and the second body part 330 and have a cylindrical shape like the contact parts 153Aa, 153Ba, 253Aa, 253Ba, 253Ca, and 253Da according to the embodiments. However, the disclosure is not limited thereto, and the contact parts 353Aa and 353Ba may have a ball shape.

The contact parts 353Aa and 353Ba may be disposed to be capable of moving between the first body part 310 and the second body part 330.

Referring to FIGS. 7 and 8, the elastic members 353Ab and 353Bb are disposed between the contact parts 353Aa and 353Ba and the first body part 310, have elastic resilience in a direction in which the interval between the first body part 310 and the second body part 330, which face each other, decreases, and may be formed as a spring having a coil shape like the elastic members 153Ab, 153Bb, 253Ab, 253Bb, 253Cb, and 253Db according to the embodiments.

Referring to FIGS. 7 and 8, the first body part 310 according to another embodiment is disposed inside the second body part 330 to be capable of rotating around the same rotation axis as that of the second body part 330, and a locking support part 317 may be formed in the first body part 310. The locking support part 317 is coupled to the locking main body parts 353A and 353B. Particularly, the locking support part 317 may be connected to the elastic members 353Ab and 353Bb.

Although the locking support part 317 according to another embodiment is integrally formed with the first body part 310, the disclosure is not limited thereto, and various modifications of the embodiments are possible such that the locking support part 317 may be formed as a separate element coupled to the first body part 310 like the support parts 151 and 251 according to the embodiments.

Referring to FIG. 8, the locking support part 317 according to another embodiment may include a plurality of locking support parts forming a symmetry in the upper and lower sides (based on FIG. 8) with respect to a movement axis $X_2$ of the pushing plate part 370, particularly a pushing plate main body 371 that is described later.

Referring to FIGS. 7 and 8, the locking main body parts 353A and 353B according to another embodiment may include a first locking main body part 353A and a second locking main body part 353B. The first locking main body part 353A is coupled to one side of the first body part 310. Particularly, the first locking main body part 353A may be disposed in the upper side (based on FIG. 7) with respect to the movement axis $X_2$ of the pushing plate part 370 that is described later.

The first locking main body part 353A is coupled to the first body part 310, in detail, to the locking support part 317. The first locking main body part 353A may include a contact part 353Aa and an elastic member 353Ab. The elastic member 353Ab connected to the contact part 353Aa has elastic resilience in the outward direction of the contact part 353Aa, that is, in a direction away from the locking support part 317, and due to the elastic resilience of the elastic member 353Ab, the contact part 353Aa may be pushed toward the inclined surface formed in the first body part 310.

The second locking main body part 353B is symmetric with respect to the position of the first locking main body part 353A, and may be coupled to the other side (based on the lower side of FIG. 7) that is symmetric with respect to one side (based on the upper side of FIG. 7) of the first body part 310 to which the first locking main body part 353A is coupled. The first locking main body part 353A and the second locking main body part 353B may be arranged to form origin symmetry with respect to the center of the first body part 310 as the origin.

The second locking main body part 353B may be disposed in the lower side (based on FIG. 8) with respect to the movement axis $X_2$ of the pushing plate part 370, particularly connected to the locking support part 317 disposed in the lower side with respect to the movement axis $X_2$ of the pushing plate part 370.

The second locking main body part 353B may include a contact part 353Ba and an elastic member 353Bb. The elastic member 353Bb connected to the contact part 353Ba has elastic resilience in the outward direction of the contact part 353Ba, that is, in a direction away from the locking support part 317, and due to the elastic resilience of the elastic member 353Bb, the contact part 353Ba may be pushed toward the inclined surface formed in the first body part 310.

Referring to FIGS. 7 and 8, the unlocking unit 360 according to another embodiment is connected to the first body part 310, disposed on the movement path of the locking main body parts 353A and 353B, and may push the locking main body parts 353A and 353B in a direction (based on the counterclockwise direction in FIGS. 7 and 8) in which the interval between the respective surfaces of the first body part 310 and the second body part 330, which face each other, increases.

Referring to FIGS. 7 and 8, the unlocking unit 360 according to another embodiment may include an unlocking main body and a bent part 363.

Referring to FIGS. 7 and 8, although the unlocking main body is not indicated in the drawings, as the structure of the unlocking unit 360 according to another embodiment, that is, the unlocking main body and the bent part 363, is the same as the structure of unlocking units 660A and 660B according to another embodiment that are described later, that is, unlocking main bodies 661A and 661B and bent parts 663A and 663B, particularly an unlocking main body 661A and a bent part 663A, detailed descriptions thereof are presented later.

The unlocking main body is coaxial with the first body part 310 and the second body part 330 and may be rotated around the locking apparatus rotation axis part 395 that is the rotation centers of the first body part 310 and the second body part 330, as a rotation center. The unlocking main body may have a flat plate shape.

A hole portion may be formed at the center of the unlocking main body, and a protruding portion (corresponding to a protruding portion 631 of FIG. 11) protruding toward the unlocking unit 360 may be formed in the second body part 330 to be inserted in the hole portion.

As the protruding portion of the second body part 330 is inserted into the hole portion formed in the unlocking main body, a rotation path of the unlocking unit 360 may be provided, and the unlocking unit 360 may rotated clockwise or counterclockwise while maintaining the rotation center.

Referring to FIGS. 7 and 8, the bent part 363 is provided in the unlocking main body and may be extend in the length direction of the rotation center axis of the unlocking main body from an end portion of the unlocking main body (361).

Accordingly, the bent part 363 is disposed on the movement path of the locking main body parts 353A and 353B, particularly the contact parts 353Aa and 353Ba, and may push the contact parts 353Aa and 353Ba in a direction in which the interval between the respective surfaces of the first body part 310 and the second body part 330, which face each other, increases as the unlocking unit 360 is rotated.

Referring to FIG. 8, the unlocking unit 360 according to another embodiment may receive power, particularly rotational power, from the pushing plate part 370 that is described later. The unlocking unit 360 according to another embodiment, particularly the bent part 363, may simultaneously push the contact parts 353Aa and 353Ba.

Referring to FIG. 8, as the unlocking unit 360 rotates in the in the counterclockwise direction (based on FIG. 8), the contact part 353Aa disposed in the upper side with respect to the movement axis $X_2$ of the pushing plate part 370 and the contact part 353Ba disposed in the lower side with respect to the movement axis $X_2$ of the pushing plate part 370 may simultaneously pushed.

As the unlocking unit 360 rotates in the in the counterclockwise direction (based on FIG. 8), the locking main body parts 353A and 353B are pushed toward the locking support part 317, and thus the locking main body parts 353A and 353B, particularly the contact parts 353Aa and 353Ba, are moved in a direction in which the interval between the first body part 310 and the second body part 330, which face each other, increases. Accordingly, the locking may be released so that the rotation of the second body part 330 to the first body part 310 in the clockwise direction (based on FIG. 8) is possible.

Referring to FIGS. 7 and 8, in the locking main body parts 353A and 353B according to another embodiment, with respect to the movement axis $X_2$ of the pushing plate part 370, the locking main body part 353A may be disposed in the upper side of the first body part 310, and the locking main body part 353B may be symmetrically disposed in the lower side of the first body part 310.

The contact parts 353Aa and 353Ba are separated from the center portion of the first body part 310 due to the elastic resilience of the elastic members 353Ab and 353Bb and moved in a direction in which the interval between the first body part 310 and the second body part 330, which face each other, decreases. In the process, the contact parts 353Aa and 353Ba are stuck between the first body part 310 and the second body part 330, and a locking state may be established in which the movement of the second body part 330 to the first body part 310 in the clockwise direction (based on FIG. 7) is prevented due to the frictional force generated at this time.

Referring to FIGS. 7 and 8, the pushing plate part 370 according to another embodiment is disposed to be capable of moving on the first body part 310 and may move in contact with or not in contact with the first body part 310.

The pushing plate part 370 transmits power to the unlocking unit 360. In detail, the pushing plate part 370 may transmit rotational power to the unlocking unit 360 by pushing the unlocking unit 360.

Accordingly, as the pushing plate part 370 according to another embodiment pushes the unlocking unit 360, the unlocking unit 360 rotates counterclockwise, and the unlocking unit 360 pushes the locking main body parts 353A and 353B, particularly the contact parts 353Aa and 353Ba. Accordingly, as the contact parts 353Aa and 353Ba may move in a direction in which in a direction (counterclockwise direction) in which the interval between one surface of the first body part 310 and one surface of the second body part 330, which face each other, increases, the contact parts 353Aa and 353Ba are released from the state of simultaneously contacting the first body part 310 and the second body part 330, and thus the second body part 330 may move relative to the first body part 310 (based on the clockwise direction in FIG. 8).

Referring to FIGS. 7 and 8, the pushing plate part 370 according to another embodiment may include the pushing plate main body 371 and a pushing plate elastic part 373.

The pushing plate main body 371 moves on the first body part 310 and may move in contact with or not in contact with the first body part 310.

A pushing plate guide part 372 may be formed in the pushing plate main body 371 in a movement direction of the pushing plate main body 371 (based on the $X_2$ axial direction in FIG. 8). The pushing plate guide part 372 is formed in a hole portion shape through which the pushing plate main body 371 passes, and the guide member 390 that is described later may be coupled to the first body part 310 by passing through the pushing plate guide part 372 formed in the pushing plate main body 371.

The guide member 390 may include a plurality of guide members and may be disposed on the first body part 310 with a certain interval in the movement direction of the pushing plate main body 371. Accordingly, the pushing plate main body 371 is provided with a movement path and may stably move in a set path (based on the $X_2$ axial direction in FIG. 8).

Referring to FIGS. 7 and 8, the pushing plate elastic part 373 according to another embodiment is disposed between the base part 380 that is described later and the pushing plate main body 371 and has elastic resilience, and the pushing plate elastic part 373 may be formed as a spring having a coil shape.

Referring to FIG. 7, the pushing plate elastic part 373 is disposed between a second base 383 that is described later and the pushing plate main body 371, and the pushing plate main body 371 may move by passing through the second base 383 to push the pushing plate elastic part 373. The pushing plate elastic part 373 is compressed by the pushing plate main body 371 and may have elastic resilience in a direction in which the pushing plate elastic part 373 is away from the second base 383.

In other words, in a basic state having no external force, the pushing plate elastic part 373 may push the pushing plate part 370 so that the locking apparatus 300 enters a locking state.

The pushing plate elastic part 373 according to another embodiment has elastic resilience in a direction (based on the direction from the left to the right in FIG. 8) in which the pushing plate main body 371 is away from the second base 383, but the disclosure is not limited thereto, and various modifications of the embodiments are possible such that, considering design factors, for example, the installation position of the second base 383 in equipment such as the surgical instrument 1 where the locking apparatus 300 is installed, the pushing plate elastic part 373 may have elastic resilience in a direction toward the second base 383 (based on the direction from the right to the left in FIG. 8).

On surface of the pushing plate part 370 according to another embodiment, particularly the pushing plate main body 371, facing the unlocking unit 360, may include an inclined surface S1 having a certain angle $\theta_2$ with respect to the movement axis $X_2$ of the pushing plate main body 371.

Referring to FIGS. 7 and 8, power may be provided to allow the unlocking unit 360 to rotate counterclockwise in the upper side of the pushing plate main body 371 due to the inclined surface S1 formed in the pushing plate main body 371.

Referring to FIG. 8, the pushing plate main body 371 is moved from the right to the left by the connection member L, such as a wire, connected thereto, and accordingly, the locking main body part 353A disposed in the upper right side with respect to the center of the first body part 310, and the locking main body part 353B disposed in the lower left side with respect to the center of the first body part 310, may rotate counterclockwise.

Accordingly, the locking main body parts 353A and 353B are released from between one surface of the first body part 310 and the second body part 330, which face each other, and the second body part 330 capable of moving relative to the first body part 310 is capable of rotating clockwise (based on FIG. 8).

Referring to FIGS. 7 and 8, the base part 380, particularly the second base 383 and the pushing plate main body 371, are connected by the pushing plate elastic part 373. The pushing plate elastic part 373 has elastic resilience in a direction in which the pushing plate main body 371 is away from the second base 383.

Accordingly, when the unlocking operation of the locking main body parts 353A and 353B is completed, due to the elastic resilience of the pushing plate elastic part 373, the pushing plate main body 371 is moved to the right (based on FIG. 7), and the contact parts 353Aa and 353Ba are pushed by the elastic resilience of the elastic members 353Ab and 353Bb contacting the contact parts 353Aa and 353Ba.

Referring to FIG. 7, due to the elastic resilience of the elastic members 353Ab and 353Bb, the contact parts 353Aa and 353Ba are moved in a direction in which the interval between one surface of the first body part 310 and one surface of the second body part 330 which face each other decreases. As such, the locking main body part 353A disposed in the upper right side with respect to the center of the first body part 310, and the locking main body part 353B disposed in the lower left side with respect to the center of the first body part 310 may prevent the clockwise movement of the second body part 330 to the first body part 310.

In other words, in the locking apparatus 300 according to another embodiment, the movement of the second body part 330 to the first body part 310 in one direction (clockwise) may be prevented due to a frictional force generated as the locking main body parts 353A and 353B are stuck between the first body part 310 and the second body part 330, which face each other.

Referring to FIGS. 7 and 8, the interval between the respective surfaces of the first body part 310 and the second body part 330 according to another embodiment decreases in the clockwise direction, but the disclosure is not limited thereto. In other words, various modifications of the embodiments are possible such that, as the interval between the respective surfaces decreases in the counterclockwise direction, the relative movement of the second body part 330 with respect to the first body part 310 in the counterclockwise direction is prevented due to the frictional force generated as the locking unit is stuck between the first body part 310 and the second body part 330.

Referring to FIGS. 7 and 8, the base part 380 according to another embodiment is installed on the first body part 310 and may fix the first body part 310.

As the structure of the base part 380 according to another embodiment is the same as that of a base part 680 according to another embodiment, a detailed description thereof is presented later.

Referring to FIGS. 7 and 8, the guide member 390 according to another embodiment penetrates the pushing plate part 370, particularly the pushing plate guide part 372 formed in the pushing plate main body 371, and may be coupled to the first body part 310.

A head part (not referenced) formed in the guide member 390 may be formed greater than the width of the pushing plate guide part 372, and thus the pushing plate main body 371 may be prevented from escaping from the first body part 310, and as the pushing plate main body 371 is disposed between the first body part 310 and the head part, the pushing plate main body 371 may push the unlocking unit 360 that the pushing plate main body 371 faces.

As the head part according to another embodiment is the same as a head part 691 according to another embodiment, a detailed description thereof is presented later.

Referring to FIGS. 7 and 8, the locking apparatus rotation axis part 395 according to another embodiment is connected to the first body part 310 and the second body part 330 and passes through the unlocking unit 360 and the second body part 330.

The respective center axes that are rotation centers of the first body part 310, the second body part 330, and the unlocking unit 360 may be congruous with one another due to the locking apparatus rotation axis part 395.

Referring to FIGS. 7 and 8, unlike a locking apparatus 600 according to another embodiment that is described later, in the locking apparatus 300 according to another embodiment, as the unlocking unit 360 that is described later is formed in one body, and thus a relative movement of a second body part 430 to a first body part 410 in one direction (clockwise) only may be prevented.

According to FIGS. 7 and 8, unlike another embodiment of the disclosure, with respect to the rotational direction of the second body part 330, a movement in the clockwise direction only may be prevented by the locking main body parts 353A and 353B.

Referring to FIG. 7, the contact parts 353Aa and 353Ba are stuck between the locking main body parts 353A and 353B, particularly one surface of the first body part 310 and one surface of the second body part 330, which face each other, and the rotation of the second body part 330 in the clockwise direction (based on FIG. 7) is prevented due to a frictional force generated due to the being stuck therebetween, but the rotation in the opposite direction that is the in the counterclockwise direction (based on FIG. 7) is not prevented.

Referring to FIGS. 9A and 9B, by using the locking apparatus 300 according to another embodiment, each of the locking apparatuses 400A and 400B for controlling a movement in the clockwise and counterclockwise directions in a pitch motion may be coupled to the surgical instrument 1, and each of the locking apparatuses 500A and 500B for controlling a movement in the clockwise and counterclockwise directions in a yaw motion may be coupled to the surgical instrument 1. Accordingly, the relative movement of the bent part 35 and the pitch manipulation part 31 (connected to the second body parts 430 and 530) with respect to the pitch manipulation part 31 and the yaw manipulation part 32 (connected to the first body parts 410 and 510) may be locked or unlocked. In FIGS. 9A and 9B, the surgical instrument 1 where the locking apparatuses 400 and 500 according to another embodiment are installed, which are described in detail later.

In the disclosure, for release of a locking state, in order to push a contact part of a locking unit in a direction in which an interval between a first body part and a second body part increases, a pushing plate part is moved to rotate an unlocking unit, thereby allowing the unlocking unit to push the contact part.

However, a method to implement the basic concept of pushing the contact part of the locking unit for the release of a locking state may be easily modified in various ways in addition to the method described in the specification. The disclosure is not limited to the method described in the specification, and may include various modified method for implementing the basic concept.

<Locking Apparatus According to Another Embodiment>

A locking apparatus according to another embodiment is described below with reference to the accompanying drawings.

Figure 10:
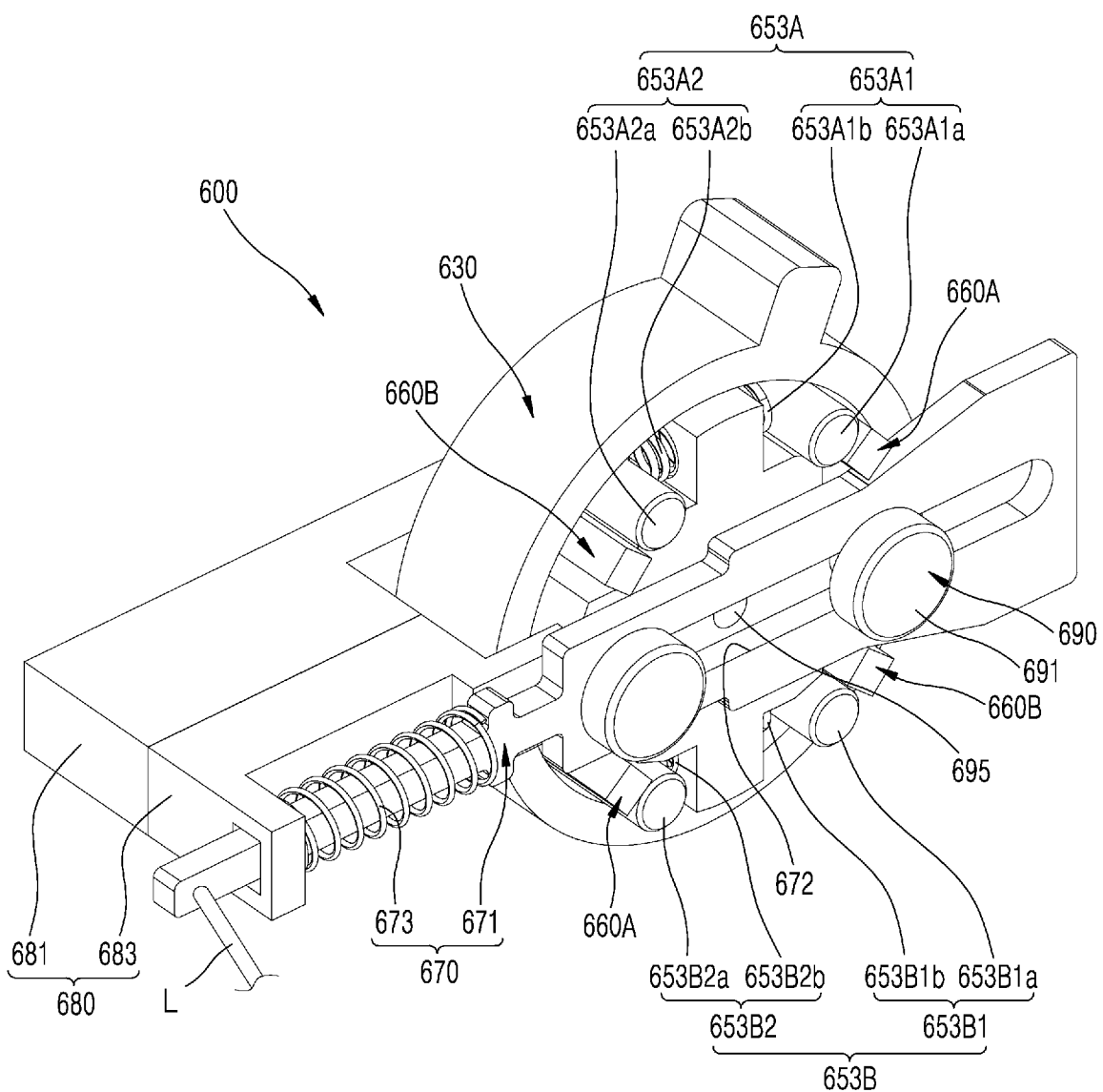
FIG. 10 is a perspective view of a locking apparatus according to another embodiment.
Figure 11:
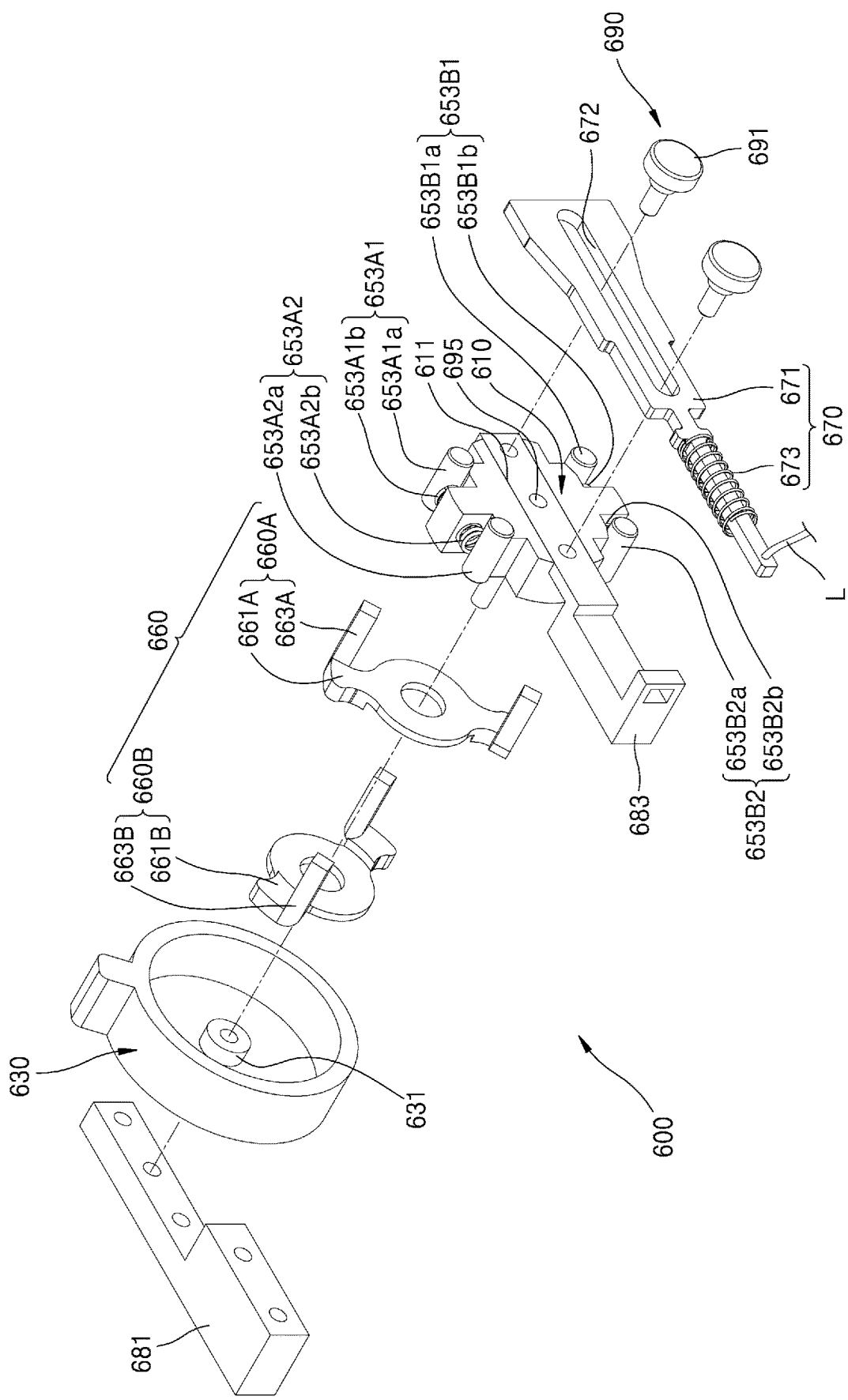
FIG. 11 is an exploded perspective view of the locking apparatus according to another embodiment.
Figure 12:
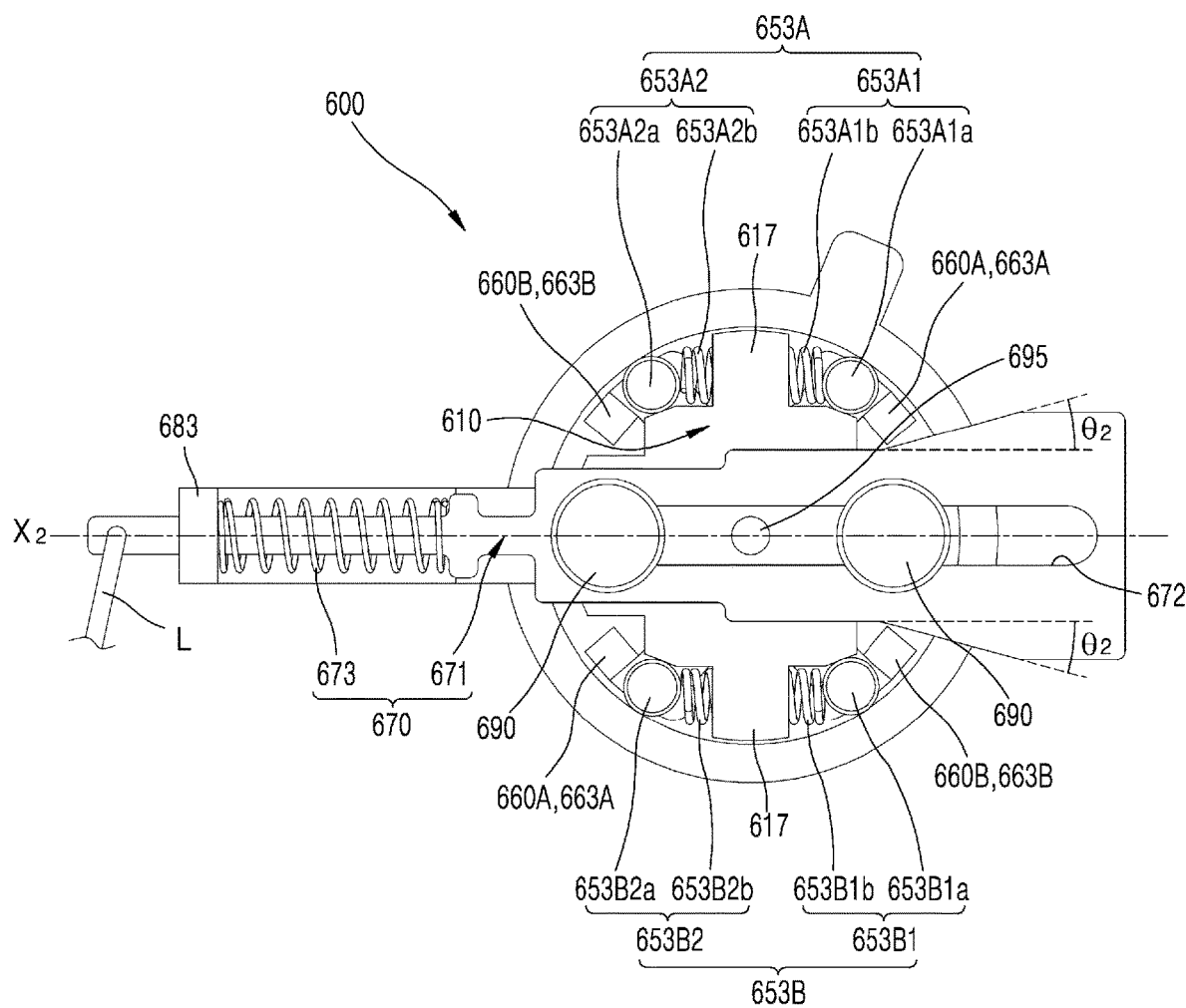
FIG. 12 illustrates a locking state of the locking apparatus according to another embodiment.
Figure 13:
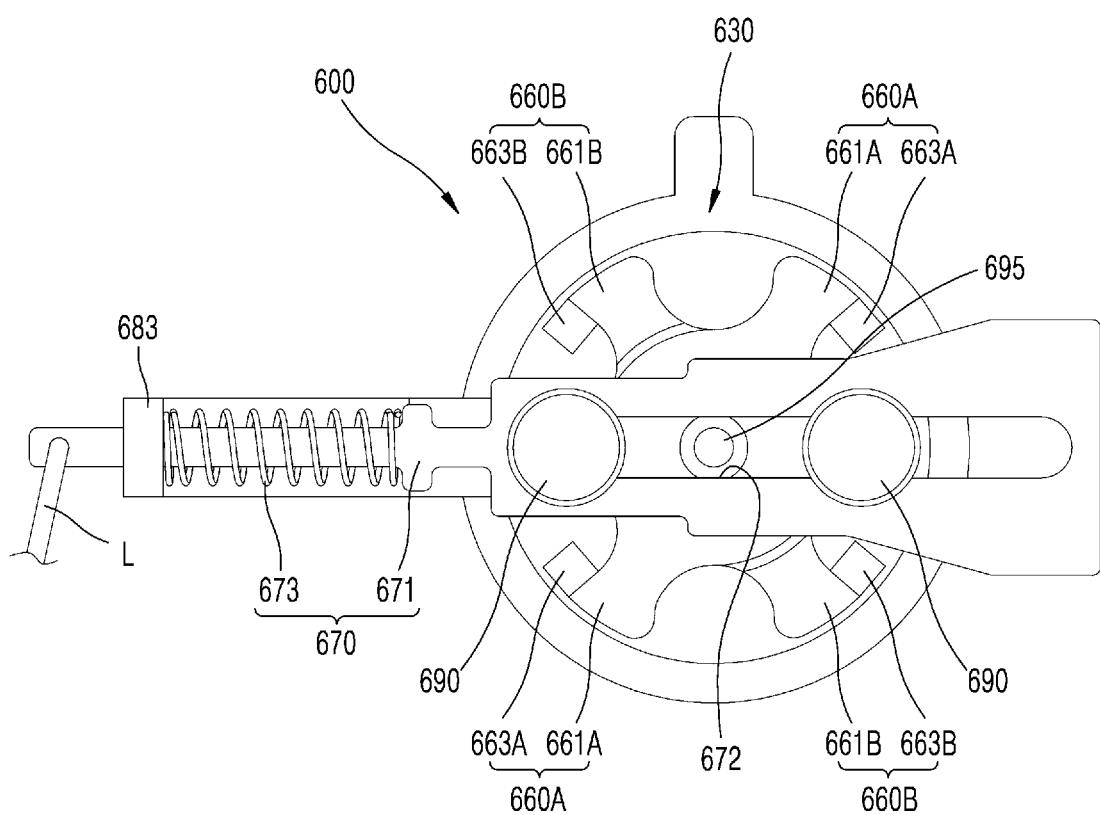
FIG. 13 illustrates an unlocking unit of the locking apparatus in a locking state according to another embodiment.
Figure 14:
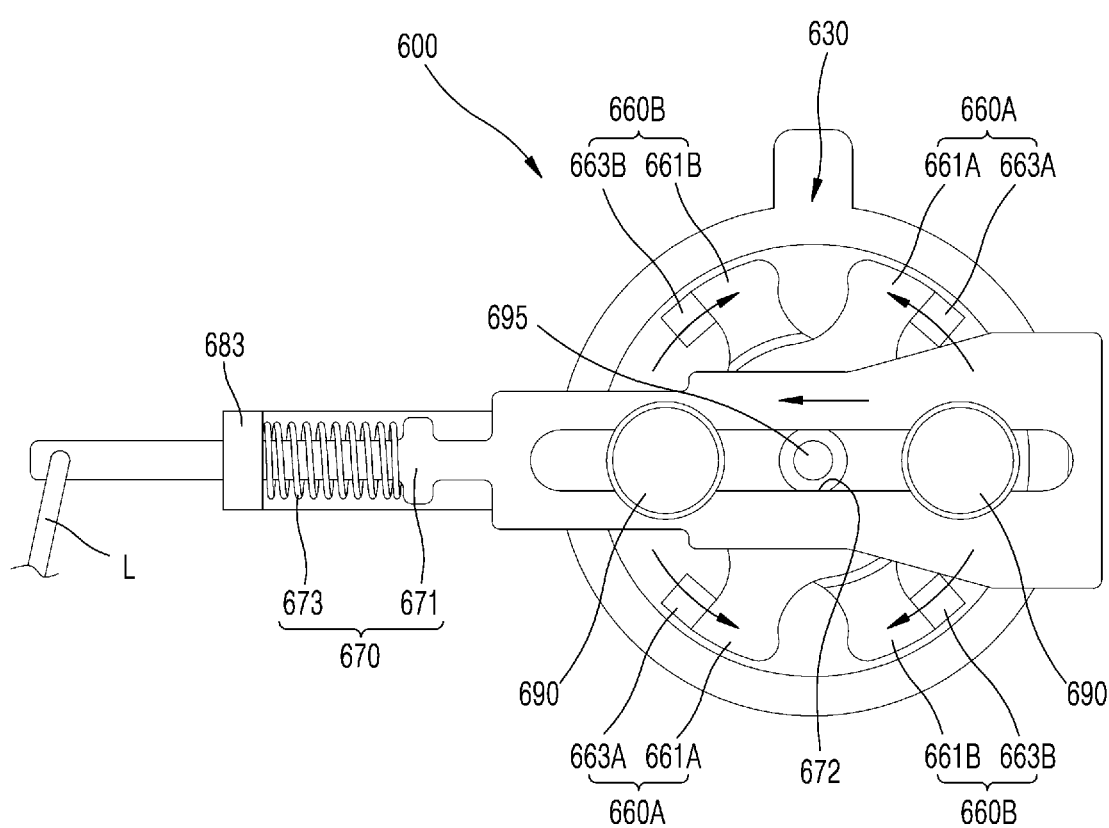
FIG. 14 illustrates an unlocking unit of the locking apparatus in an unlocking state according to another embodiment.
Figure 15:
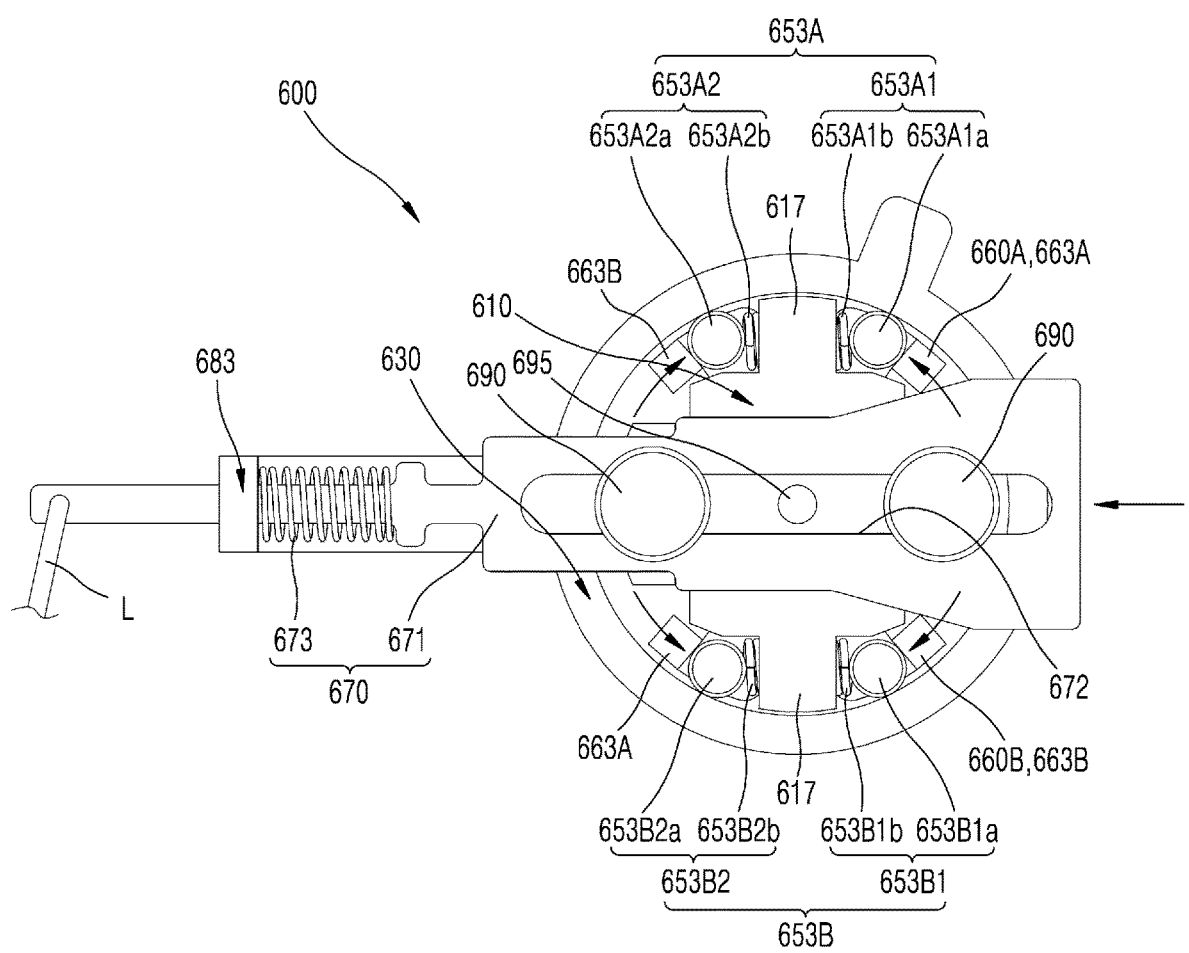
FIG. 15 illustrates an unlocking state of the locking apparatus according to another embodiment.
Figure 16:
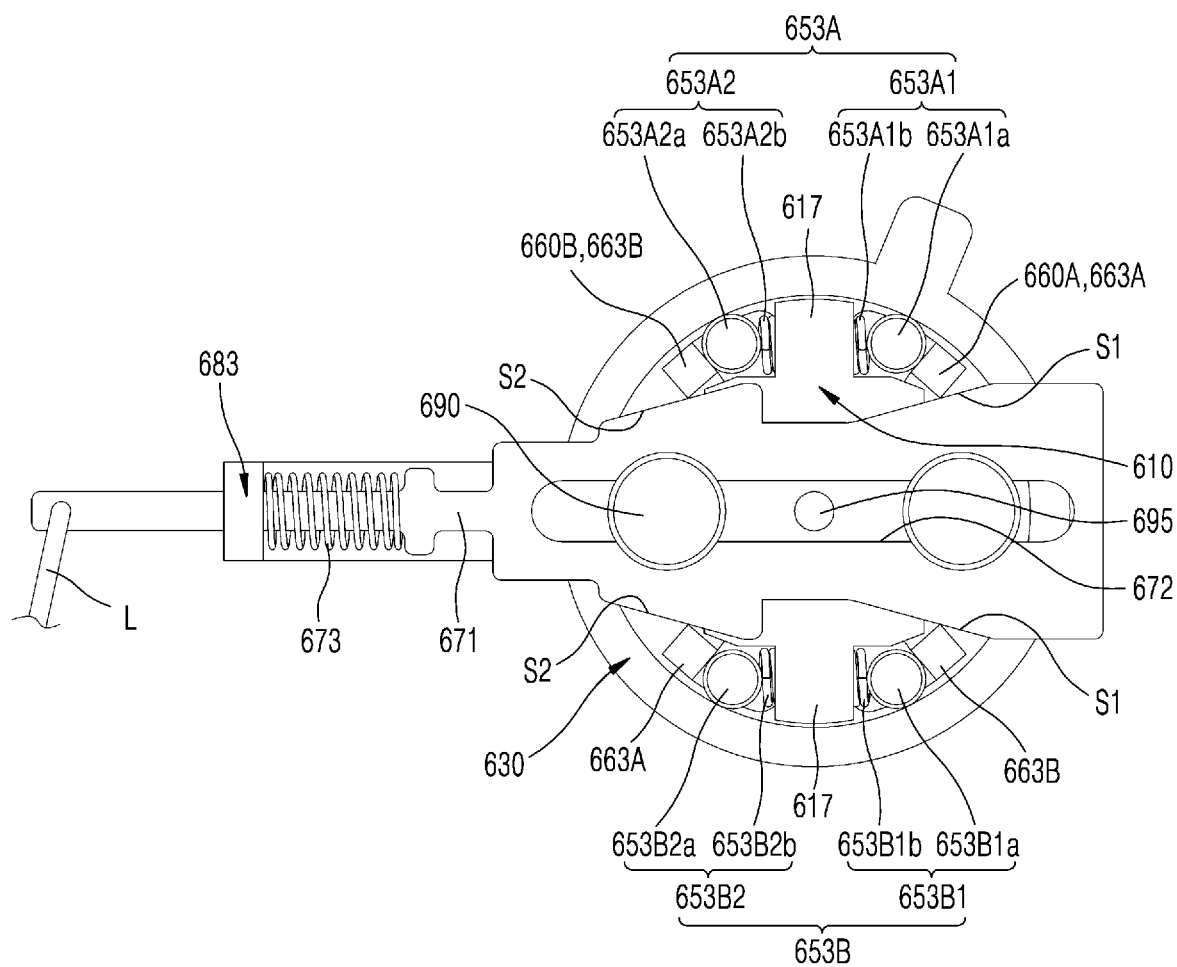
FIG. 16 illustrates a pushing plate main body according to another embodiment.

FIG. 10 is a perspective view of a locking apparatus according to another embodiment. FIG. 11 is an exploded perspective view of the locking apparatus according to another embodiment. FIG. 12 illustrates a locking state of the locking apparatus according to another embodiment. FIG. 13 illustrates an unlocking unit of the locking apparatus in a locking state according to another embodiment. FIG. 14 illustrates an unlocking unit of the locking apparatus in an unlocking state according to another embodiment. FIG. 15 illustrates an unlocking state of the locking apparatus according to another embodiment. FIG. 16 illustrates a pushing plate main body according to another embodiment.

The locking apparatus 600 according to another embodiment may include a first body part 610, a second body part 630, a locking unit 650, the unlocking units 660A and 660B, a pushing plate part 670, the base part 680, a guide member 690, and a locking apparatus rotation axis part 695.

In the locking apparatus 600 according to another embodiment, the locking unit 650 denotes locking main body parts 653A1, 653A2, 653B1, and 653B2. Referring to FIG. 12, in the locking apparatus 600 according to another embodiment, two locking main body parts 653A1 and 653B1 or 653A2 and 653B2 may be provide for locking or unlocking of rotation in any one direction.

Figure 17B:
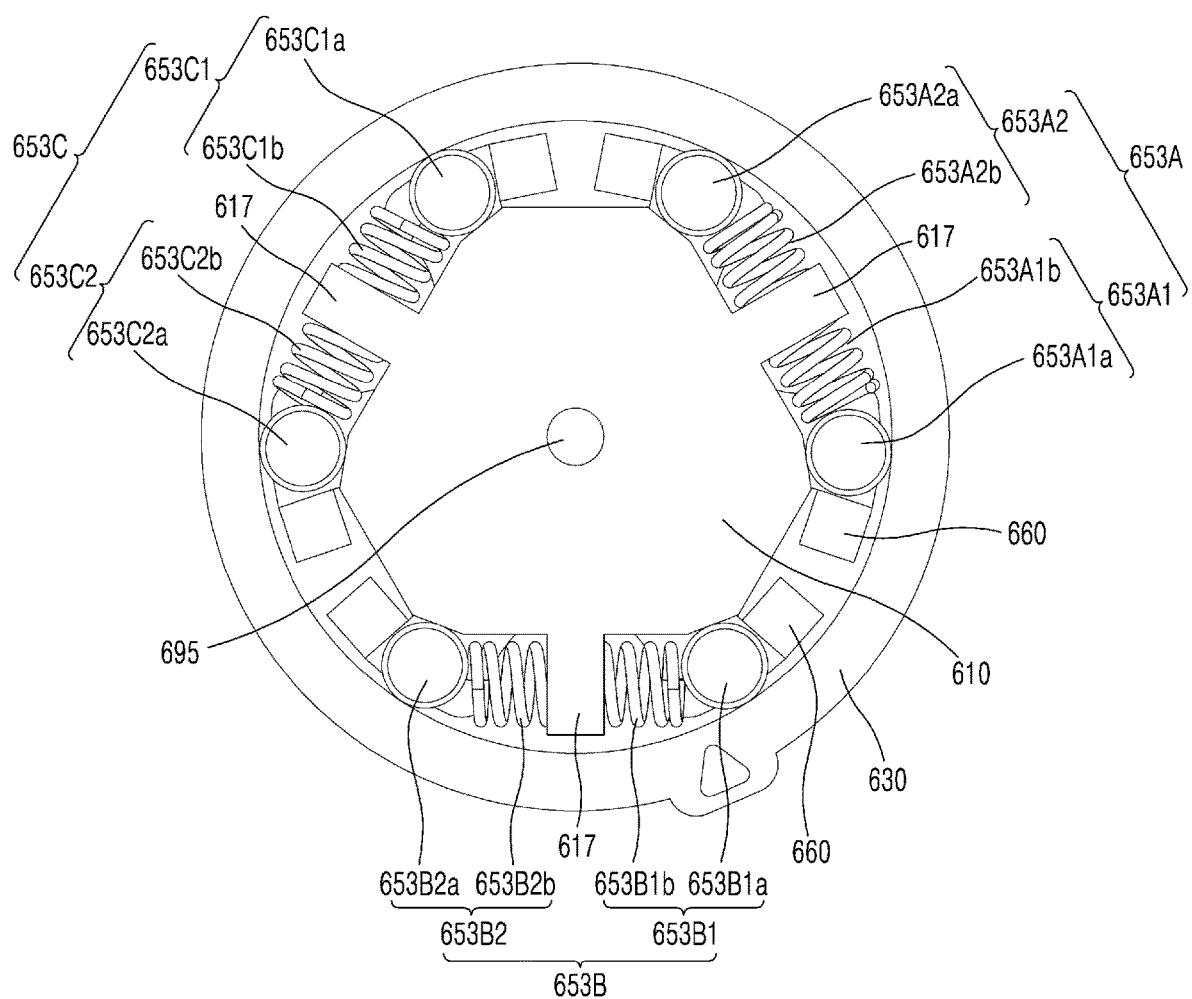

However, the disclosure is not limited thereto, and referring to FIG. 17B, various modifications of the embodiments are possible such that, in a rotational direction of the second body part 630, three locking units 650A, 650B, and 650C, particularly the locking main body parts 653A1, 653A2, 653B1, 653B2, 653C1, and 653C2, may be disposed, or n-number of locking units, where n is an integer exceeding 3, may be formed as the locking unit 650.

Referring to FIG. 17B, as the number of locking units as the locking unit 650 increases, the locking main body parts 653A1, 653A2, 653B1, 653B2, 653C1, and 653C2, particularly contact parts 653A1a, 653A2a, 653B1a, 653B2a, 653C1a, and 653C2a, are moved in a direction in which an interval between the first body part 610 and the second body part 630 decreases, and are in contact with and stuck between the respective surfaces of the first body part 610 and the second body part 630, which face each other, and thus as a frictional force generated due to the being stuck therebetween increases, the locking performance may be improved.

Referring to FIGS. 10 to 12, a movement path, along which the second body part 630 is movable, may be formed in the first body part 610 according to another embodiment. The movement path may be formed outside the first body part 610, and the locking main body parts 653A1, 653A2, 653B1, and 653B2 are movable along one surface forming the outside of the first body part 610.

Referring to FIGS. 10 to 15, the second body part 630 according to another embodiment may be disposed to be coaxial with the first body part 610 and rotatable outside the first body part 610. Although it is not illustrated in the drawings, the second body part 630 may be connected to a movable portion in a separate apparatus, such as the surgical instrument 2, where the locking apparatus 600 is installed.

The second body part 630 has a constant radius and a constant radius of curvature and may have a cylindrical shape having a hollow space therein. Referring to FIG. 10, the first body part 610, the unlocking units 660A and 660B, and the locking main body parts 653A1, 653A2, 653B1, and 653B2 may be disposed inside the second body part 630 according to another embodiment.

Accordingly, when the second body part 630 rotates outside the first body part 610, a certain apparatus connected to the second body part 630 is capable of rotational motion or linear motion together. In a locking state in which the relative movement of the second body part 630 with respect to the first body part 610 is prevented due to the locking main body parts 653A1, 653A2, 653B1, and 653B2, a linear or rotational motion of a portion connected to the second body part 630 may be restricted.

When an interval between one surface of the first body part 610 and one surface of the second body part 630, which face each other, decreases in a certain section in one direction with respect to the center portion of the first body part 610, and the locking main body parts 653A1, 653A2, 653B1, and 653B2 simultaneously contact the first body part 610 and the second body part 630, the movement of the second body part 630 to the first body part 610 in both directions, particularly in the clockwise and counterclockwise directions, is prevented.

Referring to FIG. 12, an inclined surface may be formed in a certain section of an outer surface of the first body part 610 according to another embodiment.

Accordingly, the locking main body parts 653A1, 653A2, 653B1, and 653B2, particularly the contact parts 653A1a, 653A2a, 653B1a, and 653B2a, are placed in a portion where the outer surface of the first body part 610 is formed as an inclined surface and stably contact the first body part 610 and the second body part 630, thereby generating a frictional force.

Referring to FIG. 10, the locking main body parts 653A1, 653A2, 653B1, and 653B2 according to another embodiment are disposed to be movable between the first body part 610 and the second body part 630, particularly between an outer circumferential surface of the first body part 610 and an inner circumferential surface of the second body part 630.

Referring to FIGS. 10 and 11, the locking main body parts 653A1, 653A2, 653B1, and 653B2 according to another embodiment are connected to the first body part 610 to be movable between the first body part 610 and the second body part 630, and may include the contact parts 653A1a, 653A2a, 653B1a, and 653B2a and elastic members 653A1b, 653A2b, 653B1b, and 653B2b.

The contact parts 653A1a, 653A2a, 653B1a, and 653B2a are disposed between the first body part 610 and the second body part 630 and may have a cylindrical shape like the contact parts 153Aa, 153Ba, 253Aa, 253Ba, 253Ca, 253Da, 653Aa, and 653Ba according to the above-described embodiments. However, the disclosure is not limited thereto, and the contact parts 653A1a, 653A2a, 653B1a, and 653B2a may have a ball shape.

The contact parts 653A1a, 653A2a, 653B1a, and 653B2a may be disposed to be movable between the first body part 610 and the second body part 630.

Referring to FIGS. 10 and 12, the elastic members 653A1b, 653A2b, 653B1b, and 653B2b are disposed between the contact parts 653A1a, 653A2a, 653B1a, and 653B2a and the first body part 610, have elastic resilience in a direction in which the interval between the first body part 610 and the second body part 630, which face each other, decreases, and may be formed as a spring having a coil shape like the elastic members 153Ab, 153Bb, 253Ab, 253Bb, 253Cb, 253Db, 653Ab, and 653Bb according to the above-described embodiments.

Referring to FIG. 12, the first body part 610 according to another embodiment is disposed to be coaxial with the second body part 630 inside the second body part 630, and a locking support part 617 may be formed in the first body part 610.

The locking support part 617 is coupled to the locking main body parts 653A1, 653A2, 653B1, and 653B2, particularly the elastic members 653A1b, 653A2b, 653B1b, and 653B2b.

Referring to FIG. 10, although the locking support part 617 according to another embodiment is integrally formed with the first body part 610, the disclosure is not limited thereto, and various modifications of the embodiments are possible such that, like the support parts 151 and 251 according to the embodiments, the locking support part 617 may be separately provided to be coupled to the first body part 610.

Referring to FIG. 12, the locking support part 617 according to another embodiment may include a plurality of locking support parts that are symmetrically formed in the upper and lower sides (based on FIG. 12) with respect to the pushing plate part 670 that is described later, particularly the movement axis $X_2$ of a pushing plate main body 671.

Referring to FIGS. 10 and 12, the locking main body parts 653A1, 653A2, 653B1, and 653B2 according to another embodiment may include the first locking main body parts 653A1 and 653A2 and the second locking main body parts 653B1 and 653B2. The first locking main body parts 653A1 and 653A2 are coupled to one side of the first body part 610, particularly in the upper side (based on FIG. 12) with respect to the movement axis $X_2$ of the pushing plate part 670 that is described later.

The first locking main body parts 653A1 and 653A2 are connected to the first body part 610, particularly the locking support part 617, and may include a plurality of first locking main body parts. The first locking main body parts 653A1 and 653A2 may be disposed to be symmetric with respect to the locking support part 617.

The first locking main body parts 653A1 and 653A2 may include the contact parts 653A1a and 653A2a and the elastic member 653A1b and 653A2b, and the elastic member 653A1b and 653A2b that are respectively connected to the contact parts 653A1a and 653A2a may have elastic resilience to push the contact parts 653A1a and 653A2a outward from the locking support part 617. Due to the elastic resilience of the elastic member 653A1b and 653A2b, the contact parts 653A1a and 653A2a may be pushed outward with respect to the center portion of the first body part 610, that is, toward the inclined surface formed in the first body part 610.

The second locking main body parts 653B1 and 653B2 may be formed at positions symmetric with respect to the positions of the first locking main body parts 653A1 and 653A2, and may be coupled to the other side (based on the lower side in FIG. 12) that is symmetric with respect to one side of the first body part 610 (based on the upper side in FIG. 12) to which the first locking main body parts 653A1 and 653A2 are coupled.

The second locking main body parts 653B1 and 653B2 may be disposed in the lower side (based on FIG. 12) with respect to the movement axis $X_2$ of the pushing plate part 670, particularly with respect to the movement axis $X_2$ of the pushing plate part 670, and connected to the locking support part 617 disposed in the lower side of the first body part 610, and may include a plurality of second locking main body parts. The second locking main body parts 653B1 and 653B2 may be disposed to be symmetric with respect to the locking support part 617 as a center portion.

The second locking main body parts 653B1 and 653B2 may include the contact parts 653B1a and 653B2a and the elastic members 653B1b and 653B2b, and the elastic members 653B1b and 653B2b respectively connected to the contact parts 653B1a and 653B2a may have elastic resilience to push the contact parts 653B1a and 653B2a outward from the locking support part 617. Due to the elastic resilience of the elastic members 653B1b and 653B2b, the contact parts 653B1a and 653B2a may be pushed toward the inclined surface formed in the first body part 610.

Referring to FIGS. 10 and 12, the locking main body parts 653A1, 653A2, 653B1, and 653B2 according to another embodiment are coupled to both sides of the locking support part 617 formed in the first body part 610.

In the locking apparatus 600 according to another embodiment, a total of four locking main body parts 653A1, 653A2, 653B1, and 653B2 including the first locking main body parts 653A1 and 653A2 and the second locking main body parts 653B1 and 653B2.

However, the disclosure is not limited thereto, and various modifications of the embodiments are possible such that over four locking main body parts may be disposed along the circumference of the first body part 610 commonly having the rotation center of the second body part 630.

Referring to FIGS. 10 to 15, the unlocking units 660A and 660B according to another embodiment are connected to the first body part 610, disposed on the movement path of the locking main body parts 653A1, 653A2, 653B1, and 653B2, and may push the locking main body parts 653A1, 653A2, 653B1, and 653B2 in a direction in which the interval between the respective surfaces of the first body part 610 and the second body part 630, which face each other, increases.

Referring to FIGS. 10 to 15, the unlocking units 660A and 660B according to another embodiment may include the unlocking main bodies 661A and 661B and the bent parts 663A and 663B.

The unlocking main bodies 661A and 661B are coaxial with the first body part 610 and the second body part 630 and may be rotated around the locking apparatus rotation axis part 695 that is the rotation center of the first body part 610 and the second body part 630, as a rotation center. The unlocking main bodies 661A and 661B may have a flat plate shape.

A hole portion may be formed at centers of the unlocking main bodies 661A and 661B, and the protruding portion 631 protruding toward the unlocking units 660A and 660B is formed on the second body part 630 and may be inserted into the hole portion. As the protruding portion 631 of the second body part 630 is inserted into the hole portion formed in the unlocking main bodies 661A and 661B, a rotation path of the unlocking units 660A and 660B is provided, and the unlocking units 660A and 660B may be rotated clockwise or counterclockwise while maintaining the rotation center.

Referring to FIGS. 10 to 12, the bent parts 663A and 663B are provided on the unlocking main bodies 661A and 661B and may extend from end portions of the unlocking main bodies 661A and 661B in a rotation center axis direction of the unlocking main bodies 661A and 661B.

Accordingly, the bent parts 663A and 663B are disposed on the locking unit 650, particularly on a movement path of the contact parts 653A1a, 653A2a, 653B1a, and 653B2a, and as the unlocking units 660A and 660B rotate, may push the contact parts 653A1a, 653A2a, 653B1a, and 653B2a in a direction in which the interval between the respective surfaces of the first body part 610 and the second body part 630, which face each other, increases.

Referring to FIG. 13, the unlocking units 660A and 660B according to another embodiment may include a plurality of unlocking units, and the unlocking units 660A and 660B may receive power, particularly rotational power, from the pushing plate part 670 that is described later.

In this state, the unlocking units 660A and 660B may rotate in different directions. The unlocking units 660A and 660B may be disposed to be origin symmetric with respect to the rotation center of the second body part 630.

FIGS. 12 to 14, the unlocking units 660A and 660B may simultaneously and respectively push any one of the first locking main body parts 653A1 and 653A2 and the second locking main body parts 653B1 and 653B2 that are disposed to be origin symmetrical with the one of the first locking main body parts 653A1 and 653A2 with respect to the locking apparatus rotation axis part 695.

Accordingly, referring to FIG. 12, as the unlocking unit 660A that is singular rotates counterclockwise (based on FIG. 12), the locking main body part 653A1, particularly the contact part 653A1a, disposed in the upper right side (based on FIG. 12) with respect to the center of the first body part 610, and the locking main body part 653B1, particularly the contact part 653B1a, disposed in the lower left side (based on FIG. 12) with respect to the center of the first body part 610, may be simultaneously pushed.

As the unlocking unit 660A rotates counterclockwise, the locking main body parts 653A1 and 653B1 are pushed toward the center portion of the first body part 610, and thus the locking main body parts 653A1 and 653B1, particularly the contact parts 653A1a and 653B1a, are moved in a direction in which the interval between the first body part 610 and the second body part 630, which face each other, increases. Accordingly, locking may be released so that the rotation of the second body part 630 in the clockwise direction (based on FIG. 12) is possible.

Referring to FIG. 12, as the unlocking unit 660B that is the other one rotates clockwise (based on FIG. 12), the locking main body part 653A2, particularly the contact part 653A2a, disposed in the upper left side (based on FIG. 12) with respect to the center of the first body part 610, and the locking main body part 653B2 disposed in the lower right side (based on FIG. 12) with respect to the center of the first body part 610, may be simultaneously pushed.

As the unlocking unit 660B rotates clockwise, the locking main body parts 653A2 and 653B2 are pushed toward the center portion of the first body part 610, the locking main body parts 653A2 and 653B2, particularly the contact parts 653A2a and 653B2a, are moved in a direction in which the interval between the first body part 610 and the second body part 630, which face each other, increases. Accordingly, the locking may be released so that the rotation in the in the counterclockwise direction (based on FIG. 12) of the second body part 630 to the first body part 610 is possible.

Referring to FIGS. 12 to 14, the unlocking units 660A and 660B according to another embodiment may include a plurality of unlocking units, and the unlocking units 660A and 660B may be respectively disposed to be origin symmetric with respect to the center of the second body part 630, that is, the center of the locking apparatus rotation axis part 695.

In detail, the bent parts 663A and 663B provided in the unlocking units 660A and 660B disposed on the movement path of the contact parts 653A1a, 653A2a, 653B1a, and 653B2a may be disposed to be original symmetric with respect to the center of the second body part 630, that is, the locking apparatus rotation axis part 695.

Accordingly, as the unlocking units 660A and 660B that are plural, not singular, rotate in different directions of the clockwise and counterclockwise directions, the unlocking units 660A and 660B push the contact parts 653A1a, 653A2a, 653B1a, and 653B2a to move the contact parts 653A1a, 653A2a, 653B1a, and 653B2a in a direction in which the interval between one surface of the first body part 610 and one surface of the second body part 630, which face each other, increases.

Referring to FIG. 12, among the locking main body parts 653A1, 653A2, 653B1, and 653B2 according to another embodiment, the locking main body parts 653A1 and 653A2 are disposed in the upper side at both sides of the center portion of the first body part 610 with respect to the movement axis $X_2$ of the pushing plate part 670, and the locking main body parts 653B1 and 653B2 may be disposed in the lower side at both sides of the first body part 610 corresponding thereto.

The contact parts 653A1a, 653A2a, 653B1a, and 653B2a are moved due to the elastic resilience of the elastic members 653A1b, 653A2b, 653B1b, and 653B2b in a direction away from the center portion of the first body part 610, that is, in a direction in which the interval between one surface of the first body part 610 and one surface of the second body part 630, which face each other, decreases.

In detail, the contact part 653A1a disposed in the upper right side (based on FIG. 12) with respect to the movement axis $X_2$ of the pushing plate part 670, and the contact part 653B1a disposed in the lower left side (based on FIG. 12) with respect to the movement axis $X_2$ of the pushing plate part 670, are stuck between the first body part 610 and the second body part 630, and a locking state may be established in which the movement of the first body part 610 to the second body part 630 in the clockwise direction (based on FIG. 12) is prevented due to the frictional force.

Additionally, the contact part 653A2a disposed in the upper left side (based on FIG. 12) with respect to the movement axis $X_2$ of the pushing plate part 670, and the contact part 653B2a disposed in the lower right side (based on FIG. 12) with respect to the movement axis $X_2$ of the pushing plate part 670, are struck between the first body part 610 and the second body part 630, and a locking state may be established in which the movement of the first body part 610 to the second body part 630 in the in the counterclockwise direction (based on FIG. 12) is prevented due to the frictional force.

In other words, the locking main body parts 653A1, 653A2, 653B1, and 653B2 comprise a plurality of locking main body parts and are disposed at both sides with respect to the center portion of the first body part 610, and thus the movement of the first body part 610 to the second body part 630 in both directions may be prevented. As the pushing plate part 670 that is singular and described later pushes the unlocking units 660A and 660B, the unlocking units 660A and 660B push the locking main body parts 653A1, 653A2, 653B1, and 653B2 to move toward the center portion of the first body part 610, and thus the movement of the first body part 610 to the second body part 630 in both directions may be possible.

Referring to FIGS. 10 to 15, the pushing plate part 670 according to another embodiment is disposed to be movable on the first body part 610 and may transmit power to the unlocking units 660A and 660B. In detail, the pushing plate part 670 pushes the unlocking units 660A and 660B to transmit rotational power to the unlocking units 660A and 660B.

Accordingly, as the pushing plate part 670 moves and pushes the unlocking units 660A and 660B, the unlocking units 660A and 660B rotates counterclockwise or clockwise. As the unlocking units 660A and 660B push the locking main body parts 653A1, 653A2, 653B1, and 653B2, particularly the contact parts 653A1a, 653A2a, 653B1a, and 653B2a, the contact parts 653A1a, 653A2a, 653B1a, and 653B2a may be moved in a direction in which the interval between one surface of the first body part 610 and one surface of the second body part 630, which face each other, increases. Accordingly, the movement of the second body part 630 to the first body part 610 may be possible.

Referring to FIGS. 10 to 15, the pushing plate part 670 according to another embodiment may include the pushing plate main body 671 and a pushing plate elastic part 673. The pushing plate main body 671 moves on the first body part 610 may move in contact with or not in contact with the first body part 610.

A pushing plate guide part 672 is formed in the pushing plate main body 671 in a movement direction of the pushing plate main body 671 (based on the $X_2$ axial direction in FIG. 12). The pushing plate guide part 672 has a hole portion shape through which the pushing plate main body 671 that is described later passes, and the guide member 690 may be coupled to the first body part 610 by passing through the pushing plate guide part 672 formed in the pushing plate main body 671.

The guide member 690 may include a plurality of guide members and may be separately disposed on the first body part 610 with a certain interval in the movement direction of the pushing plate main body 671. Accordingly, the pushing plate main body 671 may be provided with a movement path and may stably move in a set path (based on the $X_2$ axial direction in FIG. 12).

Referring to FIGS. 10 to 15, the pushing plate elastic part 673 according to another embodiment is disposed between the base part 680 that is described later and the pushing plate main body 671 and has elastic resilience. The pushing plate elastic part 673 may be formed as a spring having a coil shape.

Referring to FIG. 12, the pushing plate elastic part 673 is disposed between a second base 683 that is described later and the pushing plate main body 671, and may push the pushing plate elastic part 673 when the pushing plate main body 671 moves by passing through the second base 683. The pushing plate elastic part 673 is compressed by the pushing plate main body 671 and may have elastic resilience in a direction in which the pushing plate elastic part 673 is away from the second base 683.

In other words, in a basic state having no external force, the pushing plate elastic part 673 may push the pushing plate part 670 so that the locking apparatus 600 enters a locking state.

The pushing plate elastic part 673 according to another embodiment has elastic resilience in a direction in which the pushing plate main body 671 is away from the second base 683 (based on the direction from the right to the left in FIG. 12), but various modifications of the embodiments are possible such that, considering design factors, for example, the installation position of the second base 683 in equipment such as the surgical instrument 1 where the locking apparatus 600 is installed, the pushing plate elastic part 673 may have elastic resilience in a direction toward the second base 683 (based on the direction from the right to the left in FIG. 12).

Referring to FIGS. 10 to 15, in the pushing plate part 670 according to another embodiment, particularly the pushing plate main body 671, one surface facing the unlocking units 660A and 660B may be formed as the inclined surface S1 having the certain angle $\theta_2$ with respect to the movement axis $X_2$ of the pushing plate main body 671.

Referring to FIG. 12, the pushing plate main body 671 according to another embodiment may be formed to be symmetric with respect to the movement axis $X_2$.

Accordingly, the pushing plate main body 671 pushes the unlocking unit 660A, particularly the bent part 663A, disposed in the upper right side (based on FIG. 12) of the first body part 610 and may simultaneously push the unlocking unit 660B, particularly the bent part 663B, disposed in the lower right side of the first body part 610 (based on FIG. 12).

As the pushing plate main body 671 is formed to be symmetric with respect to the movement axis $X_2$, like one surface facing the unlocking unit 660A in the upper side (based on FIG. 12) forms the certain angle $\theta_2$ with respect to the movement axis $X_2$, one surface facing the unlocking unit 660B in the lower side (based on FIG. 12) may form an angle $\theta_2$ having the same amount with respect to the movement axis $X_2$.

Referring to FIGS. 12 and 13, due to the inclined surface S1 formed in the pushing plate main body 671, power is provided so that the unlocking unit 660A rotates counterclockwise in the upper side of the pushing plate main body 671, and power may be provided so that the unlocking unit 660B rotates clockwise in the lower side of the pushing plate main body 671.

In this state, the unlocking unit 660A may have two bent parts 663A at the opposite ends thereof, and accordingly, the unlocking unit 660A that is singular and rotates may simultaneously push the two contact parts 653A1*a* and 653B1*a*.

Likewise, the unlocking unit 660B may also have two bent part 663B at the opposite ends thereof, and accordingly, the unlocking unit 660B that is singular and rotates may simultaneously push the two contact parts 653A2*a* and 653B2*a*.

Referring to FIG. 16, the inclined surfaces S1 and S2 formed in the pushing plate part 670 according to another embodiment, particularly the pushing plate main body 671, may include the first inclined surface S1 and the second inclined surface S2.

The second inclined surface S2 is formed in front of the first inclined surface S1 when a direction in which the first inclined surface S1 pushes the unlocking units 660A and 660B (based on the direction from the right to the left in FIG. 16) is assumed to be the front side, and may be formed to be inclined in the same direction as the first inclined surface S1.

Referring to FIG. 16, as the pushing plate main body 671 moves, the first inclined surface S1 pushes the unlocking unit 660A, particularly the bent part 663A in the upper right side with respect to the center of the first body part 610, the locking main body part 653A1 disposed in the upper right side and the locking main body part 653B1 disposed in the lower left side rotate counterclockwise.

Likewise, the second inclined surface S2 pushes the unlocking unit 660A, particularly the bent part 663A in the lower left side with respect to the center of the first body part 610, so as to provide additional power to rotate the unlocking unit 660A counterclockwise.

Meanwhile, as the first inclined surface S1 pushes the bent part 663B in the lower right side with respect to the center of the first body part 610, the locking main body part 653B2 disposed in the lower right side and the locking main body part 653A2 disposed in the upper left side rotate clockwise.

Simultaneously, the second inclined surface S2 pushes the unlocking unit 660B, particularly the bent part 663B, in the upper left side with respect to the center of the first body part 610, so as to provide additional power to rotate the unlocking unit 660B clockwise.

Referring to FIG. 16, when the first inclined surface S1 pushes the unlocking units 660A and 660B, particularly the bent part 663A disposed in the upper right side and the bent part 663B disposed in the lower right side (based on FIG. 16) with respect to the center of the first body part 610, the unlocking unit 660A rotates counterclockwise, and the other unlocking unit 660B rotates clockwise.

The second inclined surface S2 contacts each of the bent part 663B and the bent part 663A that are respectively disposed to be symmetric with the bent parts 663A and 663B contacting the first inclined surface S1.

Accordingly, in addition to pushing of the pushing plate main body 671 by the first inclined surface S1, the bent part 663B disposed in the upper side with respect to the movement axis $X_2$ of the pushing plate main body 671 contacts the second inclined surface S2 and is pushed and rotated clockwise. Simultaneously, the bent part 663A disposed in the lower side with respect to the movement axis $X_2$ of the pushing plate main body 671 contacts the second inclined surface S2 and is pushed and rotated counterclockwise.

Referring to FIGS. 14 and 15, the pushing plate main body 671 is moved from the right to the left by the connection member L such as a wire connected thereto. Accordingly, the locking main body part 653A1 disposed in the upper right side and the locking main body part 653B1 disposed in the lower left side with respect to the center of the first body part 610 may rotate counterclockwise. Simultaneously, the locking main body part 653A2 disposed in the upper left side and the locking main body part 653B2 disposed in the lower right side with respect to the center of the first body part 610 may be simultaneously rotated.

The locking main body parts 653A1, 653A2, 653B1, and 653B2 pushed by the unlocking units 660A and 660B, escape from between one surface of the first body part 610 and the second body part 630, which face each other, and the second body part 630 capable of moving relative to the first body part 610 may be capable of rotating in both directions.

Referring to FIGS. 12 to 15, the base part 680, particularly the second base 683 and the pushing plate main body 671, are connected by the pushing plate elastic part 673. The pushing plate elastic part 673 has elastic resilience in a direction in which the pushing plate main body 671 is away from the second base 683.

Accordingly, when an unlocking operation of the locking main body parts 653A1, 653A2, 653B1, and 653B2 is completed, due to the elastic resilience of the pushing plate elastic part 673, the pushing plate main body 671 is moved to the right (based on FIG. 13), due to the elastic resilience of the elastic members 653A1*b*, 653A2*b*, 653B1*b*, and 653B2*b* connected to the contact parts 653A1*a*, 653A2*a*, 653B1*a*, and 653B2*a*, the contact parts 653A1*a*, 653A2*a*, 653B1*a*, and 653B2*a* are pushed.

Referring to FIG. 12, due to the elastic resilience of the elastic members 653A1*b*, 653A2*b*, 653B1*b*, and 653B2*b*, the contact parts 653A1*a*, 653A2*a*, 653B1*a*, and 653B2*a* are moved in a direction in which the interval between one surface of the first body part 610 and one surface of the second body part 630, which face each other, decreases. The locking main body part 653A1 disposed in the upper right side the locking main body part 653B1 disposed in the lower left side with respect to the center of the first body part 610 may prevent the movement of the first body part 610 to the second body part 630 in the clockwise direction.

Referring to FIG. 12, due to the locking main body part 653A2 disposed in the upper left side and the locking main body part 653B2 disposed in the lower right side with respect to the center of the first body part 610, the movement of the first body part 610 to the second body part 630 in the counterclockwise direction may be prevented.

In other words, in the locking apparatus 600 according to another embodiment, the frictional force generated as the locking main body parts 653A1, 653A2, 653B1, and 653B2 are stuck between the first body part 610 and the second body part 630, which face each other may prevent the movement of the first body part 610 to the second body part 630 in both clockwise and counterclockwise directions.

Referring to FIGS. 10 and 11, the base part 680 according to another embodiment may include a first base 681 and the second base 683. In this state, the first base 681 is disposed outside the second body part 630. The second base 683 is fixed to the first base 681 and the first body part 610, and a hole portion (set with no reference numeral) may be formed in the second base 683 so that the pushing plate main body 671 passes therethrough.

The second base 683 may be placed on a first body groove part 611 formed in the first body part 610. Accordingly, the first body part 610 may be prevented from rotating, and the rotation of the first body part 610 together due to the rotation of the unlocking units 660A and 660B may be prevented.

The first base 681 may prevent escape of the second body part 630 in the rotation axis direction, and in this state, the first base 681 may be provided not to interfere with the rotation of the second body part 630. The first base 681 may not be provided as necessary.

The base part 680 is fixed to a portion, for example, the surgical instrument 2, where the locking apparatus 600 is installed. As the end portion of the pushing plate elastic part 673 is coupled to the base part 680 to be supported thereon so that the pushing plate elastic part 673 has elastic resilience toward the pushing plate main body 671, the elastic resilience may be reinforced.

Referring to FIGS. 10 and 11, the guide member 690 according to another embodiment may be coupled to the first body part 610 and may penetrate the pushing plate guide part 672 that extends and is formed in the pushing plate part 670, particularly the pushing plate main body 671.

The head part 691 formed in the guide member 690 is greater than the width of the pushing plate guide part 672, and may prevent the pushing plate main body 671 from escaping from the first body part 610. The pushing plate main body 671 is disposed between the first body part 610 and the head part 691, and the pushing plate main body 671 may push the unlocking units 660A and 660B, which face each other.

Referring to FIGS. 10 and 11, the locking apparatus 695 according to another embodiment rotation axis part is connected to the first body part 610 and the second body part 630, and penetrates the unlocking units 660A and 660B, the first body part 610, and the second body part 630.

The center axes that are the rotation centers of the first body part 610, the second body part 630, the unlocking units 660A and 660B may be matched with one another by the locking apparatus rotation axis part 695, and thus the unlocking units 660A and 660B that are formed to be the origin symmetric with respect to the center may push the locking main body parts 653A1, 653A2, 653B1, and 653B2 simultaneously which face each other, the control of the movement of the first body part 610 to the second body part 630 in both directions (that is, in the clockwise or counterclockwise direction), and the locking performance, may be improved.

Additionally, the locking apparatus rotation axis part 695 may prevent the change of the interval between the first body part 610 and the second body part 630 that is preset in the circumferential direction.

It is advantageous that the stuck-type locking apparatus according to the embodiments of the disclosure may be switched to a locking state at any positions of the first body part and the second body part that move relative to each other.

In other words, in the unlocking state, the second body part may move to the first body part within a certain range, and thus the locking apparatus is capable of switching regardless of the position of the second body part to the first body part.

Furthermore, when the locking apparatus is switched to the locking state, the locking apparatus enters the locking state regardless of the movement clearance of the first body part and the second body part.

For the release of a locking state of the locking apparatus according to the embodiments of the disclosure, the unlocking unit for pushing the locking unit in a direction in which the interval between the first body part and the second body part increases is provided in the form of rotating coaxially with the rotation axes of the first body part and the second body part. However, the concept of the disclosure is not limited thereto, and a method of pushing a locking unit may be modified in various ways, which includes various modified methods of pushing a locking unit under the concept of pushing a locking unit for the release of a locking state.

Furthermore, although the pushing plate part capable of linear motion for the rotation of the unlocking unit capable of rotating according to the embodiments of the disclosure is provided, the method of moving an unlocking unit that pushes a locking unit for the release of a locking state may be modified in various ways. The concept of the disclosure is not limited thereto, which includes various modified methods of moving the unlocking unit under the concept of moving the unlocking unit that pushes the locking unit for the release of a locking state.

<Example of a Surgical Instrument Provided with the Locking Apparatus According to Another Embodiment>

A surgical instrument provided with the locking apparatus according to another embodiment (hereinafter, referred to as the "surgical instrument") is described below with reference to the accompanying drawings.

FIGS. 9A and 9B are perspective views of a surgical instrument provided with the locking apparatus according to another embodiment. Referring to FIGS. 9A and 9B, the surgical instrument 1 provided with the locking apparatus according to another embodiment may include an end tool, a connection part, a manipulation part 30, the locking apparatuses 400A, 400B, 500A, and 500B, and a control part.

Figure 18:
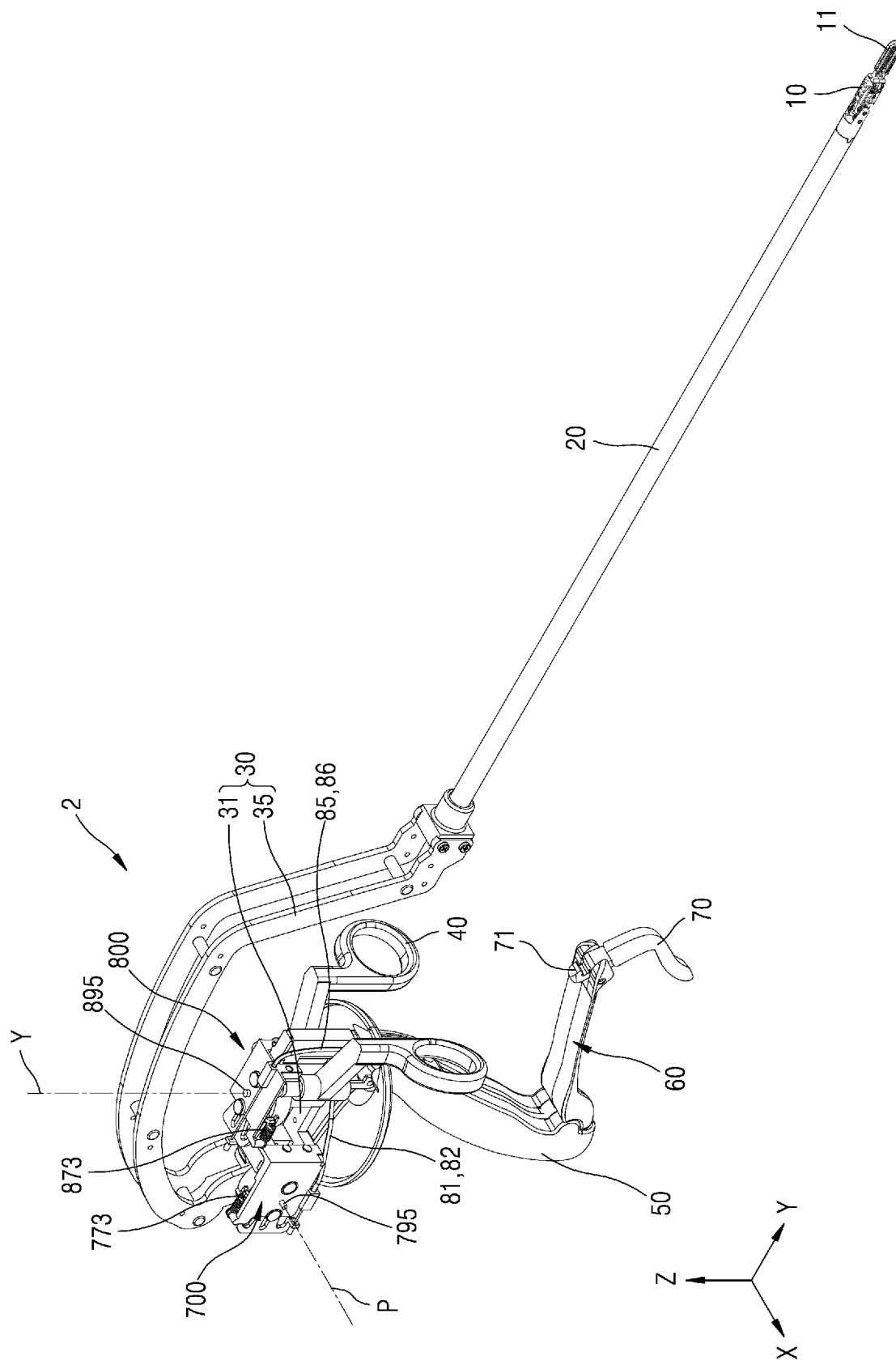
FIG. 18 is a perspective view of a surgical instrument provided with the locking apparatus according to another embodiment.

In this state, as the end tool and the connection part are the same as an end tool 10 and a connection part 20 illustrated in FIG. 18, reference numerals are indicated together.

As the end tool 10 is the same element as the end tool 10 of the surgical instrument 2 where a locking apparatus according to another embodiment that is described later is installed, a detailed description thereof is presented later.

The surgical instruments 1 and 2 where the locking apparatuses according to other embodiments of the disclosure are respectively installed may be manually moved for laparoscopic surgery or various other surgeries. A surgeon may perform surgery on a surgical site by manually operating the surgical instruments 1 and 2 by hands.

In the surgical instruments 1 and 2 where the locking apparatuses according to other embodiments of the disclosure are respectively installed, it is one feature that, when a handle part 50 or a finger ring part 40 is rotated in one direction with respect at least one of pitch, yaw, and actuation operations, the end tool is rotated in the intuitively same direction as the operation direction of the handle part 50 and the finger ring part 40.

In the disclosure, it is a feature that the gripping of the end tool 10 is possible by the actuation operation of the finger ring part 40, and the rotation operation of the end tool 10 is possible by the rotation of the handle part 50 or the finger ring part 40.

in the specification, the actuation operation denotes that, while rotating around an axis parallel to a yaw motion rotation axis or other axis, as a center, each of a plurality of finger ring parts provided as the finger ring part 40 rotates in opposite directions to be closed or opened.

Due to the actuation operation of the finger ring part 40, power transmission wires 41 and 42 that are described later transmit power to the end tool 10, and the actuation operation of the end tool 10 where a plurality of jaws are formed is performed.

Referring to FIGS. 9A and 9B, when the finger ring part 40 or the handle part 50 rotates, the power transmission wires 41 and 42 that connect the end tool 10 and the finger ring part 40 or the handle part 50 move on the manipulation part 30, and thus the pitch, yaw, and actuation operations of the end tool 10 are possible.

Referring to FIGS. 9A and 9B, the manipulation part 30 may include the pitch manipulation part 31, the yaw manipulation part 32, and the bent part 35.

In the disclosure, although the power transmission wires 41 and 42 are provided in one pair, the disclosure is not limited thereto, and various modifications of the embodiments are possible such that the power transmission wires 41 and 42 may be provided in one body or may include three or more power transmission wires according to the operation design of the end tool 10 of the surgical instrument 1.

In other words, when a user holds the handle part 50 and performs a pitch or yaw motion, the manipulation part 30, particularly a relative movement among the pitch manipulation part 31, the yaw manipulation part 32, and the bent part 35 allows the power transmission wires 41 and 42 to move, and consequently the pitch or yaw motion of the end tool 10 occurs.

In the disclosure, although the relative movement among the pitch manipulation part 31, the yaw manipulation part 32, and the bent part 35 causes a rotational motion, the disclosure is not limited thereto, and the relative movement may cause a linear motion such as a sliding motion.

In the disclosure, the rotational motion of the pitch manipulation part 31 and the yaw manipulation part 32 causes the rotational motion of the end tool 10, and when the rotational motion of the pitch manipulation part 31 and the yaw manipulation part 32 is restricted by the locking apparatuses 400A, 400B, 500A, and 500B, the rotational motion of the end tool 10 is restricted as well.

In the surgical instrument 1, each of the pitch manipulation part 31 and the yaw manipulation part 32 is capable of rotational motion in a clockwise or counterclockwise direction, and may include two locking apparatuses for restricting a rotational motion in both directions.

In other words, the two locking apparatuses 400A and 400B may be provided to restrict a rotational motion of the pitch manipulation part 31 in both directions, and the two locking apparatuses 500A and 500B may be provided to restrict a rotational motion of the yaw manipulation part 32 in both directions.

In the disclosure, a user controls the locking apparatuses 400A, 400B, 500A, and 500B through the control part to control a relative movement among the pitch manipulation part 31, the yaw manipulation part 32, and the bent part 35.

The control part may include the finger ring part 40, the handle part 50, a first lever part 60, a second lever part 70, a hook part 71, wire parts 81 and 85, wire tube parts 82 and 86, and a wire holder part 61.

In the disclosure, although the control part controls the relative movement among the pitch manipulation part 31, the yaw manipulation part 32, and the bent part 35 through the movements of the wire parts 81 and 85, the disclosure is not limited thereto, and various modifications of the embodiments are possible such that the relative movement may be controlled in a slide method or a button method.

In the specification, the wire part denotes a first wire 81 and a second wire 85, and the wire tube part denotes a first wire tube 82 and a second wire tube 86.

Referring to FIGS. 9A and 9B, the surgical instrument 1 according to an embodiment of the present disclosure may include a plurality of locking apparatuses, particularly the first locking apparatus 400A, the second locking apparatus 400B, the third locking apparatus 500A, and the fourth locking apparatus 500B.

A pitch motion of the manipulation part 30 of the surgical instrument 1 is performed by the relative movement between the pitch manipulation part 31 and the bent part 35, and the relative movement refers to a rotational motion in both clockwise and counterclockwise directions.

To restrict the relative movement in both directions, two one-way locking apparatuses are provided together.

Likewise, a yaw motion of the manipulation part 30 of the surgical instrument 1 is performed by a relative movement between the pitch manipulation part 31 and the yaw manipulation part 32, and the relative movement refers to a rotational motion in both clockwise and counterclockwise directions.

For the restriction of the relative movement in both directions, two one-way locking apparatuses are provided together.

Referring to FIGS. 9A and 9B, the structure, operational principle, and effect of each of the first locking apparatus 400A and the second locking apparatus 400B are the same as those of the locking apparatus 300 according to another embodiment, detailed descriptions of redundant elements thereof are omitted.

The first locking apparatus 400A may be formed such that the interval between the first body part 410A and the second body part 430A, which face each other, decrease clockwise with respect to the center of the first body part 410A.

In the first locking apparatus 400A, the first body part 410A is coupled to the pitch manipulation part 31 and capable of rotating around the pitch axis as a center axis, and the second body part 430A is coupled to the bent part 35.

Referring to FIG. 9A, in the first locking apparatus 400A, the interval between the first body part 410A and the second body part 430A decreases clockwise (viewed in a negative X-axis direction with respect to the pitch axis in FIG. 9A), and Accordingly, the rotation of the first body part 410A to the second body part 430A in the in the counterclockwise direction (viewed in the negative X-axis direction with respect to the pitch axis in FIG. 9A) may be prevented.

Consequently, the pitch manipulation part 31 may be prevented from rotating in the in the counterclockwise direction (viewed in the negative X-axis direction with respect to the pitch axis in FIG. 9A) with respect to the bent part 35.

In the specification, the "negative X-axis direction" denotes a direction from the right to the left with respect to a Y-Z plane in FIG. 9A.

Meanwhile, the second locking apparatus 400B may be formed to prevent the pitch manipulation part 31 from rotating in the clockwise direction (viewed in the negative X-axis direction with respect to the pitch axis in FIG. 9A) with respect to the bent part 35.

When the second locking apparatus 400B is coupled to the manipulation part 30 by being reversed in the opposite direction to the first locking apparatus 400A with respect to the pitch axis, the second locking apparatus 400B may prevent the pitch manipulation part 31 from rotating in a direction opposite to the rotational direction that is prevented by the first locking apparatus 400A.

In other words, as shown in FIG. 9B, the second locking apparatus 400B may be located in a direction opposite to the first locking apparatus 400A, the first body part 410B is coupled to the pitch manipulation part 31 to rotate around the pitch axis as a center axis, and the second body part 430B is coupled to the bent part 35.

Referring to FIG. 9B, when viewed in a positive X-axis direction (in a direction from the left to the right with respect to the Y-Z plane in FIG. 9B), the interval between the first body part 410B and the second body part 430B of the second locking apparatus 400B decreases in the clockwise direction (based on the positive X-axis direction in FIG. 9B). Accordingly, the rotation of the first body part 410B to the second body part 430B in the in the counterclockwise direction (based on the positive X-axis direction in FIG. 9B) may be prevented.

As a result, the rotation of the pitch manipulation part 31 to the bent part 35 in the counterclockwise direction (based on the positive X-axis direction in FIG. 9B) may be prevented.

In other words, when viewed with respect to the first locking apparatus 400A (viewed based on the negative X-axis direction in FIG. 9A), the rotation of the pitch manipulation part 31 to the bent part 35 in the clockwise direction is prevented.

In FIG. 9A, the negative X-axis direction denotes a direction from the right to the left with respect to the Y-Z plane in FIG. 9A.

Accordingly, when the first locking apparatus 400A and the second locking apparatus 400B simultaneously enter the locking state, the rotation of the pitch manipulation part 31 to the bent part 35 in both clockwise and counterclockwise directions may be simultaneously prevented.

Accordingly, a pitch motion, particularly a rotational motion of the pitch manipulation part 31 and the yaw manipulation part 32, the finger ring part 40, and the handle part 50 connected thereto relative to the bent part 35 around the pitch axis as a center axis may be prevented.

Consequently, this brings an effect of preventing the end tool 10 from performing a pitch motion.

In this state, various modifications of the embodiments are possible such that each of the first body parts 410A and 410B of the first locking apparatus 400A and the second locking apparatus 400B is coupled to the bent part 35, and each of the second body parts 430A and 430B is coupled to the pitch manipulation part 31.

Referring to FIGS. 9A and 9B, when pushing plate main bodies 471A and 471B are moved, power is transmitted to each of unlocking units 460A and 460B so that locking unit is moved in a direction in which the interval between the second body parts 430A and 430B and the first body parts 410A and 410B increases.

Accordingly, as the second body parts 430A and 430B are capable of relative movement with respect to the first body parts 410A and 410B, the rotational motion of the pitch manipulation part 31 and the yaw manipulation part 32, the finger ring part 40, and the handle part 50 connected thereto to the bent part 35 around the pitch axis as a center axis is possible, and thus the pitch motion of the end tool 10 is possible.

Referring to FIGS. 9A and 9B, as the structure, operational principle, and effect of each of the third locking apparatus 500A and the fourth locking apparatus 500B are the same as those of the locking apparatus 300 according to another embodiment, detailed descriptions of redundant elements thereof are omitted.

The third locking apparatus 500A may be formed such that the interval between the first body part 510A and the second body part 530A, which face each other, decreases in the clockwise direction with respect to the center of the first body part 510A.

In the third locking apparatus 500A, the first body part 510A is coupled to the yaw manipulation part 32 and may be capable of rotating around the yaw axis as a center, and the second body part 530A is coupled to the pitch manipulation part 31.

Referring to FIG. 9A, in the third locking apparatus 500A, the interval between the first body part 510A and the second body part 530A decreases in the clockwise (viewed in the negative Z-axis direction with respect to the yaw axis in FIG. 9A). Accordingly, the rotation of the first body part 510A to the second body part 530A in the counterclockwise direction (viewed in the negative Z-axis direction with respect to the yaw axis in FIG. 9A) may be prevented.

Consequently, the rotation of the yaw manipulation part 32 to the pitch manipulation part 31 in the counterclockwise direction (viewed in the negative Z-axis direction with respect to the yaw axis in FIG. 9A) may be prevented.

In the specification, the "negative Z-axis direction" denotes a direction from the top to the bottom with respect to the X-Y plane in FIGS. 9A and 9B.

Meanwhile, the fourth locking apparatus 500B may be formed to prevent the rotation of the yaw manipulation part 32 to the pitch manipulation part 31 in the clockwise (in the negative Z-axis direction with respect to the yaw axis in FIG. 9A).

When the fourth locking apparatus 500B is coupled to the manipulation part 30 by being reversed in the opposite direction to the third locking apparatus 500A with respect to the yaw axis, the prevention in the opposite direction to the rotational direction prevented by the third locking apparatus 500A is possible.

In other words, as illustrated in FIGS. 9A and 9B, the fourth locking apparatus 500B facing the third locking apparatus 500A is located, the first body part 510B is coupled to the yaw manipulation part 32 and may rotate around the yaw axis as a center axis, and the second body part 530B is coupled to the pitch manipulation part 31.

Referring to FIGS. 9A and 9B, when the fourth locking apparatus 500B is viewed in the positive Z-axis direction (in the direction from the bottom to the top with respect to the X-Y plane in FIG. 9A), that is, from the bottom to the top (based on FIG. 9A), the interval between the first body part 510B and the second body part 530B of the fourth locking apparatus 500B decreases in the clockwise direction (based on the positive Z-axis direction in FIG. 9A). Accordingly, the rotation of the first body part 510A to the second body part 530B in the counterclockwise direction (based on the positive Z-axis direction in FIG. 9A) may be prevented.

As a result, the rotation of the yaw manipulation part 32 with respect to the pitch manipulation part 31 in the counterclockwise direction (based on the positive Z-axis direction in FIG. 9A) may be prevented.

In other words, when viewed based on the third locking apparatus 500A (based on the negative Z-axis direction in FIG. 9A), the rotation of the yaw manipulation part 32 to the pitch manipulation part 31 in the clockwise direction is prevented.

The negative Z-axis direction in FIG. 9A denotes the direction from the top to the bottom with respect to the X-Y plane in FIG. 9A.

Accordingly, when the third locking apparatus 500A and the fourth locking apparatus 500B simultaneously enter the locking state, the rotation of the yaw manipulation part 32 to the pitch manipulation part 31 in both clockwise and counterclockwise directions may be simultaneously prevented. Accordingly, a yaw motion, particularly a rotational motion of the yaw manipulation part 32 and the finger ring part 40 and the handle part 50 connected thereto relative to the pitch manipulation part 31 around the yaw axis as a center axis may be prevented.

Consequently, this brings an effect of preventing the end tool 10 from performing a yaw motion.

Various modifications of the embodiments are possible such that each of the first body parts 510A and 510B of the third locking apparatus 500A and the fourth locking apparatus 500B is coupled to the pitch manipulation part 31, and each of the second body parts 530A and 530B is coupled to the yaw manipulation part 32.

Referring to FIGS. 9A and 9B, when a pushing plate main body 571 is moved, power is transmitted to each of unlocking units 560A and 560B so that locking unit 550A and 550B are moved in a direction in which the interval between the second body parts 530A and 530B and the first body parts 510A and 510B increases.

Accordingly, as the first body parts 510A and 510B are capable of relative movement with respect to the second body parts 530A and 530B, the rotational motion of the yaw manipulation part 32 and the finger ring part 40 and the handle part 50 connected thereto with respect to the pitch manipulation part 31 around the yaw axis as a center axis is possible, and thus the yaw motion of the end tool 10 is possible.

While, in the surgical instrument 1 provided with the locking apparatus according to another embodiment as illustrated in FIGS. 9A and 9B, only the one-way movement of each of the first body parts 410A, 410B, 510A, and 510B with respect to each of the second body parts 430A, 430B, 530A, and 530B is prevented, in the surgical instrument 2 provided with the locking apparatus according to another embodiment as illustrated in FIG. 18, a fifth locking apparatus 700 that is singular and prevents a relative movement in both directions controls a pitch motion, and a sixth locking apparatus 800 that is singular and prevents a relative movement in both directions controls a yaw motion. However, as other elements except the locking apparatus having the above difference, particularly the end tool 10, the connection part 20, the manipulation part 30, the finger ring part 40, the power transmission wires 41 and 42, the handle part 50, the first lever part 60, the second lever part 70, the hook part 71, the first wire 81, the first wire tube 82, the second wire 85, the second wire tube 86, and the wire holder part 61, have the same operational principle and effect, related descriptions are presented in detail in the surgical instrument 2 provided with the locking apparatus according to another embodiment that is described later.

Furthermore, the locking apparatuses 400A, 400B, 500A, and 500B described in the specification, are capable of at least one operation of pitch, yaw, and actuation operations of the above-described surgical instrument, not applied only to an apparatus capable of joint movement.

Furthermore, in the surgical instrument 1 where the locking apparatuses 400A, 400B, 500A, and 500B according to the embodiments are installed, not only the locking apparatuses 400A, 400B, 500A, and 500B according to the embodiments, but also the locking apparatus 100 according to the embodiment and the locking apparatus 200 according to another embodiment, which are locked or unlocked through a linear motion, may be employed.

In the present embodiment, in the configuration of a locking apparatus for the restriction of a pitch motion or a yaw motion, two one-way locking apparatuses are provided for the restriction of each motion in both directions.

Various modifications of the embodiments of a method of forming two one-way locking apparatuses for the restriction of each of a pitch motion and a yaw motion may be possible.

In other words, in the present embodiment, the one-way locking apparatuses for restricting the rotational motion in the same direction are provided by being reversed (in the opposite reference rotation axis directions of the rotational motion), so as to restrict the rotational motion of a pitch or yaw motion in both directions, but other modified configurations may be possible.

For example, different from the present embodiment, one-way locking apparatuses that restrict a rotational motion in the opposite directions are configured to have a rotation axis in the same direction, so as to be configured to restrict the rotational motion of a pitch or yaw motion in both directions.

Accordingly, the configuration described in the present embodiment does not limit the concept of the disclosure, is to explain the concept that one-way locking apparatus is provided in twos to restrict a rotational motion of a certain motion (a pitch or yaw motion) in both directions, and is to be understood as including various modified examples under such a concept.

<Example of a Surgical Instrument Provided with the Locking Apparatus According to Another Embodiment>

A surgical instrument provided with the locking apparatus according to another embodiment (hereinafter, referred to as the "surgical instrument") is described below with reference to the accompanying drawings.

Figure 19:
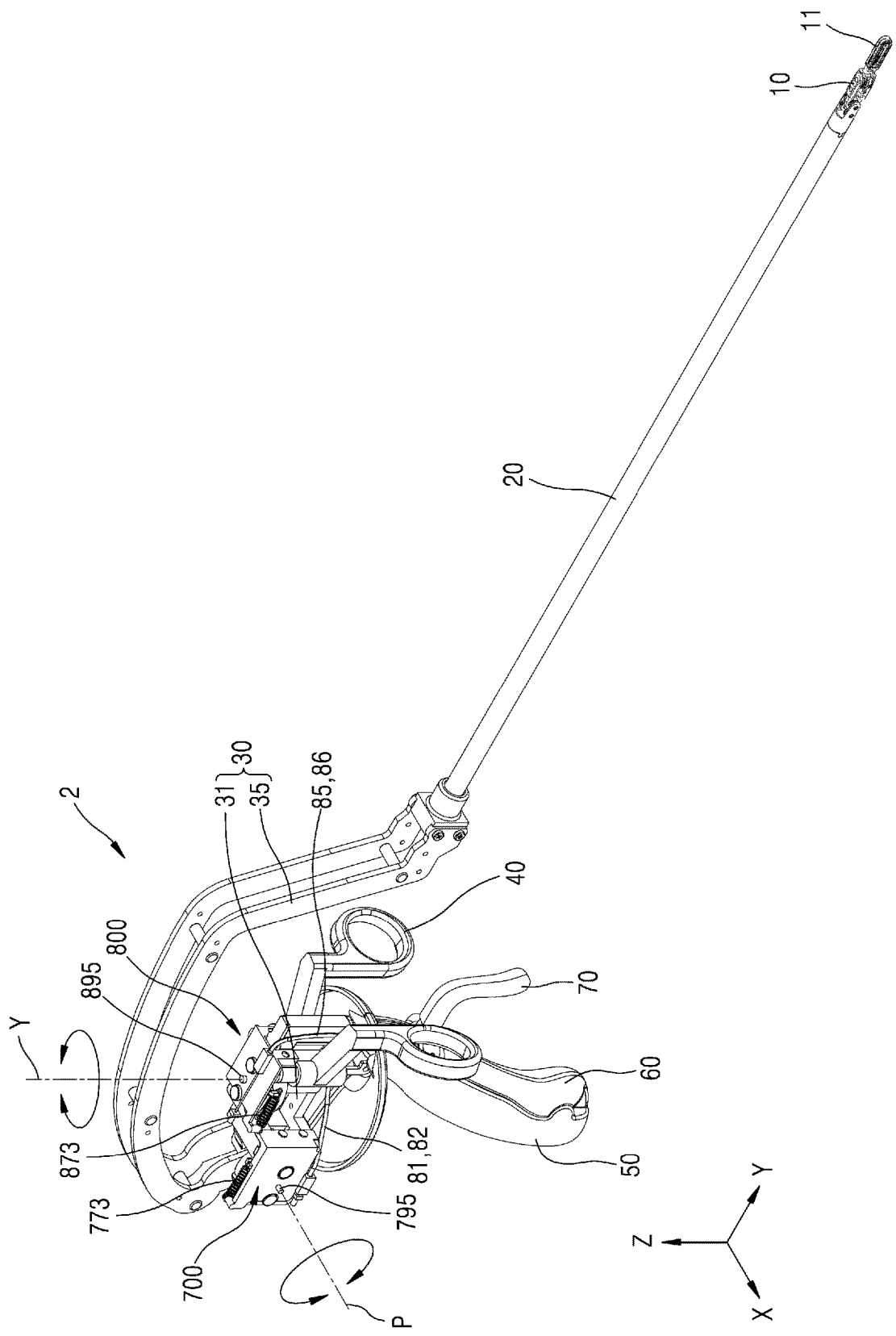
FIG. 19 illustrates an unlocking state of the locking apparatus of FIG. 18.
Figure 20:
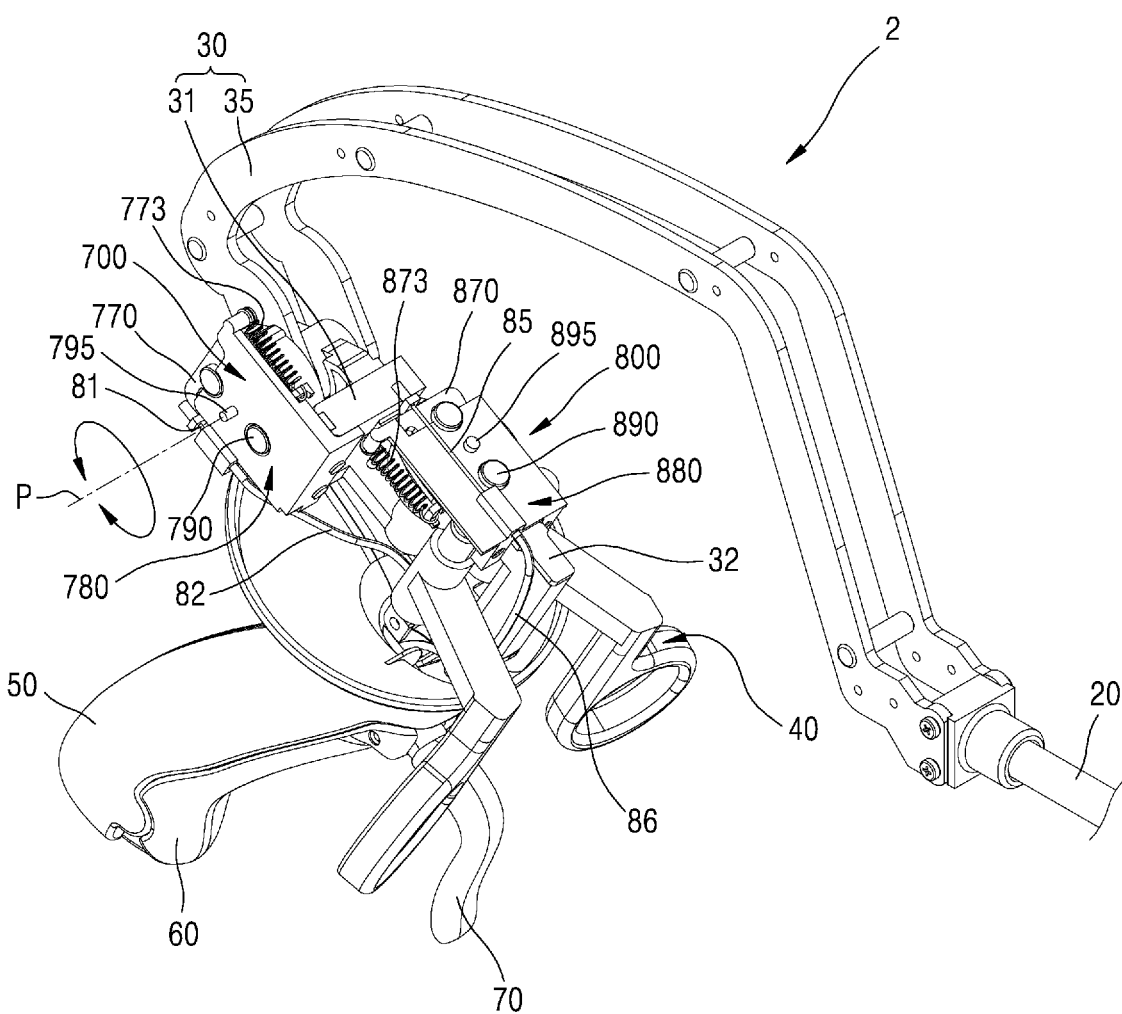
FIGS. 20 and 21 illustrate a pitch motion state of a surgical instrument provided with the locking apparatus according to another embodiment.
Figure 21:
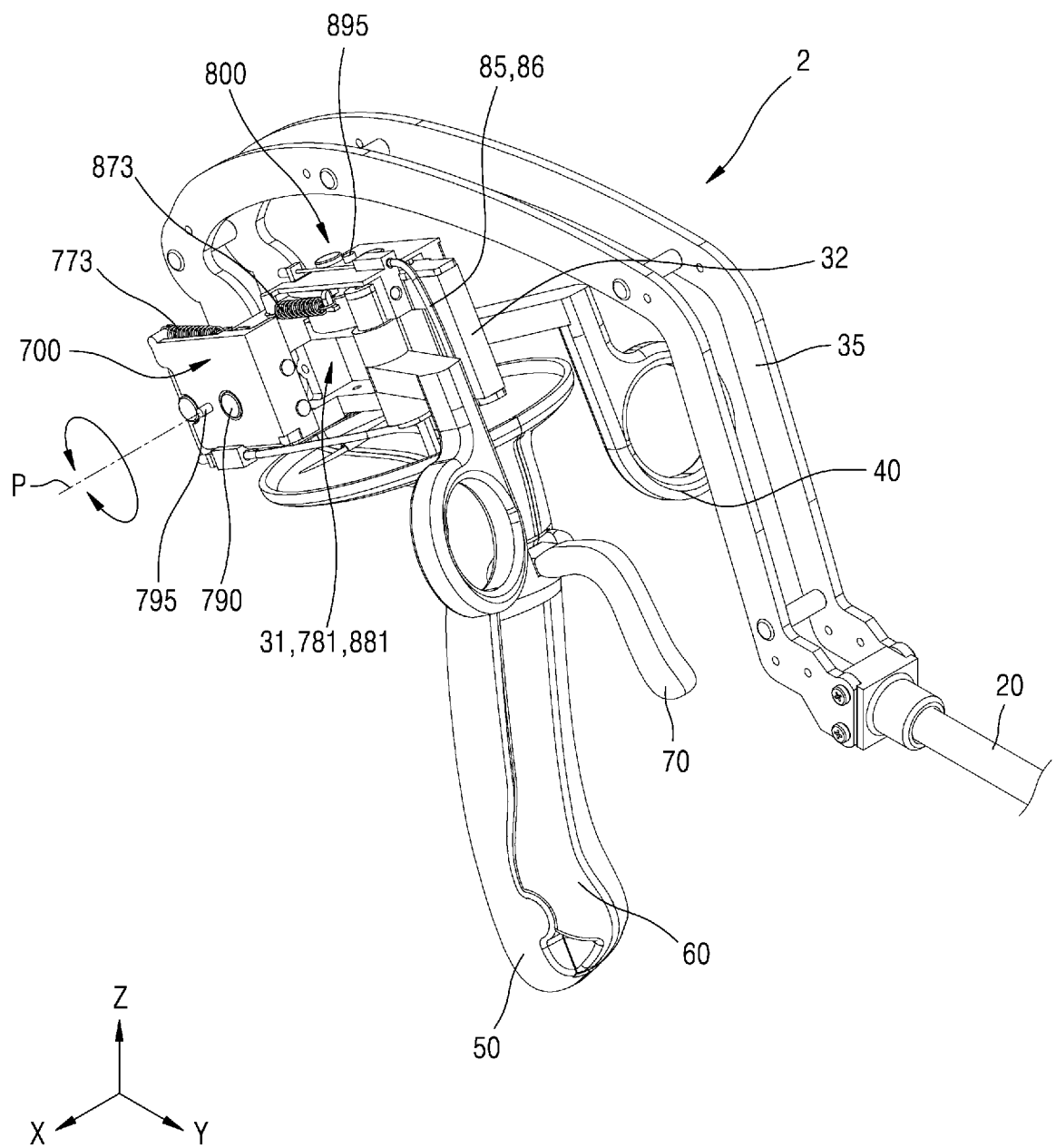
Figure 22:
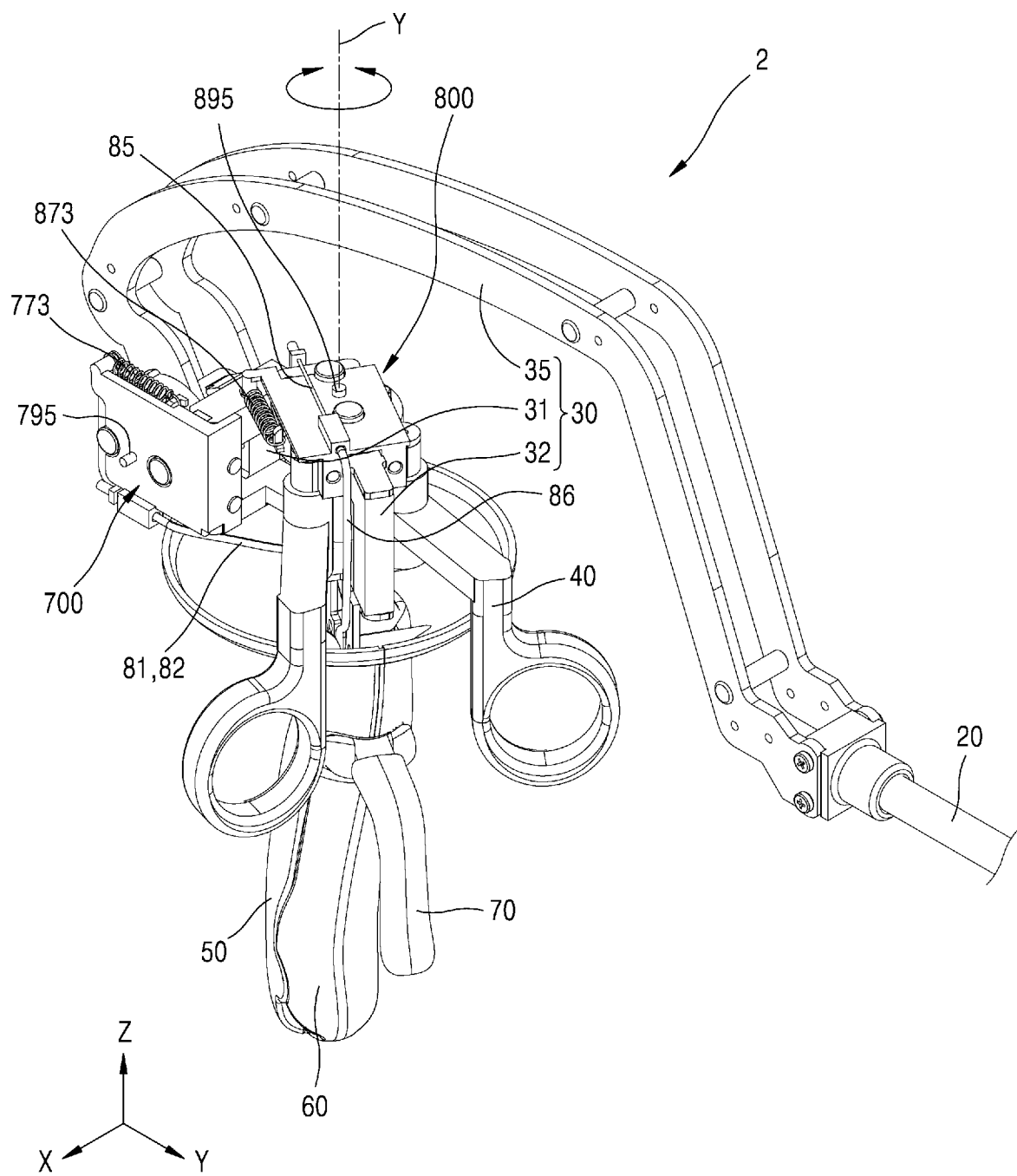
FIGS. 22 and 23 illustrate a yaw motion state of a surgical instrument provided with the locking apparatus according to another embodiment.
Figure 23:
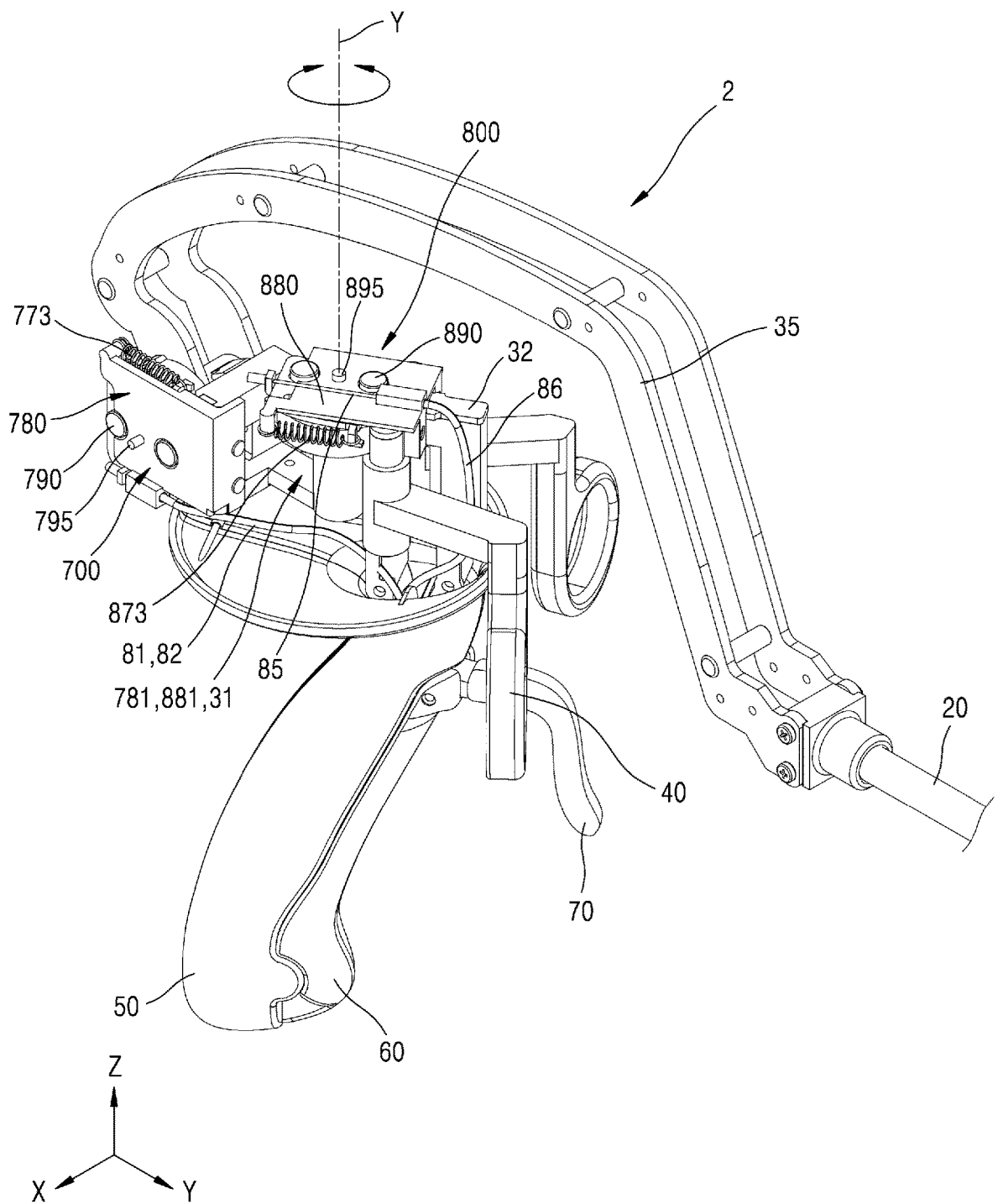
Figure 24:
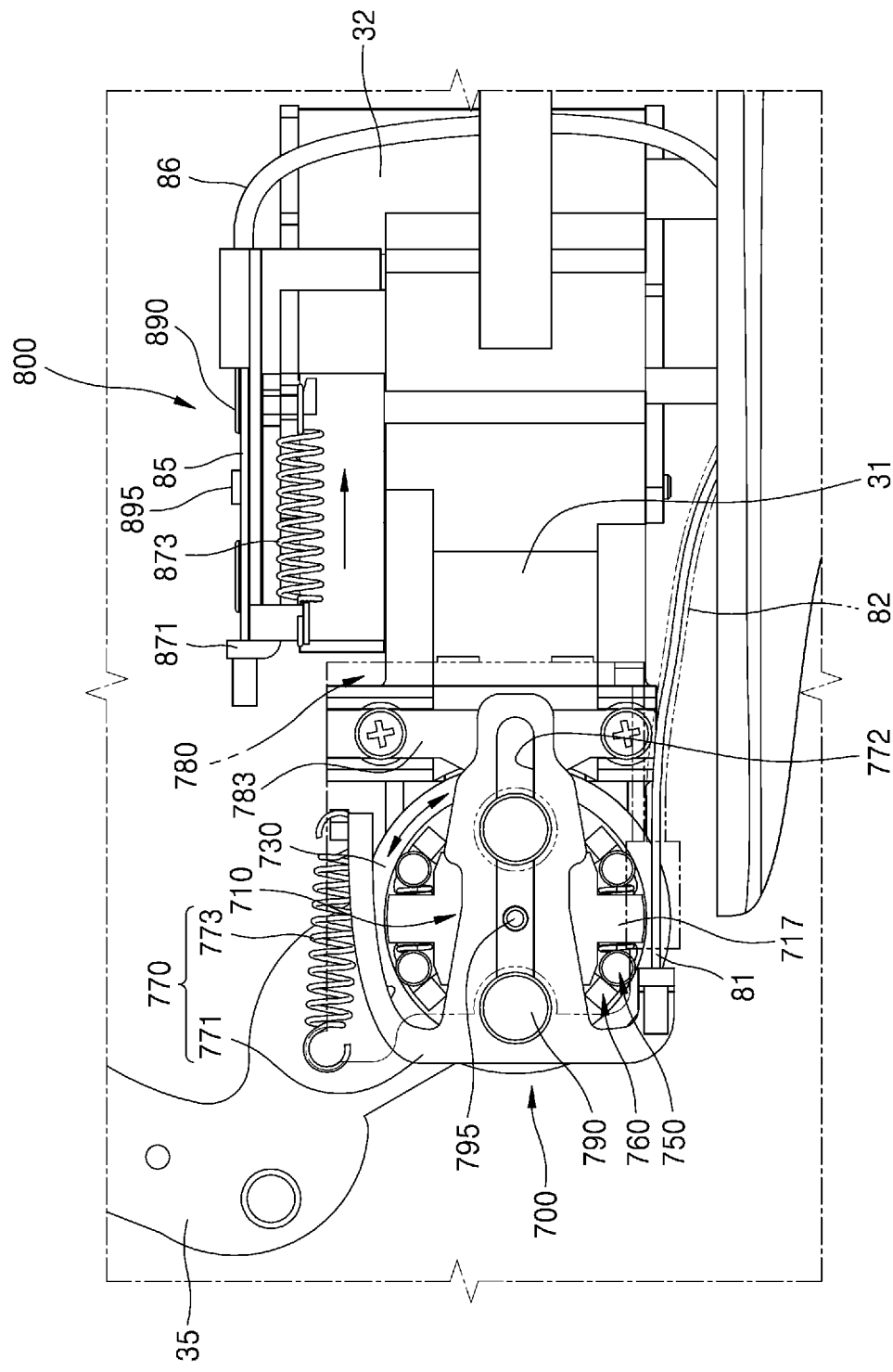
FIG. 24 is an enlarged view illustrating an unlocking state of the locking apparatus for managing a pitch motion in the surgical instrument according to an embodiment.
Figure 25:
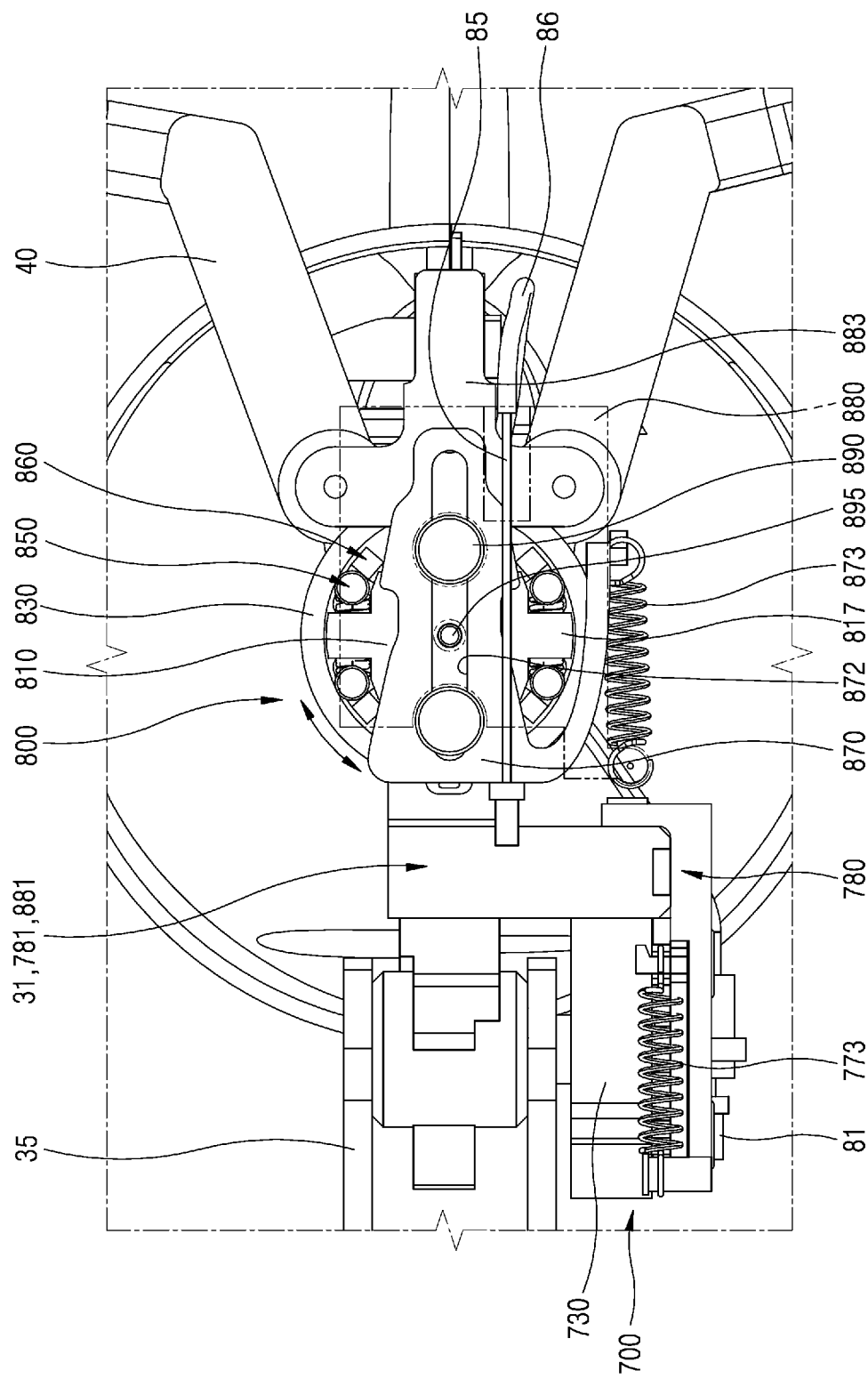
FIG. 25 is an enlarged view illustrating an unlocking state of the locking apparatus for managing a yaw motion in the surgical instrument according to an embodiment.
Figure 26:
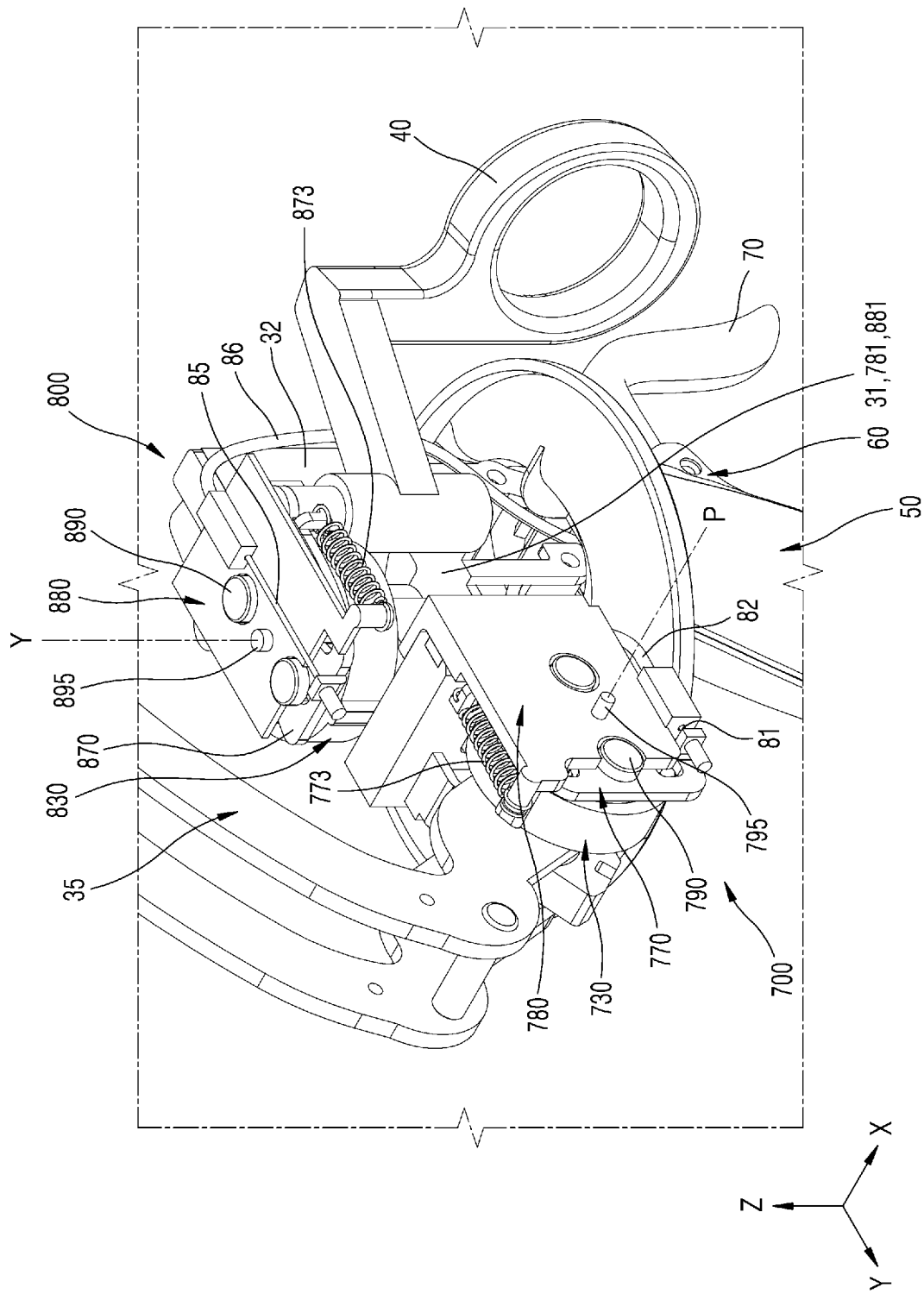
FIG. 26 is a partial perspective view illustrating an unlocking state of the locking apparatus for managing pitch and yaw motions in the surgical instrument according to an embodiment.
Figure 27:
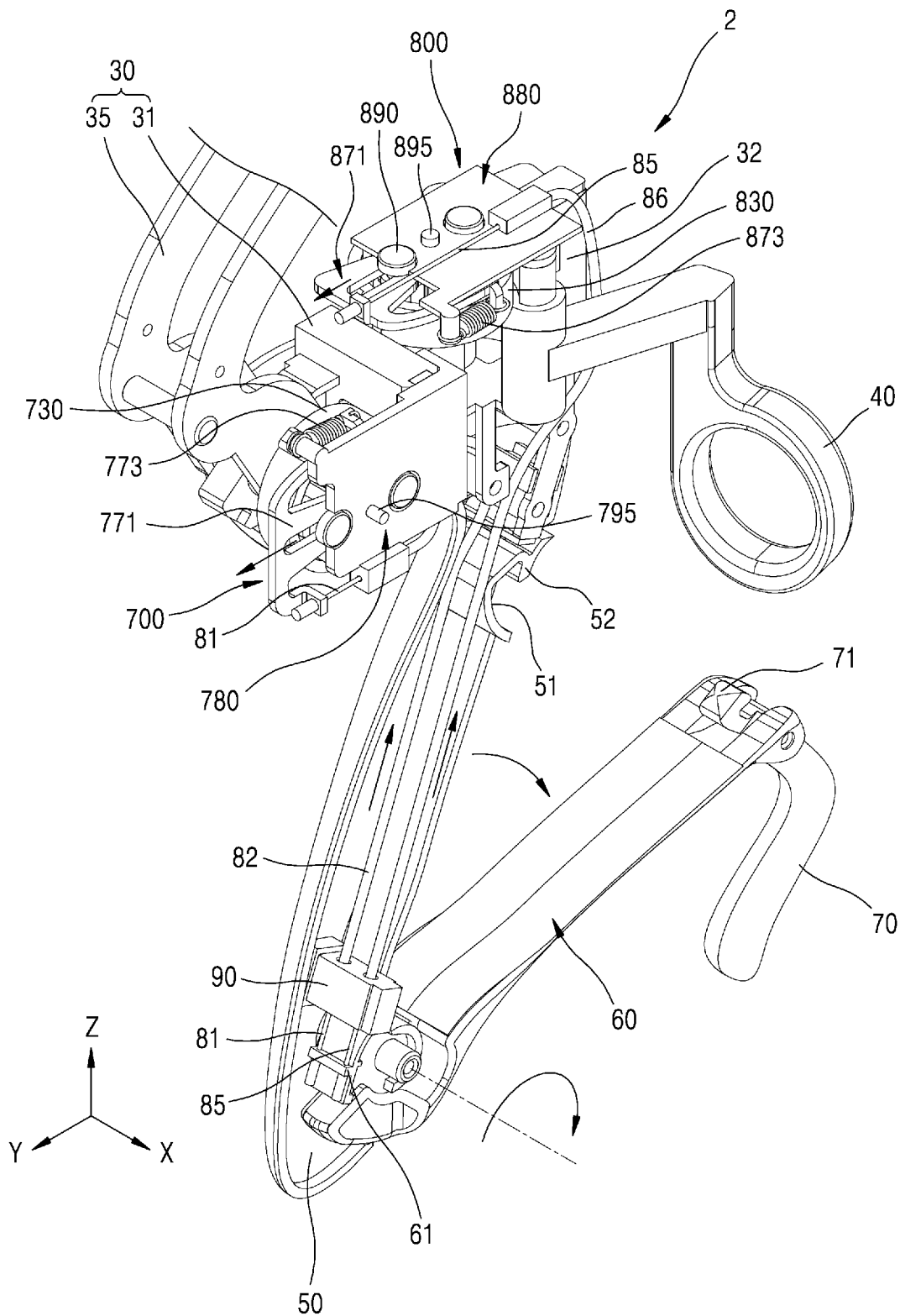
FIG. 27 is a partial perspective view illustrating a locking state of the locking apparatus for managing pitch and yaw motions in the surgical instrument according to an embodiment.
Figure 28:
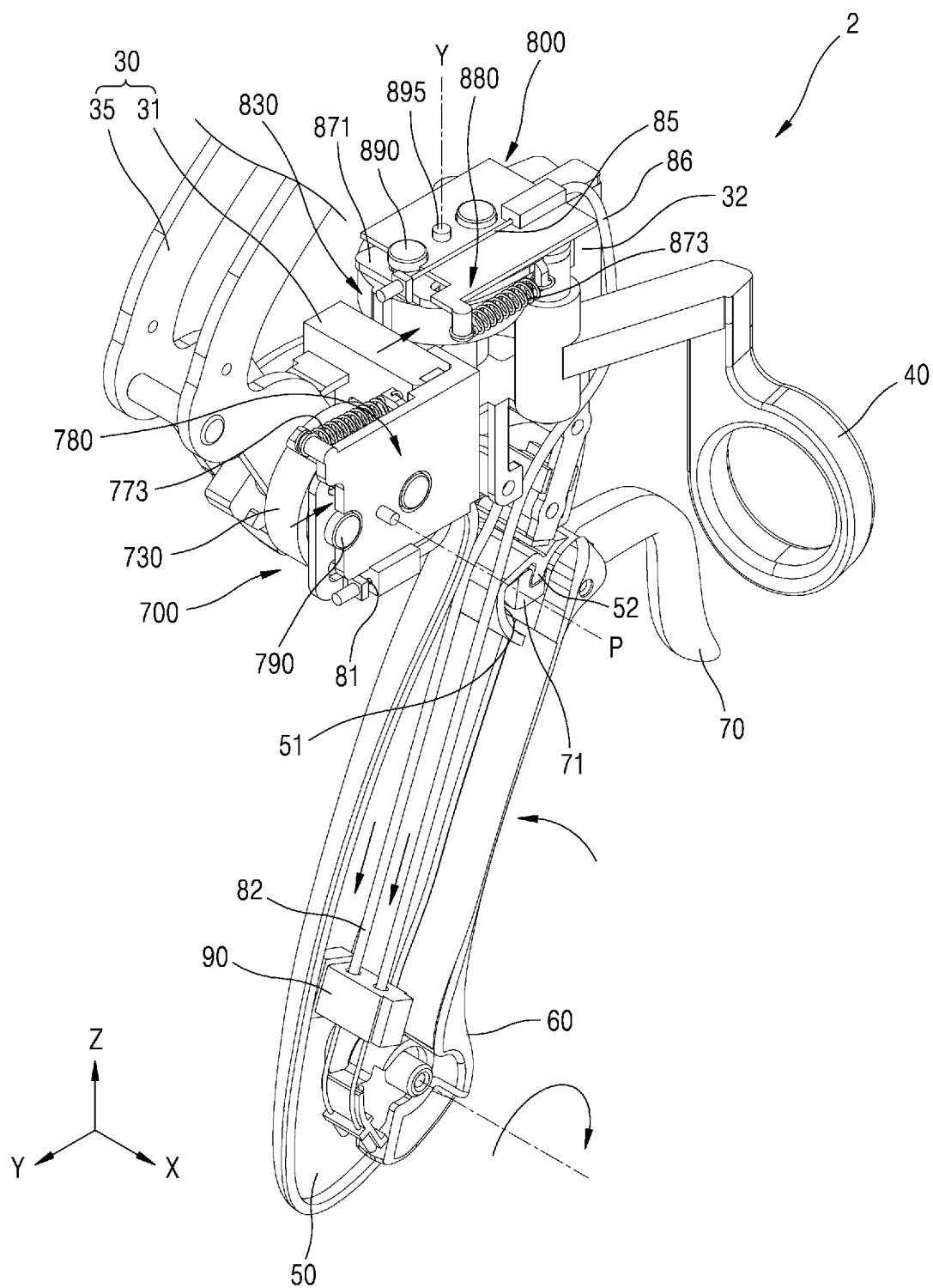
FIG. 28 illustrates an unlocking state of the locking apparatus in the surgical instrument according to an embodiment.

FIG. 18 is a perspective view of a surgical instrument provided with the locking apparatus according to another embodiment. FIG. 19 illustrates an unlocking state of the locking apparatus of FIG. 18. FIGS. 20 and 21 illustrate a pitch motion state of a surgical instrument provided with the locking apparatus according to another embodiment. FIGS. 22 and 23 illustrate a yaw motion state of a surgical instrument provided with the locking apparatus according to another embodiment. FIG. 24 is an enlarged view illustrating an unlocking state of the locking apparatus for managing a pitch motion in the surgical instrument according to an embodiment. FIG. 25 is an enlarged view illustrating an unlocking state of the locking apparatus for managing a yaw motion in the surgical instrument according to an embodiment. FIG. 26 is a partial perspective view illustrating an unlocking state of the locking apparatus for managing pitch and yaw motions in the surgical instrument according to an embodiment. FIG. 27 is a partial perspective view illustrating a state of the locking apparatus for managing pitch and yaw motions in the surgical instrument according to an embodiment. FIG. 28 illustrates an unlocking state of the locking apparatus in the surgical instrument according to an embodiment.

Referring to FIGS. 18 to 28, the surgical instrument 2 provided with the locking apparatus according to another embodiment may include the end tool 10, the connection part 20, the manipulation part 30, the locking apparatuses 700 and 800, and the control part.

In the disclosure, a user controls the locking apparatuses 700 and 800 through the control part, thereby controlling a relative movement among the pitch manipulation part 31, the yaw manipulation part 32, and the bent part 35.

The control part may include the finger ring part 40, the handle part 50, the first lever part 60, the second lever part 70, the hook part 71, the wire parts 81 and 85, the wire tube parts 82 and 86, and the wire holder part 61.

In the disclosure, although the control part controls a relative rotational motion among the pitch manipulation part 31, the yaw manipulation part 32, and the bent part 35 through the movements of the wire parts 81 and 85, the disclosure is not limited thereto, and various modifications of the embodiments such as a slide type relative linear motion or a button type are possible.

In the specification, the wire part denotes the first wire 81 and the second wire 85, and the wire tube part denotes the first wire tube 82 and the second wire tube 86.

Referring to FIGS. 18 to 28, in the surgical instrument 2 provided with the locking apparatus according to another embodiment, the locking apparatuses 700 and 800 include a plurality of locking apparatuses, and the locking apparatuses 700 and 800 may control a pitch motion and a yaw motion, respectively.

Referring to FIG. 18, the end tool 10 according to an embodiment of the present disclosure may include a jaw that is described later and provided at one end of the connection part 20, and may perform rotating, gripping, and cutting through a certain structure. The jaw is formed to be capable of rotating in two or more directions.

The end tool 10 is engaged with the manipulation part 30 that is described later, and when the movement of the manipulation part 30 is prevented by the locking apparatuses 700 and 800, the movement of the end tool 10 may be prevented as well.

Referring to FIG. 18, the pitch motion denotes rotating around the pitch axis as a rotation center, and the yaw motion denotes rotating around the yaw axis as a rotation center. A user holds the handle part 50 with a hand and inserts a finger into the finger ring part 40, thereby manipulating the end tool 10 through the pitch motion, the yaw motion, and the actuation operation.

In the specification, the pitch axis for a pitch motion may denote a first rotation axis in a claim, and the yaw axis for a yaw motion may denote a second rotation axis in a claim.

Furthermore, a user may perform a pitch motion and a yaw motion while holding the handle part 50 using a hand, particularly, referring to FIG. 18, perform a pitch motion around the pitch axis as a rotation center and a yaw motion around the yaw axis as a rotation center while holding the handle part 50.

Referring to FIG. 18, the connection part 20 according to an embodiment of the present disclosure has a hollow shaft shape, in which one or more wires may be accommodated, and has one end portion to which the manipulation part 30, the finger ring part 40, and the handle part 50, to which the locking apparatuses 700 and 800 are connected, may be connected and the other end portion to which the end tool 10 may be connected.

Referring to FIG. 18, the manipulation part 30 according to an embodiment of the present disclosure is capable of joint movement and may include the pitch manipulation part 31, the yaw manipulation part 32, and the bent part 35.

Referring to FIG. 19, the yaw manipulation part 32 is capable of relative movement with respect to the pitch manipulation part 31 around the yaw axis as a center axis.

The yaw manipulation part 32 may be connected to the finger ring part 40 and the handle part 50 so as to be engagingly moved (or rotated) as a user manipulates the finger ring part 40 and the handle part 50.

In other words, when a user performs a yaw motion around the yaw axis as a rotation center by holding the handle part 50 or inserting a finger into the finger ring part 40, the yaw manipulation part 32, the handle part 50, and the finger ring part 40 altogether are yaw-rotated around the yaw axis as a rotation center.

Referring to FIG. 19, the pitch manipulation part 31 may perform a relative movement with respect to the bent part 35 around the pitch axis as a rotation center.

The pitch manipulation part 31 is connected to the yaw manipulation part 32, the finger ring part 40, and the handle part 50, and when a user performs a pitch motion rotating around the pitch axis as a rotation center by holding the handle part 50 or inserting a finger into the finger ring part 40, the pitch manipulation part 31 and the yaw manipulation part 32, the handle part 50, and the finger ring part 40 altogether pitch-rotate around the pitch axis as a rotation center.

Referring to FIGS. 18 to 28, as the configuration of the locking apparatuses 700 and 800 of the surgical instrument 2 provided with the locking apparatus according to another embodiment, particularly the locking apparatus 700 for controlling a pitch motion and the locking apparatus 800 for controlling a yaw motion, is the same as that of the locking apparatus 600 according to another embodiment, except that the locking apparatus 700 for controlling a pitch motion rotates around the pitch axis as a rotation center and the locking apparatus 800 for controlling a yaw motion rotates around the yaw axis as a rotation center, detailed descriptions of any redundant portions are omitted.

In the specification, in the surgical instrument 2 provided with the locking apparatus according to another embodiment, a locking apparatus for controlling a pitch motion and a locking apparatus for controlling a yaw motion are defined to be the fifth locking apparatus and the sixth locking apparatus, respectively.

However, in the specification, the first locking apparatus and the second locking apparatus in claim 11 denote the fifth locking apparatus 700 and the sixth locking apparatus 800, respectively.

Referring to FIG. 24, in the fifth locking apparatus 700 of the surgical instrument 2 according to another embodiment, a first body part 710 is connected to the pitch manipulation part 31 and may rotate around the pitch axis as a center axis, and a second body part 730 may be connected to the bent part 35.

Referring to FIGS. 18 and 24, the second body part 730 may be coupled to the bent part 35, and as the first body part 710 moves relative to the second body part 730, the pitch manipulation part 31 may rotate relative to the bent part 35.

As the first body part 710 and the second body part 730 rotate relative to each other around the pitch axis as a rotation center, the pitch manipulation part 31 and the bent part 35 may rotate relative to each other.

Referring to FIGS. 18 to 28, in the surgical instrument 2 provided with the locking apparatus according to another embodiment, a pushing plate part 770 is coupled to the first wire 81, and as the first wire 81 is moved due to the rotation of the first lever part 60 that is described later and by a pushing plate elastic part 773, the pushing plate part 770 may move in any one direction (based on the Y-axis in FIG. 18).

In this state, the pushing plate elastic part 773 may be a tension spring resisting tension and may facilitate a movement of the pushing plate part 770 in any one direction.

Referring to FIGS. 18, 24, and 27, as the pushing plate part 770 moves, a locking unit 750 is stuck between the first body part 710 and the second body part 730 capable of moving relative to each other, and thus a locking state in which a relative movement between the first body part 710 and the second body part 730 in both directions is prevented may be established by due to a frictional force generated at this time.

Referring to FIGS. 19, 20, 21, 24, and 28, as a pushing plate main body 771 pushes an unlocking unit 760, a relative movement between the first body part 710 and the second body part 730 is possible, and thus an unlocking state may be possible in which the pitch manipulation part 31 rotates around the pitch axis as a rotation center with respect to the bent part 35.

Referring to FIG. 18, as the first lever part 60 that is described later rotates around the X-axis as a rotation center with respect to the handle part 50, the pushing plate main body 771 is moved in a "locking direction".

The "locking direction" denotes a negative Y-axis direction from the right to the left with respect to an X-Z plane (based on FIG. 18). Furthermore, an "unlocking direction" denotes a positive Y-axis direction from the left to the right with respect to the X-Z plane (based on FIG. 18).

As the locking unit 750, particularly a locking main body part 753, is stuck between the first body part 710 and the second body part 730, a frictional force is generated, and a locking state may be established, in which a relative movement between the first body part 710 and the second body part 730, particularly a pitch motion that is a relative movement of the bent part 35 and the pitch manipulation part 31, is prevented.

Referring to FIGS. 18, 19, 22, 23, and 25, a second body part 830 of the sixth locking apparatus 800 of the surgical instrument 2 according to another embodiment is coupled to the pitch manipulation part 31, and a first body part 810 may be connected to the yaw manipulation part 32, the handle part 50, and the finger ring part 40.

However, the disclosure is not limited thereto, and various modifications of the embodiments are possible such that, in the fifth locking apparatus 700, the first body part 710 is connected to the bent part 35 and the second body part 730 is connected to the pitch manipulation part 31, and in the sixth locking apparatus 800, the second body part 830 is connected to the yaw manipulation part 32, the handle part 50, and the finger ring part 40, and the first body part 810 is connected to the pitch manipulation part 31.

Referring to FIGS. 24 and 25, a base part 880, particularly a second base 883, may be integrally formed with the yaw manipulation part 32 or separately formed therefrom so as to be coupled to the first body part 810 and the yaw manipulation part 32. The second base 883 may additionally include a portion having a cover shape.

Referring to FIG. 23, the second body part 830 is coupled to the pitch manipulation part 31, and the first body part 810 may rotate with the yaw manipulation part 32, the handle part 50, and the finger ring part 40, altogether, around the yaw axis as a rotation center.

Referring to FIG. 23, as the first body part 810 moves with respect to the second body part 830, the yaw manipulation part 32 and the handle part 50 that are connected to the finger ring part 40 with respect to the pitch manipulation part 31 may rotate around the yaw axis as a rotation center.

In other words, as the first body part 810 and the second body part 830 moves relative to each other around the yaw axis as a rotation center, the finger ring part 40 and the handle part 50 that are connected to the yaw manipulation part 32 may rotate relative to the pitch manipulation part 31.

Referring to FIGS. 18 to 25, in the surgical instrument 2 provided with the locking apparatus according to another embodiment, a pushing plate main body 871 of a pushing plate part 870 of the sixth locking apparatus 800 is coupled to the second wire 85, and as the second wire 85 is moved due to the rotation of the first lever part 60 that is described later and by a pushing plate elastic part 873, the pushing plate part 870 may be moved in a "locking direction".

In this state, the pushing plate elastic part 873 may be a tension spring resisting tension and may facilitate a movement of the pushing plate part 870 in any one direction.

Referring to FIG. 18 or 25, as the pushing plate part 870 is moved, a locking unit 850, particularly a locking main body part 853, is stuck between the first body part 810 and the second body part 830 capable of moving relative to each other, and thus, a locking state in which a relative movement between the first body part 810 and the second body part 830 is prevented may be established by a frictional force generated at this time.

Referring to FIGS. 19, 22, 23, and 25, as the pushing plate main body 871 pushes an unlocking unit 860, a relative movement between the first body part 810 and the second body part 830 is possible, and thus an unlocking state may be established, in which the yaw manipulation part 32 that is connected to the handle part 50 and the finger ring part 40 rotates around the yaw axis as a rotation center with respect to the pitch manipulation part 31.

FIG. 18 illustrates a locking state, in which, as the first lever part 60 rotates with respect to the handle part 50, the pushing plate main body 871 is moved in the "locking direction", and as the locking unit 850, particularly the locking main body part 853, is stuck between the first body part 810 and the second body part 830, a frictional force is generated, and accordingly a locking state may be established, in which a relative movement between the first body part 810 and the second body part 830, particularly a yaw motion that is a relative movement between the pitch manipulation part 31 and the yaw manipulation part 32, is prevented.

Referring to FIGS. 18, 19, 27, and 28, the finger ring part 40 of the surgical instrument 2 according to another embodiment is connected to the yaw manipulation part 32 to rotate around a rotation axis thereof as a center, thereby controlling the actuation operation of the end tool 10.

In the unlocking state of the sixth locking apparatus 800, the handle part 50 and the yaw manipulation part 32 altogether may yaw-rotate around the yaw axis as a rotation center, and in the unlocking state of the fifth locking apparatus 700, the handle part 50, the yaw manipulation part 32, and the pitch manipulation part 31 altogether may pitch-rotate around the pitch axis as a rotation center.

In the locking state of the sixth locking apparatus 800 in which the relative movement of the first body part 810 and the second body part 830 is prevented, the finger ring part 40 may rotate around the rotation axis thereof as a center to perform the actuation operation of the end tool 10, but the rotation of the handle part 50 and the yaw manipulation part 32 altogether around the yaw axis as a rotation center is prevented.

Referring to FIGS. 18, 19, 27, and 28, the handle part 50 of the surgical instrument 2 provided with the locking apparatus according to another embodiment is connected to the manipulation part 30, and as a user manipulates the finger ring part 40 with a finger, actuation operation that is gripping of the end tool 10, particularly a jaw, may con controlled, and a palm portion wraps and holds the handle part 50 to control a pitch motion and a yaw motion.

The handle part 50 is connected to the manipulation part 30, and a user holds the handle part 50 and performs a pitch motion, that is, a pitch motion that the pitch manipulation part 31 and the yaw manipulation part 32 altogether rotate around the pitch axis as a rotation center with respect to the bent part 35.

Furthermore, a yaw motion, particularly an operation that the yaw manipulation part 32 and the finger ring part 40 altogether rotate around the yaw axis as a rotation center with respect to the pitch manipulation part 31, may be performed.

Referring to FIG. 27, the handle part 50 has a hollow inside and may provide a movement path of the first wire 81, the first wire tube 82, the second wire 85, and the second wire tube 86 that are described later.

The handle part 50 is connected to the first lever part 60, and the first lever part 60 may rotate around a rotation axis L1 of the first lever part 60 (based on FIG. 27) as a rotation center at a certain portion of the handle part 50. A tube holder part 90 that is described later is installed inside the handle part 50 to fix the position of certain portions of the first wire tube 82 and the second wire tube 86, and the first wire 81 and the second wire 85 are located inside the first wire tube 82 and the second wire tube 86, respectively.

Furthermore, the first wire 81 and the second wire 85 are provided to move inside the first wire tube 82 and the second wire tube 86, respectively.

Although it is not illustrated in the drawings, the tube holder part 90 may be not only formed inside the handle part 50, but also coupled to second bases 783 and 883 or integrally formed with the second bases 783 and 883.

Although it is not illustrated in the drawings, as illustrated in FIGS. 9A and 9B, the power transmission wires 41 and 42 that connect the end tool 10, the finger ring part 40, and the handle part and are movable on the manipulation part 30 may be provided.

Referring to FIGS. 27 and 28, the first lever part 60 of the surgical instrument 2 provided with the locking apparatus according to another embodiment is installed between the handle part 50 and the second lever part 70 that is described later. Particularly, one side of the first lever part 60 may be rotatably coupled to the handle part 50, and the second lever part 70 may be rotatably coupled to the other side thereof opposite to the one side.

Referring to FIGS. 27 and 28, the wire holder part 61 is formed at the first lever part 60, and one side of each of the first wire 81 and the second wire 85 is coupled to the wire holder part 61 so that the locations of the first wire 81 and the second wire 85 may be fixed.

Referring to FIGS. 27 and 28, as the first lever part 60 rotates around the rotation axis L1 of the first lever part 60 (based on FIG. 27) as a rotation center with respect to the handle part 50, the wire holder part 61 may move the first wire 81 and the second wire 85 in a direction (first direction) from the top to the bottom or in a direction (second direction) from the bottom to the top, with respect to the handle part 50.

Referring to FIG. 27, when the first lever part 60 rotates in a direction to be released from the handle part 50, the first wire 81 and the second wire 85 are moved in the second direction. Accordingly, pushing plate parts 770 and 870 of the fifth locking apparatus 700 and the sixth the locking apparatus 800, particularly one end portion of each of pushing plate main bodies 771 and 871 to which the first wire 81 and the second wire 85 are coupled, is moved in the "locking direction" (based on the negative Y-axis direction from the right to the left with respect to the X-Z plane in FIG. 27).

As the pushing plate main bodies 771 and 871 move in the "locking direction", the locking units 750 and 850 are moved in a direction in which the interval between the first body parts 710 and 810 and the second body parts 730 and 830 decreases. Due to a frictional force generated as the locking units 750 and 850 are respectively stuck between the first body parts 710 and 810 and the second body parts 730 and 830, a locking state is established, in which a relative movement between the first body parts 710 and 810 and the second body parts 730 and 830 is prevented.

Referring to FIG. 28, when the first lever part 60 rotates in a direction to be coupled to the handle part 50, the first wire 81 and the second wire 85 are moved in the first direction. Accordingly, the pushing plate parts 770 and 870 of the fifth locking apparatus 700 and the sixth the locking apparatus 800, particularly the pushing plate main bodies 771 and 871, are moved in the "unlocking direction" (based on the positive Y-axis direction from the left to the right with respect to the X-Z plane in FIG. 28).

In this state, as it is in the unlocking stat in which the first body parts 710 and 810 and the second body parts 730 and 830 of the fifth locking apparatus 700 and the sixth the locking apparatus 800 are capable of moving relative to each other, while a user holds the handle part 50 and the finger ring part 40, the user may control a pitch motion around the pitch axis as a rotation center and a yaw motion around the yaw axis as a rotation center.

Referring to FIGS. 27 and 28, the second lever part 70 of the surgical instrument 2 provided with the locking apparatus according to another embodiment is rotatably coupled to the first lever part 60 and may rotate a rotation axis L2 of the second lever part 70 as a rotation center at a certain portion of the first lever part 60. The second lever part 70 is rotatably coupled to the first lever part 60 and detachably coupled to the handle part 50.

The second lever part 70 is detachably coupled to the handle part 50 in a hook method, and the hook part 71 may be formed in one end portion of the second lever part 70.

Referring to FIGS. 27 and 28, a catch recess part 51 is formed in the handle part 50 to have the hook part 71 accommodated therein, and a catch step part 52 may protrude from an end portion of the catch recess part 51 to catch the hook part 71.

The second lever part 70 may extend in one direction with respect to the rotation center and then may be bent downward (based on FIG. 27). The second lever part 70 may be shaped to be bent by a preset angle at a preset position.

Accordingly, while the first lever part 60 is coupled to the handle part 50, when a user rotates the first lever part 60 to be separated from the handle part 50 around the rotation axis L1 of the first lever part 60 as a rotation center. In this state, through a simple operation of pushing a certain bent part of the second lever part 70 with a finger, the second lever part 70 may be released from the handle part 50 and the first lever part 60 may be separated from the handle part 50.

In detail, as the second lever part 70 rotates relative to the first lever part 60 to allow the hook part 71 of the second lever part 70 to be released from the catch step part 52, the first lever part 60 is detached from the handle part 50 due to elastic resilience of a lever spring 65 connected to the first lever part 60, and thus the first lever part 60 may be away from the handle part 50.

The lever spring 65 of the surgical instrument 2 provided with the locking apparatus according to another embodiment may have a coil shape and elastic resilience to rotate around the rotation axis L1 of the first lever part 60 as a center axis in the clockwise or counterclockwise direction.

Referring to FIG. 27, the lever spring 65 may be installed at a portion where the handle part 50 and the first lever part 60 are connected to each other, and as the lever spring 65 has elastic resilience to rotate around the rotation axis L1 of the first lever part 60 in the clockwise direction (based on FIG. 27), and thus the first lever part 60 may be easily separated from the handle part 50.

Referring to FIGS. 18, 20, 24, 27, and 28, the first wire 81 of the surgical instrument 2 provided with the locking apparatus according to another embodiment penetrates the inside of the first wire tube 82 and connects the first lever part 60 to the fifth locking apparatus 700, and one side of the first wire 81 may be coupled to the pushing plate part 770 of the fifth locking apparatus 700, particularly the pushing plate main body 771, and the other side thereof may be coupled to the first lever part 60, particularly the wire holder part 61.

Referring to FIG. 27, when the first lever part 60 rotates in a direction to be released from the handle part 50, the first wire 81 rotates together and moves in the second direction as the wire holder part 61 rotates around the rotation axis L1 of the first lever part 60 as a rotation center.

Referring to FIGS. 24 to 28, as the first wire 81 moves in the second direction, the pushing plate main body 771 to which the first wire 81 is coupled is moved in the "locking direction". Accordingly, the unlocking unit 760 is moved in a direction, and the locking unit 750 is moved in a direction in which the interval between the first body part 710 and the second body part 730 decreases, to be stuck between the first body part 710 and the second body part 730 (in detail, a contact part (not shown) is moved by an elastic member (not shown) of the locking unit 750 to be stuck between the first body part 710 and the second body part 730). Accordingly, a locking state, in which a relative movement between the first body part 710 and the second body part 730 in both directions is prevented, is established by a frictional force generated therefrom.

Referring to FIG. 28, when the first lever part 60 rotates in a direction to be coupled to the handle part 50, the first wire 81 rotates together and moves in the first direction as the wire holder part 61 rotates around the rotation axis L1 of the first lever part 60 as a rotation center.

As the first wire 81 moves in the first direction, the pushing plate main body 771 to which the first wire 81 is coupled is moved in the "unlocking direction". Accordingly, the unlocking unit 760 is moved, and thus the locking unit 750 is moved in the direction in which the interval between the first body part 710 and the second body part 730 increases, as described above, and an unlocking state is established, in which a relative movement between the first body part 710 and the second body part 730 in both directions is possible.

The "unlocking direction" denotes a positive Y-axis direction from the left to the right with respect to the X-Z plane (based on FIG. 27). Furthermore, the "locking direction" denotes a negative Y-axis direction from the right to the left with respect to the X-Z plane (based on FIG. 27).

Referring to FIGS. 18, 20, 24, 27, and 28, the second wire 85 of the surgical instrument 2 provided with the locking apparatus according to another embodiment penetrates the inside of the second wire tube 86 and connects the first lever part 60 to the sixth locking apparatus 800, and one side of the second wire 85 may be connected to the pushing plate part 870 of the sixth locking apparatus 800, particularly the pushing plate main body 871, and the other side thereof may be connected to the first lever part 60, particularly the wire holder part 61.

Referring to FIG. 27, when the first lever part 60 rotates in a direction to be released from the handle part 50, the second wire 85 rotates together and moves in the second direction as the wire holder part 61 rotates around the rotation axis L1 of the first lever part 60 as a rotation center.

As the second wire 85 moves in the second direction, the pushing plate main body 871 to which the second wire 85 is coupled is moved in the "locking direction". Accordingly, the unlocking unit 860 is moved, and the locking unit 850 is moved in the direction in which the interval between the first body part 810 and the second body part 830 decreases, to be stuck between the first body part 810 and the second body part 830 (in detail, a contact part (not shown) is moved by an elastic member (not shown) of the locking unit 850 to be stuck between the first body part 810 and the second body part 830). Accordingly, a locking state, in which a relative movement the first body part 810 and the second body part 830 in both directions is prevented, is established by a frictional force generated therefrom.

Referring to FIGS. 19 and 28, when the first lever part 60 rotates in a direction to be coupled to the handle part 50, the second wire 85 rotates together and moves in the first direction as the wire holder part 61 rotates around the rotation axis L1 of the first lever part 60 as a rotation center.

As the second wire 85 moves in the first direction, the pushing plate main body 871 to which the second wire 85 is coupled is moved in the "unlocking direction". Accordingly, as the unlocking unit 860 is moved, as described above, the locking unit 850 is moved in a direction in which the interval between the first body part 810 and the second body part 830 increases, and thus an unlocking state is established, in which a relative movement between the first body part 810 and the second body part 830 in both directions is possible.

Referring to FIGS. 18, 20, 24, 27, and 28, the first and second wire tubes 82 and 86 of the surgical instrument 2 provided with the locking apparatus according to another embodiment are respectively disposed outside the first and second wires 81 and 85 and have a hollow tube shape such that the first and second wires 81 and 85 respectively penetrate the first and second wire tubes 82 and 86.

The first and second wire tubes 82 and 86 may include a flexible material, that is, an elastic material. Accordingly, when a user manipulates the surgical instrument 2 while holding the handle part 50, the shapes of the first and second wire tubes 82 and 86 are flexibly deformed inside the surgical instrument 2, thereby providing movement paths by stably accommodating the first and second wires 81 and 85.

One sides of the first and second wire tubes 82 and 86 are coupled to the base parts 780 and 880 of the fifth locking apparatus 700 and the sixth the locking apparatus 800, respectively, and the other side opposite to each of the one sides is coupled to the tube holder part 90 disposed inside the handle part 50.

The first and second wire tubes 82 and 86 may be fixed at two or more positions by the base part 780 and the tube holder part 90. Accordingly, the first and second wire tubes 82 and 86 provide a movement path of the first and second wires 81 and 85 and prevent the first and second wires 81 and 85 from being twisted during moving.

Additionally, during a pitch motion or a yaw motion of the surgical instrument 2, even when the handle part 50 moves, a distance between both fixing portions of the first and second wire tubes 82 and 86 is maintained constant. Accordingly, a distance between the first and second wires 81 and 85 accommodated in the first and second wire tubes 82 and 86 may be maintained constant, and thus the first and second wires 81 and 85 may be prevented from moving in the first direction or in the second direction. In other words, only when the first lever part 60 rotates, the first and second wires 81 and 85 are moved.

In the surgical instrument 2 provided with the locking apparatus according to another embodiment, a drive force of the finger ring part 40 may be transmitted to the end tool 10 so that the operation of the end tool 10 is intuitively manipulated by using the handle part 50 or the finger ring part 40.

Furthermore, in the fifth locking apparatus 700 and the sixth locking apparatus 800 of the surgical instrument 2 according to another embodiment, due to a frictional force generated as the locking units 750 and 850 are respectively stuck between the first body parts 710 and 810 and the second body parts 730 and 830, the pitch motion or the yaw motion of the surgical instrument 2 is locked or unlocked, and thus manipulation convenience of the surgical instrument 2 in a surgical process may be improved.

In the fifth locking apparatus 700 and the sixth locking apparatus 800 of the surgical instrument 2 according to the embodiments, as the locking units 750 and 850, the unlocking units 760 and 860, the pushing plate parts 770 and 870, the base parts 780 and 880, guide members 790 and 890, and locking apparatus rotation axis parts 795 and 895 have the same structures, operational principles, and effects as those of the locking apparatus 600 according to another embodiment, detailed descriptions of redundant elements thereof are omitted.

Referring to FIGS. 9A and 9B, in the surgical instrument 1 according to an embodiment of the present disclosure, the first locking apparatus 400A and the second locking apparatus 400B are coupled to each other to control a locking state of a pitch motion in both rotational directions, and likewise the third locking apparatus 500A and the fourth locking apparatus 500B are coupled to each other to control a locking state of a yaw motion in both rotational directions.

In the surgical instrument 1 according to an embodiment of the present disclosure, a pushing plate part that is singular transmits power to the unlocking unit 460 of each of the first locking apparatus 400A and the second locking apparatus 400B, and thus a locking unit is moved between the first body part 410 and the second body part 430 so that a locking or unlocking state of a pitch motion in both directions may be controlled. Furthermore, a pushing plate part 570 transmits power to an unlocking unit 560 of each of the third locking apparatus 500A and the fourth locking apparatus 500B, and thus a locking unit 550 is moved between a first body part 510 and a second body part 530 so that a locking or unlocking state of a yaw motion in both directions may be controlled.

Meanwhile, referring to FIGS. 18 to 28, in the surgical instrument 2 provided with the locking apparatus according to another embodiment, the pushing plate part 770 that is singular in the fifth locking apparatus 700 that is singular transmits power to the unlocking unit 760 so that the locking unit 750 is moved between the first body part 710 and the second body part 730, and thus a relative movement of the second body part 730 with respect to the first body part 710, that is, a locking or unlocking state of a pitch motion in both directions, may be controlled.

Furthermore, in the surgical instrument 2 provided with the locking apparatus according to another embodiment, the pushing plate part 870 that is singular in the sixth locking apparatus 800 that is singular transmits power to the unlocking unit 860 so that the locking unit 850 is moved between the first body part 810 and the second body part 830, and thus a relative movement of the second body part 830 with respect to the first body part 810, that is, a locking or unlocking state of a yaw motion in both directions may be controlled.

In the surgical instrument 2 provided with the locking apparatus according to another embodiment, in a locking apparatus that is singular, particularly the fifth locking apparatus 700, the locking unit 750 is capable of locking or unlocking a relative movement of the second body part 730 with respect to the first body part 710 in both directions, and in the sixth locking apparatus 800, the locking unit 850 is capable of locking or unlocking a relative movement of the second body part 830 with respect to the first body part 810 in both directions.

Accordingly, compared with the surgical instrument 1 according to an embodiment of the present disclosure, in which to prevent relative movements of the second body parts 430A, 430B, 530A, and 530B with respect to the first body parts 410A, 410B, 510A, and 510B in one direction, particularly the locking apparatuses 400A and 400B to control a pitch motion and the locking apparatuses 500A and 500B to control a yaw motion are respectively combined, ease of use may be improved by reducing the entire volume of the surgical instrument 2, and the locking apparatuses 700 and 800 that are singular are used to control a pitch motion and a yaw motion, respectively, thereby improving ease of use.

Furthermore, the locking apparatuses 700 and 800 described in the specification are capable of at least one of pitch, yaw, and actuation operations of the above-described surgical instrument, and are not limited only to an apparatus capable of joint movement.

Furthermore, the surgical instrument 2 where the locking apparatuses 700 and 800 according to the embodiment are installed, may adopt not only the locking apparatuses 700 and 800 according to the embodiments, but also the locking apparatus 100 according to an embodiment and the locking apparatus 200 according to another embodiment, which are locked or unlocking in a linear motion.

The surgical instruments 1 and 2 according to the embodiments of the disclosure where the above-described locking apparatus of a being-stuck type is advantageous in that the manipulation part capable of rotating or moving within a certain range may be immediately switched to a locking state regardless of the position of the manipulation part.

Furthermore, in the case of the surgical instrument 2 according to an embodiment of the disclosure, by moving only a single pushing plate part, the rotation of the second body part of each of the locking apparatuses 700 and 800 with respect to the first body part in both clockwise and counterclockwise directions, that is, setting and release of a locking state in both directions of a pitch motion and a yaw motion, is possible.

The particular implementations shown and described herein are illustrative examples of the disclosure and are not intended to otherwise limit the scope of the disclosure in any way. For the sake of brevity, conventional electronics, control systems, software development and other functional aspects of the systems may not be described in detail. Furthermore, the connecting lines, or connectors shown in the various figures presented are intended to represent functional relationships and/or physical or logical couplings between the various elements. It should be noted that many alternative or additional functional relationships, physical connections or logical connections may be present in a practical device. Moreover, no item or component is essential to the practice of the disclosure unless the element is specifically described as "essential" or "critical."

The use of the terms "a" and "an" and "the" and similar referents in the context of describing the disclosure (especially in the context of the following claims) are to be construed to cover both the singular and the plural. Furthermore, recitation of ranges of values herein are merely intended to serve as a shorthand method of referring individually to each separate value falling within the range, unless otherwise indicated herein, and each separate value is incorporated into the specification as if it were individually recited herein. Also, the steps of all methods described herein can be performed in any suitable order unless otherwise indicated herein or otherwise clearly contradicted by context. The disclosure is not limited to the described order of the steps. The use of any and all examples, or language (e.g., "such as") provided herein, is intended merely to better illuminate the disclosure and does not pose a limitation on the scope of the disclosure unless otherwise claimed. Numerous modifications and adaptations will be readily apparent to one of ordinary skill in the art without departing from the spirit and scope of the disclosure.

The embodiments of the disclosure can be written as computer programs and can be implemented in general-use digital computers that execute the programs using a computer readable recording medium. In this state, the medium may continuously store a program that can be executed by a computer, or may store a program for execution or download. Furthermore, the medium may be various recording devices or storing devices in which single or several hardware are combined, which it not limited to a medium that is directly accessed to a computer system and may be present over a network in a distribution manner. Examples of the medium include magnetic storage media such as floppy disks or hard disks, optical recording media such as CD-ROMs or DVDs, magneto-optical medium such as floptical disks, and Rom, RAM, flash memory, etc., which are configured to store program instructions. Furthermore, examples of other media may include application stores for distributing applications, sites for supplying or distributing other various software, and recording media or storing media managed at servers.

Although exemplary embodiments of the disclosure have been described for illustrative purposes, those having ordinary knowledge in the technical field of the disclosure will appreciate that various modifications, additions and substitutions are possible, without departing from the scope and spirit of the disclosure as disclosed in the accompanying claims. Therefore, the embodiments disclosed in the disclosure are intended to illustrate the scope of the technical idea of the disclosure, and the scope of the technical idea of the disclosure is not limited by the embodiments.

The protection scope of the disclosure should be construed based on the accompanying claims, and it should be construed that all of the technical ideas included within the scope equivalent to the claims are included within the right scope of the disclosure.

INDUSTRIAL APPLICABILITY

The disclosure provides a locking apparatus. Furthermore, the embodiments of the disclosure may be applied to industrially used locking mechanisms for preventing a relative movement between members different from each other.

The invention claimed is:

1. A locking apparatus comprising:
   a first body part;
   a second body part capable of a relative movement with respect to the first body part;
   at least one locking assembly capable of moving within an interval between the first body part and the second body part and simultaneously contacting the first body part and the second body part; and
   at least one unlocking assembly disposed on a movement path of the at least one locking assembly and capable of pushing the at least one locking assembly in a direction away from the first body part or the second body part,
   wherein, when the at least one locking assembly simultaneously contacts the first body part and the second body part, the movement of the second body part with respect to the first body part in at least one direction is prevented,
   wherein the at least one locking assembly comprises a locking main body part, and the locking main body part comprises:
   a contact part disposed between the first body part and the second body part; and
   an elastic member connected to the first body part, having an elastic restoring force, and pushing the contact part in a direction opposite to the pushing direction of the at least one unlocking assembly, and
   wherein the interval between the first body part and the second body part decreases towards the pushing direction of the elastic member.

2. The locking apparatus of claim 1, wherein the interval between the first body part and the second body part decreases in any one direction in a section where the first body part and the second body part face each other, and
   when the at least one locking assembly simultaneously contacts the first body part and the second body part in the section, the second body part is prevented from moving in the direction in which the interval with the first body part decreases.

3. The locking apparatus of claim 2, wherein the at least one unlocking assembly pushes the at least one locking assembly in a direction in which the interval between one side of the first body part and one side of the second body part, which face each other, in the section increases, so as to enable a relative movement between the first body part and the second body part, which is prevented by the at least one locking assembly.

4. The locking apparatus of claim 3, wherein the second body part is disposed inside the first body part, and one side of the second body part which faces the first body part forms the interval with the first body part decreasing in one direction, and the other side facing the one side contacts the first body part.

5. The locking apparatus of claim 4, wherein the second body part is flat and is movable inside the first body part.

6. The locking apparatus of claim 4, wherein the first body part extends to be symmetric toward both sides with respect to a center portion thereof,
the at least one locking assembly comprises a plurality of locking assemblies and is disposed at both sides of the center portion of the first body part,
the at least one unlocking assembly comprises a plurality of unlocking assemblies corresponding to the plurality of locking assemblies and is capable of pushing the plurality of locking assemblies, and
when the plurality of locking assemblies simultaneously contact the first body part and the second body part, the first body part and the second body part are prevented from moving in two directions.

7. The locking apparatus of claim 3, wherein the second body part is disposed inside the first body part, and the interval between inner circumferential surfaces of the first body part facing the second body part decreases in one direction.

8. The locking apparatus of claim 7, wherein the second body part is flat, and the first body part is symmetrically formed with respect to a movement axis of the second body part as an axis of symmetry.

9. The locking apparatus of claim 7, wherein the at least one locking assembly and the at least one unlocking assembly respectively comprise a plurality of locking assemblies and a plurality of unlocking assemblies, which are disposed at both sides with respect to a movement axis of the second body part as an axis of symmetry.

10. The locking apparatus of claim 9, wherein
the first body part extends to be symmetric toward both sides with respect to a center portion thereof,
the plurality of locking assemblies are disposed at both sides with respect to the center portion of the first body part,
the plurality of unlocking assemblies corresponding to the plurality of locking assemblies are capable of pushing the plurality of locking assemblies, and
when the plurality of locking assemblies simultaneously contact the first body part and the second body part, the first body part and the second body part are prevented from moving in two directions.

11. The locking apparatus of claim 3, wherein the second body part is coaxial with the first body part and rotatably disposed outside the first body part.

12. The locking apparatus of claim 11, wherein the second body part has a hollow, and the first body part is disposed inside the second body part.

13. The locking apparatus of claim 11, wherein the second body part is rotatable clockwise or counterclockwise.

14. The locking apparatus of claim 11, wherein the interval between the first body part and the second body part, which face each other, decreases in one of clockwise and counterclockwise directions.

15. The locking apparatus of claim 14, wherein
the at least one locking assembly comprises a plurality of locking assemblies in a movement direction of the second body part, and
the at least one unlocking assembly comprises a plurality of unlocking assemblies corresponding to the plurality of locking assemblies.

16. The locking apparatus of claim 11, wherein the interval between the first body part and the second body part decreases in one of clockwise and counterclockwise directions in at least one section where the first body part and the second body part face each other, and decreases in a direction different from the direction of the clockwise and counterclockwise directions in at least other section where the first body part and the second body part face each other.

17. The locking apparatus of claim 16, wherein
the one section and the other section each comprise a plurality of sections between the first body part and the second body part,
the at least one locking assembly comprises a plurality of locking assemblies corresponding to the plurality of sections, and
the at least one unlocking assembly comprises a plurality of unlocking assemblies corresponding to the plurality of locking assemblies.

18. The locking apparatus of claim 17, wherein the plurality of locking units comprises:
a first locking assembly capable of moving in the at least one section; and
a second locking assembly capable of moving in the at least other section, and,
when the first locking assembly and second locking assembly simultaneously contact the first body part and the second body part, the second body part is prevented from rotating in both clockwise and counterclockwise directions.

19. The locking apparatus of claim 18, wherein each of the first locking assembly and the second locking assembly is provided in one pair to be origin-symmetric with respect to a rotation center of the second body part as the origin.

20. The locking apparatus of claim 19, wherein the at least one unlocking assembly is coaxial with the first body part and the second body part and is capable of rotating clockwise or counterclockwise around the co-axis as a rotation axis.

21. The locking apparatus of claim 20, wherein the plurality of unlocking units comprises:
a first unlocking assembly capable of pushing the first locking assembly; and
a second unlocking assembly rotating in a direction opposite to a rotational direction of the first unlocking assembly and capable of pushing the second locking assembly.

22. The locking apparatus of claim 21, wherein each of the first and second unlocking assembly comprises an unlocking main body disposed on the movement path of the first and second locking assembly and is capable of pushing each of the first and second locking assemblies, respectively, in a direction in which the interval between the first body part and the second body part, which face each other, increases.

23. The locking apparatus of claim 22, wherein the unlocking main body of each of the first and second unlocking assembly comprises a plurality of unlocking main bodies capable of pushing the first and second locking assemblies, respectively, that are origin-symmetric with respect to a rotation center of the second body part as an origin and provided in one pair.

24. The locking apparatus of claim 21, further comprising a pushing plate part that transmits power to the first and second unlocking assemblies and is capable of pushing the first and second unlocking assemblies.

25. The locking apparatus of claim 24, wherein the pushing plate part linearly reciprocates and is capable of simultaneously pushing the first and second unlocking assemblies.

26. The locking apparatus of claim 24, wherein, when the pushing plate part pushes the first and second unlocking assemblies, the first and second unlocking assemblies are moved in a direction in which the interval between the first body part and the second body part, which face each other, increases.

27. The locking apparatus of claim 24, wherein each surface of the pushing plate part that contacts the first and second unlocking assemblies at both sides with respect to a movement axis of the pushing plate part is an inclined surface forming an angle with a movement axis of the pushing plate part.

28. The locking apparatus of claim 27, wherein the inclined surface comprises a plurality of inclined surfaces capable of pushing the first and second locking assemblies that are origin-symmetric with respect to a rotation center of the second body part as an origin and provided in one pair.

29. The locking apparatus of claim 11, wherein the at least one unlocking assembly is coaxial with the first body part and the second body part and is capable of rotating clockwise or counterclockwise around the co-axis as a rotation axis.

30. The locking apparatus of claim 29, wherein the at least one unlocking assembly comprises an unlocking main body that is disposed on the movement path of the at least one locking assembly and is capable of pushing the at least one locking assembly in a direction in which the interval between the first body part and the second body part, which face each other, increases.

31. The locking apparatus of claim 30, wherein
the at least one locking assembly comprises a plurality of locking units in a movement direction of the second body part, and
the unlocking main body comprises a plurality of unlocking main bodies corresponding to the plurality of locking units.

32. The locking apparatus of claim 29, further comprising a pushing plate part that transmits power to the at least one unlocking assembly and is capable of pushing the at least one unlocking assembly.

33. The locking apparatus of claim 32, wherein the pushing plate part is capable of pushing the at least one unlocking assembly while the pushing plate part linearly reciprocates.

34. The locking apparatus of claim 32, wherein, when one side of the pushing plate part pushes the at least one unlocking assembly, the at least one unlocking assembly moves in a direction in which the interval between the first body part and the second body part, which face each other, increases.

35. The locking apparatus of claim 32, wherein one surface of the pushing plate part capable of contacting the at least one unlocking assembly is an inclined surface forming an angle with a movement axis of the pushing plate part.

36. The locking apparatus of claim 1, wherein, as the contact part is pushed by the elastic member in the direction in which the interval between the first body part and the second body part decreases, a state in which the movement of the second body part with respect to the first body part in one or more directions is prevented is maintained.

37. The locking apparatus of claim 1, wherein the contact part has a ball shape or a cylindrical shape.

* * * * *